United States Patent
Chesnut et al.

(10) Patent No.: US 7,528,241 B2
(45) Date of Patent: May 5, 2009

(54) METHODS AND REAGENTS FOR MOLECULAR CLONING

(75) Inventors: Jonathan D. Chesnut, Carlsbad, CA (US); Stewart Shuman, New York, NY (US); Knut R. Madden, Carlsbad, CA (US); John A. Heyman, Vestal, NY (US); Robert P. Bennett, Encinitas, CA (US)

(73) Assignee: Life Technologies Corporation, Carlsbad, CA (US)

( * ) Notice: Subject to any disclaimer, the term of this patent is extended or adjusted under 35 U.S.C. 154(b) by 257 days.

(21) Appl. No.: 11/053,187

(22) Filed: Feb. 7, 2005

(65) Prior Publication Data

US 2005/0282184 A1 Dec. 22, 2005

Related U.S. Application Data

(63) Continuation of application No. 09/935,280, filed on Aug. 21, 2001, now Pat. No. 6,916,632.

(60) Provisional application No. 60/226,563, filed on Aug. 21, 2000.

(51) Int. Cl.
C07H 21/02 (2006.01)
C07H 21/04 (2006.01)
C12N 15/00 (2006.01)
C12Q 1/68 (2006.01)

(52) U.S. Cl. .................... 536/23.1; 536/23.2; 435/320.1

(58) Field of Classification Search ........................ None
See application file for complete search history.

(56) References Cited

U.S. PATENT DOCUMENTS 4,661,450 A 4/1987 Kempe et al.

(Continued)

FOREIGN PATENT DOCUMENTS

EP 0 373 914 A2 12/1989

(Continued)

OTHER PUBLICATIONS

Bethke, B. et al., Nucl. Acids Res., vol. 25, pp. 2828-2834 (1997).*

(Continued)

*Primary Examiner*—Teresa E Strzelecka
(74) *Attorney, Agent, or Firm*—Life Technologies Corporation; Peter G. Foiles

(57) ABSTRACT

The present invention provides compositions, methods, and kits for covalently linking nucleic acid molecules. The methods include a strand invasion step, and the compositions and kits are useful for performing such methods. For example, a method of covalently linking double stranded (ds) nucleic acid molecules can include contacting a first ds nucleic acid molecule, which has a topoisomerase linked to a 3' terminus of one end and has a single stranded 5' overhang at the same end, with a second ds nucleic acid molecule having a blunt end, such that the 5' overhang can hybridize to a complementary sequence of the blunt end of the second nucleic acid molecule, and the topoisomerase can covalently link the ds nucleic acid molecules. The methods are simpler and more efficient than previous methods for covalently linking nucleic acid sequences, and the compositions and kits facilitate practicing the methods, including methods of directionally linking two or more ds nucleic acid molecules.

10 Claims, 17 Drawing Sheets

U.S. PATENT DOCUMENTS

| | | | |
|---|---|---|---|
| 4,800,159 | A | 1/1989 | Mullis et al. |
| 5,624,826 | A | 4/1997 | Kato et al. |
| 5,766,891 | A * | 6/1998 | Shuman .................. 435/91.41 |
| 5,827,704 | A * | 10/1998 | Cease et al. ................ 435/91.2 |
| 5,958,681 | A | 9/1999 | Wetmur et al. |
| 6,013,440 | A | 1/2000 | Lipshutz et al. |
| 6,140,086 | A * | 10/2000 | Fox et al. ................. 435/91.41 |
| 6,238,884 | B1 * | 5/2001 | Short et al. ................ 435/69.1 |
| 6,277,632 | B1 | 8/2001 | Harney |
| 6,280,977 | B1 | 8/2001 | Liang et al. |
| 6,291,213 | B1 | 9/2001 | Rothstein |
| 6,340,595 | B1 | 1/2002 | Vogels et al. |
| 6,537,776 | B1 * | 3/2003 | Short ........................ 435/69.1 |
| 6,548,277 | B1 * | 4/2003 | Shuman ..................... 435/91.4 |
| 6,825,011 | B1 * | 11/2004 | Romantchikov ......... 435/91.41 |
| 2001/0044137 | A1 * | 11/2001 | Heyman et al. ............ 435/91.1 |
| 2002/0025561 | A1 * | 2/2002 | Hodgson ................... 435/91.1 |
| 2002/0028444 | A1 | 3/2002 | Harney et al. |
| 2002/0068290 | A1 | 6/2002 | Yarovinsky |
| 2002/0182731 | A1 * | 12/2002 | Ji et al. ....................... 435/455 |

FOREIGN PATENT DOCUMENTS

| | | |
|---|---|---|
| EP | 0373914 | 12/1989 |
| EP | 0 625 572 A1 | 9/1993 |
| EP | 0625572 | 9/1993 |
| WO | 85/04898 | 11/1985 |
| WO | WO-85/04898 | 11/1985 |
| WO | 94/29443 | 12/1994 |
| WO | WO-94/29443 | 12/1994 |
| WO | 96/19497 | 6/1996 |
| WO | WO-96/19497 | 6/1996 |
| WO | 96/34981 | 11/1996 |
| WO | WO-96/34981 | 11/1996 |
| WO | 97/24455 | 7/1997 |
| WO | WO-97/24455 | 7/1997 |
| WO | WO 97/48716 | 12/1997 |
| WO | WO-97/48716 | 12/1997 |
| WO | 98/20122 | 5/1998 |
| WO | WO-98/20122 | 5/1998 |
| WO | 98/55502 | 12/1998 |
| WO | 98/56943 | 12/1998 |
| WO | WO-98/55502 | 12/1998 |
| WO | WO-98/56943 | 12/1998 |
| WO | WO-00/12687 | 3/2000 |
| WO | WO 00/12687 | 3/2000 |
| WO | 00/56878 | 9/2000 |
| WO | WO-00/56878 | 9/2000 |
| WO | WO-01/62892 | 8/2001 |
| WO | WO 01/62892 A2 | 8/2001 |

OTHER PUBLICATIONS

Carninci, et al., "High Efficiency Selection of full-length cDNA by Improved Biotinylated Cap Trapper", DNA Research, 4, Universal Academy Press,(1997),61-66.

Carninci, et al., "High-Efficiency Full-Length cDNA Cloning by Biotinylated CAP Trapper", Genomics, 37(3), Academic Press, Inc., (1996),327-36.

Cheng, et al., "A catalytic domain of eukaryotic DNA topoisomerase I", J. Biol. Chem. 273(19), The American Society for Biochemistry and Molecular Biology, Inc.,(1988),11589-11595.

Cheng, et al., "Conservation of structure and mechanism between eukaryotic topoisomerase I and site-specific recombinases", Cell 92(6), Cell Press,(1998),841-850.

Cheng, et al., "DNA strand transfer catalyzed by vaccinia topoisomerase: ligation of DNAs containing a 3' mononucleotide overhang", Nucleic Acids Res., 28(9), Oxford University Press,(2000),1893-1898.

Cheng, et al., "Mutational analysis of 39 residues of vaccinia DNA topoisomerase identifies Lys-220, Arg-223, and Asn-228 as important for covalent catalysis", J. Biol. Chem. 272(13), The American society for Biochemistry and Molecular Biology, Inc.,(1997),8263-8269.

Cheng, et al., "Recombinogenic flap ligation pathway for intrinsic repair of topoisomerase IB-induced double-strand breaks", Mol. Cell. Biol. 20(21), American Society for Microbiology,(2000),8059-8068.

Cheng, et al., "Site-specific DNA transesterification by vaccinia topoisomerase: Role of specific phosphates and nucleosides", Biochemistry 38(50), American Chemical Society,(1999),16599-16612.

Digate, et al., "Molecular Cloning and DNA Sequence Analysis of Escherichia coli topB, the Gene Encoding Topoisomerase III", J. Biol. Chem. 264(30), The American society for Biochemistry and Molecular Biology, Inc.,(1989),17924-17930.

Edery, et al., "An Efficient Strategy to Isolate Full-Length cDNAs Based on an mRNA Cap Retention Procedure (CAPture)", Mol. Cell. Biol., 15(6), American Society for Microbiology,(1995),3363-3371.

Ericsson, et al., "Characterization of ts 16, a temperature-sensitive mutant of vaccinia virus", J. Virol.. 69(11), American Society for Microbiology,(1995),7072-7086.

Gross, et al., "Vaccinia virions lacking the RNA helicase nucleoside triphosphate phosphohydrolase II are defective in early transcription", J. Virol. 70(12), American Society for Microbiology,(1996),8549-8555.

Haghighat, et al., "eIF4G Dramatically Enhances the Binding of eIF4E to the mRNA 5'-Cap Structure", J. Biol. Chem., 272(35), The American society for Biochemistry and Molecular Biology, Inc., (1997),21677-21680.

Haghighat, et al., "The eIF4G-eIF4E Complex is the Target for Direct Cleavage by the Rhinovirus 2A Proteinase", J. Virol. 70, American Society for Microbiology,(1996),8444-8450.

Henningfeld, et al., "A model for topoisomerase I-mediated insertions and deletions with duplex DNA substrates containing branches, nicks, and gaps", Biochemistry 34(18), American Chemical Society,(1995),6120-6129.

Heyman, et al., "Genome Scale Cloning and Expression of individual Open Reading Frames Using Topoisomerase I-Mediated Ligation", Genome Research,(1999),383-392.

Invitrogen Corporation, "Invitrogen Catalog, Carlsbad, California", (1998),18, 29, 43, 44, 49-52.

Janknecht, et al., "Rapid and efficient purification of native histidine-tagged protein expressed by recombinant vaccina virus", Proc. Natl. Acad. Sci., U S A 88, National Academic of Sciences,(1991),8972-8976.

Kane, et al., "Vaccinia virus morphogenesis is blocked by temperature-sensitive mutation in the 17 gene that encodes a virion component", J. Virol. 67(5), American Society for Microbiology,(1993),2689-2698.

Kato, et al., "Construction of a Human Full-Length cDNA Bank", Gene 150, Elsevier Science,(1994),243-250.

Klemm, et al., "Peptide inhibitors of DNA cleavage by tyrosine recombinases and topoisomerases", J. Mol. Biol. 299(5), Academic Press, Inc.,(2000), 1203-1216.

Klemperer, et al., "Identification and characterization of the orf virus type I topoisomerase", Virology 206, Academic Press, Inc., (1995),203-215.

Krogh, "Vaccinia topoisomerase mutants illuminate conformational changes during closure of the protein clamp and assembly of a functional active site", J. Biol. Chem., The American Society for Biochemistry and Molecular Biology, Inc.,(Jul. 5, 2001),Manuscript.

Krogh, et al., "Catalytic mechanism of DNA topoisomerase IB", Mol. Cell., 5(6), Cell Press,(2000),1035-1041.

Krogh, et al., "DNA strand transfer catalyzed by vaccinia topoisomerase: peroxidolysis and hydroxylaminolysis of the covalent protein-DNA intermediate", Biochemistry 39(21), American Chemical Society,(2000),6422-6432.

Krogh, et al., "Effect of 2'-5' phosphodiesters on DNA transesterification by vaccinia topoisomerase", J. Biol. Chem. 276(24), The American Society for Biochemistry and Molecular Biology, Inc., (2001),20907-20912.

Krogh, et al., "Melanoplus sanguinipes entomopoxvirus DNA topoisomerase: site-specific DNA transesterification and effects of 5'-bridging phosphorothiolates", Virology 264(2), Academic Press, Inc.,(1999),441-451.

Liu, X. et al., "Mapping the 5' and 3' Ends of Tetrahymena thermophelia mRNAs Using RNA Ligase Mediated Amplification of cDNA Ends (RLM-RACE)", Nucl. Acids Res. 21, Oxford University Press,(1993),4954-4960.

Lockard, et al., "Labeling of Eukaryotic Messager RNA 5' Terminus with Phosphorus-32: Use of Tobacco Acid Pyrophosphatase for Removal of Cap Structures", Gene Amplification and Analysis 2, Elsevier Science,(1981),229-251.

Maruyama, et al., "Oligo-Capping: A Simple Method to Replace the Cap Structure of Eukaryotic mRNAs with Oligoribonucleotides", Gene. 138,(1994),171-174.

Morham, et al., "Covalent and Noncovalent DNA Binding by Mutants of Vaccinia DNA Topoisomerase I", J. Biol. Chem. 267, The American Society for Biochemistry and Molecular Biology, Inc., (1992), 15984-15992.

Morham, et al., "Phenotypic selection and characterization of mutant alleles of a eukaryotic DNA topoisomerase I", Genes. Dev. 4(4), Cold Spring Harbor Laboratory Press,(1990),515-524.

Palaniyar, et al., "SFV topoisomerase: sequence specificity in a genetically mapped interval", Virology 221, American Press, Inc., (1996),351-354.

Petersen, et al., "DNA strand transfer reactions catalyzed by vaccina topoisomerase: hydrolysis and glycerololysis of the covalent protein-DNA intermediate", Nucleic Acids Res. 25(11), Oxford University Press,(1997),2091-2097.

Petersen, et al., "Mutations within a conserved region of vaccinia topoisomerase affect the DNA cleavage-religation equilibrium", J. Mol. Biol. 1263(2), Academic Press Limited,(1996), 181-195.

Peterson, et al., "Histidine 265 is important for covalent catalysis by vaccinia topoisomerase and is conserved in all eukaryotic tyoe I enzymes", J. Biol. Chem. 272(7), The American Society for Biochemistry and Molecular Biology, Inc.,(1997),3891-3896.

Salazar, et al., "The DNA strand in DNA.RNA hybrid duplexes is neither B-form nor A-form in solution", Biochemistry 32(16), American Chemical Society,(1993),4207-4215.

Schmitt, et al., "Affinity purification of histidine-tagged proteins", Molecular Biology Reports 18,(1993),223-230.

Sekiguchi, et al., "Covalent DNA binding by vaccinia topoisomerase results in unpairing of the thymine base 5' of the scissile bond", and Shuman, "," J. Biol. Chem. 271(32), The American Society for Biochemistry and Molecular Biology, Inc.,(1996),19436-19442.

Sekiguchi, et al., "Domain structure of vaccinia DNA ligase", Nucleic Acids Res. 25(4), Kluwer Academic Publishers,(1997),727-734.

Sekiguchi, et al., "Identification of contacts between topoisomerase I and its target DNA by site-specific photocrosslinking", EMBO J. 15(13), Oxford University Press,(1996),3448-3457.

Sekiguchi, et al., "Kinetic analysis of DNA and RNA strand transfer reactions catalyzed by vaccinia topoisomerase", J. Biol. Chem., 272(25,The American Society for Biochemistry and Molecular Biology, Inc.,(1997),15721-15728.

Sekiguchi, et al., "Mechanism of inhibition of vaccinia DNA topoisomerase by novobiocin and coumermycin", J. Biol. Chem. 271(4), The American Society for Biochemistry and Molecular Biology, Inc.,(1996),2313-2322.

Sekiguchi, et al., "Mutational analysis of vaccinia virus topoisomerase identifies residues involved in DNA binding", Nucleic Acids Res., 25(18), Oxford University Press,(1997),3649-3656.

Sekiguchi, et al., "Nick sensing by vaccinia virus DNA ligase requires a 5'phosphate at the nick and occupancy of the adenylate binding site on the enzyme", J. Virol. 71(12), American Society for Microbiology,(1997),9679-9684.

Sekiguchi, et al., "Proteolytic footprinting of vaccinia topoisomerase bound to DNA", J. Biol. Chem., 270(19), The American Society for Biochemistry and Molecular Biology, Inc.,(1995),11636-11645.

Sekiguchi, et al., "Requirements for noncovalent binding of vaccinia topoisomerase I to duplex DNA", Nucleic Acids Res. 22(24), Oxford University Press,(1994),5360-5365.

Sekiguchi, et al., "Resolution of a Holliday junction by vaccinia topoisomerase requires a spacer DNA segment 3' of the CCCTT/ cleavage sites", Nucleic Acids Res. 28(14), Oxford University Press,(2000),2658-2663.

Sekiguchi, et al., "Resolution of Holliday junctions by eukaryotic DNA topoisomerase I", Proc. Natl. Acad. Sci. U S A. 93(2), National Academy of Sciences,(1996),785-789.

Sekiguchi, et al., "Site-specific ribonuclease activity of eukaryotic DNA topoisomerase I", Mol. Cell. 1(1), Cell Press,(1997),89-97.

Sekiguchi, et al., "Stimulation of vaccinia topoisomerase I by nucleoside triphosphates", J. Biol. Chem. 269(47), The American Society for Biochemistry and Molecular Biology, Inc.,(1994),29760-29764.

Sekiguchi, et al., "Vaccinia topoisomerase binds circumferentially to DNA", J. Biol. Chem. 269(50), The American Society for Biochemistry and Molecular Biology, Inc.,(1994),31731-31734.

Shuman, "Analysis of topoisomerase-DNA interactions by electrophoretic mobility shift assay", Methods Mol. Biol. 95, Hunana Press, Inc.,(2001),65-74.

Shuman, "Polynucleotide ligase activity of eukaryotic topoisomerase I", Mol. Cell. 1(5), Cell Press,(1998),741-748.

Shuman, "Site-specific DNA cleavage by vaccinia virus DNA topoisomerase I. Role of nucleotide sequence and DNA secondary structure", J. Biol. Chem.. 266, The American Society for Biochemistry and Molecular Biology, Inc.,(1991),1796-1803.

Shuman, "Two Classes of DNA End-Joining Reactions Catalyzed by Vaccinia Topoisomerase I", J. Biol. Chem.. 267, The American Society for Biochemistry and Molecular Biology, Inc.,(1992),16755-16758.

Shuman, "Vaccinia DNA topoisomerase I promotes illegitimate recombination in *Escherchia coli*", Proc. Natl. Acad. Sci. U S A. 86(10), National Academic of Sciences,(1989),3489-3493.

Shuman, "Vaccinia virus DNA ligase: specificity, fidelity, and inhibition", Biochemistry 34, American Chemical Society,(1995),16138-16147.

Shuman, "Vaccinia virus DNA topoisomerase: a model eukaryotic type IB enzyme", Biochim. Biophys. Acta. 1400(1-3), Elsevier Science,(1998),321-337.

Shuman, et al., "Identification of a Vaccinia Virus Gene Encoding a Type I DNA Topoisomerase", Proc. Natl. Acad. Sci., U S A 84, National Academic of Sciences,(1987),7478-7482.

Shuman, et al., "Insertional mutagenesis of the vaccinia virus gene encoding a type I DNA topoisomerase: evidence that the gene is essential for virus growth", Virology. 170(1), Academic Press, Inc., (1989),302-36.

Shuman, et al., "Intramolecular synapsis of duplex DNA by vaccinia topoisomerase", EMBO J. 16(21), Oxford University Press,(1997),6584-6589.

Shuman, et al., "Mapping the active-site tyrosine of vaccinia virus DNA topoisomerase I", Proc. Natl. Acad. Sci. U S A. 86(24), National Academic of Sciences,(1989),9793-9797.

Shuman, et al., "Site-specific interaction of vaccinia virus topoisomerase I with base and sugar moieties in duplex DNA", J. Biol. Chem. 268(25), The American Society for Biochemistry and Molecular Biology, Inc.,(1993),18943-18950.

Shuman, et al., "Specific DNA Cleavage and Binding of Vaccinia Virus DNA Topoisomerase I", J. Biol. Chem.. 265, The American Society for Biochemistry and Molecular Biology, Inc.,(1990),17826-17836.

Shuman, S. "Novel Approach to molecular cloning and polynucleotide synthesis using vaccinia DNA topoisomerase", J. of Biol. Chem., US, vol. 269(51),(Dec. 23, 1994),32678-32684.

Shuman, S. "Recombination mediated by vaccinia virus DNA topoisomerase I in *Escherichia coli* is sequence specific", Proc. Natl. Acad. Sci. USA 88, National Academy of Sciences,(1991),10104-10108.

Shuman, S. "Site-specific interaction of Vaccinia Virus Topoisomerase I with Duplex DNA. Minimal DNA Substrate for Strand Cleavage In Vitro,", J. Biol. Chem. 266, The American Society for Biochemistry and Molecular Biology, Inc.,(1991),11372-11379.

Shuman, S. et al., "Characterization of Vaccinia Virus DNA Topoisomerase I Expressed in *Escherica coli*", J. Biol. Chem. 263, The American Society for Biochemistry and Molecular Biology, Inc.,(1988),16401-16407.

Stivers, et al., "Stereochemical outcome and kinetic effects of Rp- and Sp- phosphorothioate substitution at the cleavage site of vaccinia type I DNA topoisomerase", , et al.,"," Biochemistry 39(18):. () American Chemical Society,(2000),5562-5572.

Stivers, et al., "Vaccinia DNA topoisomerase I: kinetic evidence for general acid-base catalysis and a coformational step", Biochemistry 33(51), American Chemical Society,(1994),15449-15458.

Stivers, et al., "Vaccinia DNA topoisomerase I: single-turnover and steady-state kinetic analysis of the DNA strand cleavage ligation reactions", Biochemistry 33(1), American Chemical Society,(1994),327-339.

Wang, et al., "Deletions at the carboxyl terminus of vaccinia DNA topoisomerase affect DNA binding and enhance distributivity in DNA relaxation", Biochemistry 36(13), American Chemical Society,(1997),3909-3916.

Wang, et al., "Mutational analysis of 26 residues of vaccinia DNA topoisomerase identifies Ser-204 as important for DNA binding and cleavage", Biochemistry 36(26), American Chemical Society,(1997),7944-7950.

Wexler, et al., "A Procedure to Amplify cDNA from dsRNA Templates Using the Polymerase Chain Reaction", Methods in Molecular and Cellular Biology 2,(1991),273-279.

Wittschieben, et al., "Mechanism of DNA transesterification by vaccinia topoisomerase: catalytic contributions of essential residues Arg-130, Gly-132, Tyr-136 and Lys-167", Nucleic Acids Res. 25(15), Oxford University Press,(1997),3001-3008.

Wittschieben, et al., "Mutational analysis of vaccinia DNA topoisomerase defines amino acid residues essential for covalent catalysis", J. Biol. Chem. 269(47), The American Society for Biochemistry and Molecular Biology, Inc.,(1994),29978-29983.

Wittschieben, et al., "Replacement of the active site tyrosine of vaccinia DNA topoisomerase by glutamate, cysteine of histidine converts the enzyme into a site-specific endonuclease", Nucleic Acids Res. 26(2), Oxford University Press,(1998),490-496.

Woodfield, et al., "Vaccinia topoisomerase and Cre recombinase catalyze direct ligation of activated DNA substrates containing 3'-para-nitrophenyl phosphate ester", Nucleic Acids Res. 28(17), Oxford University Press,(2000),3323-3331.

Yang, et al., "A eukaryotic enzyme that can disjoin dead-end covalent complexes between DNA and type I topoisomerases", Proc. Natl. Acad. Sci. U S A. 93(21), National Academic of Sciences,(1996),11534-11539.

Liu, et al., "Mapping the 5' and 3' Ends of Tetrahymena thermophila mRNAs Using RNA Ligase Mediated Amplification of cDNA Ends ( RLM-RACE)," *Nucleic Acids Research* 21(21): 4954-4960. (1993) The Oxford University Press.

Lockard, et al., "Labeling of Eukaryotic Messenger RNA 5' Terminus with Phosphorus-32: Use of Tobacco Acid Pyrophosphatase for Removal of Cap Structures," *Gene Amplification and Analysis* 2:229-251. (1981) Elsevier Science.

Wexler, et al., "A Procedure to Amplify cDNA from dsRNA Templates Using the Polymerase Chain Reaction," *Methods in Molecular and Cellular Biology* 2:273-279 (1991).

Heyman et al., "Genome-Scale Cloning and Expression of Individual Open Reading Frames Using Topoisomerase I-Mediated Ligation," *Genome Research*, pp. 383-392 (1999).

Carninci, et al. "High-Efficiency Full-Length cDNA Cloning by Biotinylated CAP Trapper," *Genomics*, 37(3):327-36 (1996) Academic Press, Inc.

Carninci, et al. "High Efficiency Selection of full-length cDNA by Improved Biotinylated Cap Trapper," *DNA Research*, 4:61-66 (1997). Universal Academy Press.

Cheng and Shuman, "DNA strand transfer catalyzed by vaccinia topoisomerase: ligation of DNAs containing a 3' mononucleotide overhang," *Nucleic Acids Res.*, 28(9):1893-8. (2000). Oxford University Press.

Cheng and Shuman, "Recombinogenic flap ligation pathway for intrinsic repair of topoisomerase IB-induced double-strand breaks," *Mol. Cell. Biol.* 20(21):8059-8068 (2000) American Society for Microbiology.

Cheng and Shuman, "Site-specific DNA transesterification by vaccinia topoisomerase: Role of specific phosphates and nucleosides," *Biochemistry* 38(50):16599-612 (1999) American Chemical Society.

Cheng and Shuman, "A catalytic domain of eukaryotic DNA topoisomerase I," *J. Biol. Chem.* 273(19):11589-95 (1998) The American Society for Biochemistry and Molecular Biology, Inc.

Cheng, et al., "Conservation of structure and mechanism between eukaryotic topoisomerase I and site-specific recombinases," *Cell.* 92(6):841-50 (1998) Cell Press.

Cheng, et al., "Mutational analysis of 39 residues of vaccinia DNA topoisomerase identifies Lys-220, Arg-223, and Asn-228 as important for covalent catalysis," *J. Biol. Chem.* 272(13):8263-9 (1997) The American society for Biochemistry and Molecular Biology, Inc.

DiGate and Marians, "Molecular Cloning and DNA Sequence Analysis of *Escherichia coli topB*, the Gene Encoding Topoisomerase III," *J. Biol. Chem.* 264(30):17924-17930 (1989). The American society for Biochemistry and Molecular Biology, Inc.

Edery, et al., "An Efficient Strategy to Isolate Full-Length cDNAs Based on an mRNA Cap Retention Procedure (CAPture)," *Mol. Cell. Biol.*, 15(6):3363-3371 (1995). American Society for Microbiology.

Ericsson, et al., "Characterization of ts 16, a temperature-sensitive mutant of vaccinia virus," *J. Virol..* 69(11):7072-86 (1995) American Society for Microbiology.

Gross and Shuman, "Vaccinia virions lacking the RNA helicase nucleoside triphosphate phosphohydrolase II are defective in early transcription," *J. Virol.* 70(12):8549-5 (1996) American Society for Microbiology.

Haghighat and Sonenberg, "eIF4G Dramatically Enhances the Binding of eIF4E to the mRNA 5'-Cap Structure," *J. Biol. Chem.*, 272(35):21677-21680 (1997). The American society for Biochemistry and Molecular Biology, Inc.

Haghighat et al., "The eIF4G-eIF4E Complex is the Target for Direct Cleavage by the Rhinovirus 2A Proteinase," *J. Virol.* 70:8444-8450 (1996). American Society for Microbiology.

Henningfeld and Hecht, "A model for topoisomerase I-mediated insertions and deletions with duplex DNA substrates containing branches, nicks, and gaps," *Biochemistry* 34(18):6120-9. (1995) American Chemical Society.

Invitrogen Corporation. *Invitrogen Catalog*, Carlsbad, California, pp. 18, 29, 43, 44, 49-52 (1998).

Janknecht, et al., "Rapid and efficient purification of native histidine-tagged protein expressed by recombinant vaccinia virus," *Proc. Natl. Acad. Sci., U S A* 88:8972-8976(1991) National Academic of Sciences.

Kane and Shuman, "Vaccinia virus morphogenesis is blocked by a temperature-sensitive mutation in the I7 gene that encodes a virion component," *J. Virol.* 67(5):2689-98 (1993) American Society for Microbiology.

Kato, et al., "Construction of a Human Full-Length cDNA Bank," *Gene.* 150: 243-250 (1994) Elsevier Science.

Klemm, et al., "Peptide inhibitors of DNA cleavage by tyrosine recombinases and topoisomerases," *J. Mol. Biol.* 299(5):1203-16. (2000) Academic Press, Inc.

Klemperer, et al., "Identification and characterization of the orf virus type I topoisomerase," *Virology* 206:203-215 (1995) Academic Press, Inc.

Krogh and Shuman, "Vaccinia topoisomerase mutants illuminate conformational changes during closure of the protein clamp and assembly of a functional active site," *J. Biol. Chem.* Jul. 5, 2001 [Manuscript] The American Society for Biochemistry and Molecular Biology, Inc.

Krogh and Shuman, "Catalytic mechanism of DNA topoisomerase IB," *Mol. Cell..* 5(6):1035-41 (2000) Cell Press.

Krogh and Shuman, "DNA strand transfer catalyzed by vaccinia topoisomerase: peroxidolysis and hydroxylaminolysis of covalent protein-DNA intermediate," *Biochemistry* 39(21):6422-32. (2000) American Chemical Society.

Krogh, et al., "Effect of 2'-5' phosphodiesters on DNA transesterification by vaccinia topoisomerase," *J. Biol. Chem.* 276(24):20907-20912. (2001) The American Society for Biochemistry and Molecular Biology, Inc.

Krogh, et al., Melanoplus sanguinipes entomopoxvirus DNA topoisomerase: site-specific DNA transesterification and effects of 5'-bridging phosphorothiolates, *Virology* 264(2):441-51. (1999) Academic Press, Inc.

Maruyama and Sugano, "Oligo-Capping: A Simple Method to Replace the Cap Structure of Eukaryotic mRNAs with Oligoribonucleotides," *Gene.* 138:171-174 (1994).

Morham and Shuman, "Covalent and Noncovalent DNA Binding by Mutants of Vaccinia DNA Topoisomerase I," *J. Biol. Chem.* 267:15984-15992 (1992) The American Society for Biochemistry and Molecular Biology, Inc.

Morham and Shuman, "Phenotypic selection and characterization of mutant alleles of a eukaryotic DNA topoisomerase I," *Genes. Dev.* 4(4):515-24 (1990) Cold Spring Harbor Laboratory Press.

Palaniyar, et al., "SFV topoisomerase: sequence specificity in a genetically mapped interval," *Virology* 221:351-354 (1996). American Press, Inc.

Petersen and Shuman, "DNA strand transfer reactions catalyzed by vaccinia topoisomerase: hydrolysis and glycerolysis of the covalent protein-DNA intermediate," *Nucleic Acids Res.* 25(11):2091-7 (1997) Oxford University Press.

Petersen and Shuman, "Histidine 265 is important for covalent catalysis by vaccinia topoisomerase and is conserved in all eukaryotic type I enzymes," *J. Biol. Chem.* 272(7):3891-6 (1997) The American Society for Biochemistry and Molecular Biology, Inc.

Petersen et al., "Characterization of a DNA topoisomerase encoded by Amsacta moore entomopoxvirus," *Virology* 230(2):197-206 (1997) Academic Press, Inc.

Petersen, et al., "Mutations within a conserved region of vaccinia topoisomerase affect the DNA cleavage-religation equilibrium," *J. Mol. Biol.* 1263(2):181-95 (1996) Academic Press Limited.

Salazar et al., "The DNA strand in DNA.RNA hybrid duplexes is neither B-form nor A-form in solution," *Biochemistry* 32(16):4207-15 (1993) American Chemical Society.

Schmitt, et al., "Affinity purification of histidine-tagged proteins," *Molecular Biology Reports* 18:223-230 (1993).

Sekiguchi and Shuman, "Domain structure of vaccinia DNA ligase," *Nucleic Acids Res.* 25(4):727-34 (1997) Kluwer Academic Publishers.

Sekiguchi and Shuman, "Mutational analysis of vaccinia virus topoisomerase identifies residues involved in DNA binding," *Nucleic Acids Res.* 25(18):3649-56. (1997) Oxford University Press.

Sekiguchi and Shuman, "Nick sensing by vaccinia virus DNA ligase requires a 5' phosphate at the nick and occupancy of the adenylate binding site on the enzyme," *J. Virol.* 71(12):9679-84 (1997) American Society for Microbiology.

Sekiguchi and Shuman, "Site-specific ribonuclease activity of eukaryotic DNA topoisomerase I," *Mol. Cell.* 1(1):89-97.(1997) Cell Press.

Sekiguchi and Shuman, "Covalent DNA binding by vaccinia topoisomerase results in unpairing of the thymine base 5' of the scissile bond," *J. Biol. Chem.* 271(32):19436-42 (1996). The American Society for Biochemistry and Molecular Biology, Inc.

Sekiguchi and Shuman, "Identification of contacts between topoisomerase I and its target DNA by site-specific photocrosslinking," *EMBO J.* 15(13):3448-57 (1996) Oxford University Press.

Sekiguchi and Shuman, "Proteolytic footprinting of vaccinia topoisomerase bound to DNA," *J. Biol. Chem.* 270(19):11636-45 (1995) The American Society for Biochemistry and Molecular Biology, Inc.

Sekiguchi and Shuman, "Requirements for noncovalent binding of vaccinia topoisomerase I to duplex DNA," *Nucleic Acids Res.* 22(24):5360-5 (1994) Oxford University Press.

Sekiguchi and Shuman, "Stimulation of vaccinia topoisomerase I by nucleoside triphosphates," *J. Biol. Chem.* 269(47):29760-4 (1994) The American Society for Biochemistry and Molecular Biology, Inc.

Sekiguchi and Shuman, "Vaccinia topoisomerase binds circumferentially to DNA," *J. Biol. Chem.* 269(50):31731-4 (1994) The American Society for Biochemistry and Molecular Biology, Inc.

Sekiguchi, et al., "Resolution of a Holliday junction by vaccinia topoisomerase requires a spacer DNA segment 3' of the CCCTT/ cleavage sites," *Nucleic Acids Res.* 28(14):2658-63. (2000) Oxford University Press.

Sekiguchi, et al., "Kinetic analysis of DNA and RNA strand transfer reactions catalyzed by vaccinia topoisomerase," *J. Biol. Chem..* 272(25):15721-8 (1997) The American Society for Biochemistry and Molecular Biology, Inc.

Sekiguchi, et al., "Mechanism of inhibition of vaccinia DNA topoisomerase by novobiocin and coumermycin," *J. Biol. Chem.* 271(4):2313-22 (1996) The American Society for Biochemistry and Molecular Biology, Inc.

Sekiguchi, et al., "Resolution of Holliday junctions by eukaryotic DNA topoisomerase I," *Proc. Natl. Acad. Sci. U S A.* 93(2):785-9. (1996) National Academic of Sciences.

Shuman, "Analysis of topoisomerase-DNA interactions by electrophoretic mobility shift assay," *Methods Mol. Biol.* 95:65-74(2001) Hunana Press, Inc.

Shuman, "Polynucleotide ligase activity of eukaryotic topoisomerase i," *Mol. Cell.* 1(5):741-8. (1998) Cell Press.

Shuman, "Vaccinia virus DNA topoisomerase: a model eukaryotic type IB enzyme," *Biochim. Biophys. Acta.* 1400(1-3):321-37. (1998) Elsevier Science.

Shuman, "Vaccinia virus DNA ligase: specificity, fidelity, and inhibition," *Biochemistry* 34:16138-16147 (1995) American Chemical Society.

Shuman, "Novel approach to molecular cloning and polynucleotide synthesis using vaccinia DNA topoisomerase" *J. Biol. Chem..* 269(51):32678-32684 (1994).

Shuman, "DNA Strand Transfer Reactions Catalyzed by Vaccinia Topoisomerase I", *J. Biol. Chem.* 267:8620-8627. (1992) The American Society for Biochemistry and Molecular Biology, Inc.

Shuman, "Two Classes of DNA End-Joining Reactions Catalyzed by Vaccinia Topoisomerase I", *J. Biol. Chem..* 267:16755-16758. (1992) The American Society for Biochemistry and Molecular Biology, Inc.

Shuman, "Recombination mediated by vaccinia virus DNA topoisomerase I in *Escherichia coli* is sequence specific," *Proc. Natl. Acad. Sci. U S A.* 88(22):10104-8 (1991) National Academic of Sciences.

Shuman, "Site-specific DNA cleavage by vaccinia virus DNA topoisomerase I. Role of nucleotide sequence and DNA secondary structure," *J. Biol. Chem..* 266(3):1796-1803. (1991) The American Society for Biochemistry and Molecular Biology, Inc.

Shuman, "Site-specific interaction of vaccinia virus topoisomerase I with duplex DNA. Minimal DNA substrate for strand cleavage in vitro," *J. Biol. Chem.* 266(17):11372-11379 (1991) The American Society for Biochemistry and Molecular Biology, Inc.

Shuman, "Vaccinia DNA topoisomerase I promotes illegitimate recombination in *Escherichia coli*," *Proc. Natl. Acad. Sci. U S A.* 86(10):3489-93 (1989) National Academic of Sciences.

Shuman and Moss, "Identification of a Vaccinia Virus Gene Encoding a Type I DNA Topoisomerase," *Proc. Natl. Acad. Sci., U S A* 84:7478-7482. (1987) National Academic of Sciences.

Shuman and Prescott. "Specific DNA Cleavage and Binding of Vaccinia Virus DNA Topoisomerase I" *J. Biol. Chem..* 265:17826-17836. (1990) The American Society for Biochemistry and Molecular Biology, Inc.

Shuman and Turner, "Site-specific interaction of vaccinia virus topoisomerase I with base and sugar moieties in duplex DNA," *J. Biol. Chem.* 268(25):18943-50 (1993) The American Society for Biochemistry and Molecular Biology, Inc.

Shuman, et al., "Intramolecular synapsis of duplex DNA by vaccinia topoisomerase," *EMBO J.* 16(21):6584-9 (1997) Oxford University Press.

Shuman, et al., "Insertional mutagenesis of the vaccinia virus gene encoding a type I DNA topoisomerase: evidence that the gene is essential for virus growth," *Virology.* 170(1):302-6 (1989) Academic Press, Inc.

Shuman, et al., "Mapping the active-site tyrosine of vaccinia virus DNA topoisomerase I," *Proc. Natl. Acad. Sci. U S A.* 86(24):9793-7 (1989) National Academic of Sciences.

Shuman, et al., "Characterization of Vaccinia Virus DNA Topoisomerase I Expressed in *Escherichia coli*", *J. Biol. Chem.*. 263:16401-16407. (1988) The American Society for Biochemistry and Molecular Biology, Inc.

Stivers, et al., "Stereochemical outcome and kinetic effects of Rp- and Sp- phosphorothioate substitutions at the cleavage site of vaccinia type I DNA topoisomerase," *Biochemistry* 39(18):5561-72. (2000) American Chemical Society.

Stivers et al., "Vaccinia DNA topoisomerase I: kinetic evidence for general acid-base catalysis and a conformational step," *Biochemistry* 33(51):15449-58 (1994) American Chemical Society.

Stivers, et al., "Vaccinia DNA topoisomerase I: single-turnover and steady-state kinetic analysis of the DNA strand cleavage and ligation reactions," *Biochemistry* 33(1):327-39 (1994) American Chemical Society.

Wang and Shuman, "Deletions at the carboxyl terminus of vaccinia DNA topoisomerase affect DNA binding and enhance distributivity in DNA relaxation," *Biochemistry* 36(13):3909-16 (1997) American Chemical Society.

Wang, et al., "Mutational analysis of 26 residues of vaccinia DNA topoisomerase identifies Ser-204 as important for DNA binding and cleavage," *Biochemistry* 36(26):7944-50 (1997) American Chemical Society.

Wittschieben and Shuman, "Mechanism of DNA transesterification by vaccinia topoisomerase: catalytic contributions of essential residues Arg-130, Gly-132, Tyr-136 and Lys-167," *Nucleic Acids Res.* 25(15):3001-8. (1997) Oxford University Press.

Wittschieben and Shuman, "Mutational analysis of vaccinia DNA topoisomerase defines amino acid residues essential for covalent catalysis," *J. Biol. Chem.* 269(47):29978-83 (1994) The American Society for Biochemistry and Molecular Biology, Inc.

Wittschieben, et al., "Replacement of the active site tyrosine of vaccinia DNA topoisomerase by glutamate, cysteine or histidine converts the enzyme into a site-specific endonuclease," *Nucleic Acids Res.* 26(2):490-6. (1998) Oxford University Press.

Woodfield, et al., "Vaccinia topoisomerase and Cre recombinase catalyze direct ligation of activated DNA substrates containing a 3'-para-nitrophenyl ester," *Nucleic Acids Res.* 28(17):3323-31 (2000) Oxford University Press.

Yang, et al., "A eukaryotic enzyme that can disjoin dead-end covalent complexes between DNA and type I topoisomerases," *Proc. Natl. Acad. Sci. U S A.* 93(21):11534-9 (1996) National Academic of Sciences.

* cited by examiner

MULTIPLE CLONING SITE

```
                        Uni1 Forward priming site
351    GAGCTTAGTA CGTACTATCA ACAGGTTGAA CTGCTGATCA ACAGATCCTC Kpn I                      loxP site
401    TACGCGGCCG CGGTACC ATA ACT TCG TAT AGC ATA CAT TAT ACG RBS      Xho I RBS EcoR I   Age I         Bgl I
445    AAG TTA TCG GAGGAAT TGGCTCGAGG AATTCACCGG TGCCGTGTGG BamH I    Apa I  Aat II Stu.I    Pvu I    Sac I
491    GCGGATCCGG GCCCGACGTC AGGCCT CGAT CGG AG CTC GGT AAG CCT
                                                    Gly Lys Pro V5 epitope
538    ATC CCT AAC CCT CTC CTC GGT CTC GAT TCT AGC CAT CAT
       Ile Pro Asn Pro Leu Leu Gly Leu Asp Ser Ser His His 6xHis tag         Uni1 Reverse priming site
577    CAC CAT CAC CAT TGA AGCTCGCTA TCAGCCTCGA CTGTGCCTTC
       His His His His ***

621    TAGTTGCCAG CCATCTGTTG TTTGCCCCTC CCCCGTGCCT
```

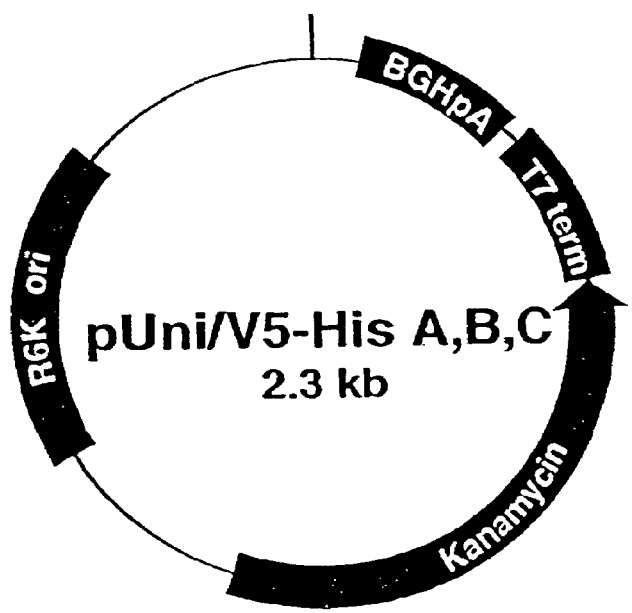

FIGURE 3

Sequence of pUni/V5-His version A

```
AATTCCCATGTCAGCCGTTAAGTGTTCCTGTGTCACTCAAAATTGCTTTGAGAGGCTCTAAGGGCTTCTC
AGTGCGTTACATCCCTGGCTTGTTGTCCACAACCGTTAAACCTTAAAAGCTTTAAAAGCCTTATATATTC
TTTTTTTTCTTATAAAACTTAAAACCTTAGAGGCTATTTAAGTTGCTGATTTATATTAATTTTATTGTTC
AAACATGAGAGCTTAGTACGTGAAACATGAGAGCTTAGTACGTTAGCGATGAGAGCTTAGTACGTTAGCC
ATGAGGGTTTAGTTCGTTAAACATGAGAGCTTAGTACGTTAAACATGAGAGCTTAGTACGTGAAACATGA
GAGCTTAGTACGTACTATCAACAGGTTGAACTGCTGATCAACAGATCCTCTACGCGGCCGCGGTACCATA
ACTTCGTATAGCATACATTATACGAAGTTATCGGAGGAATTGGCTCGAGGAATTCACCGGTGCCGTGTGG
GCGGATCCGGGCCCGACGTCAGGCCTCGATCGGAGCTCGGTAAGCCTATCCCTAACCCTCTCCTCGGTCT
CGATTCTAGCCATCATCACCATCACCATTGAAGCTCGCTATCAGCCTCGACTGTGCCTTCTAGTTGCCAG
CCATCTGTTGTTTGCCCCTCCCCCGTGCCTTCCTTGACCCTGGAAGGTGCCACTCCCACTGTCCTTTCCT
AATAAAATGAGGAAATTGCATCGCATTGTCTGAGTAGGTGTCATTCTATTCTGGGGGGTGGGGTGGGGCA
GGACAGCAAGGGGGAGGATTGGGAAGACAATAGCAGGCATGCTGGGGATTCTAGAAGATCCGGCTGCTA
ACAAAGCCCGAAAGGAAGCTGAGTTGGCTGCTGCCACCGCTGAGCAATAACTAGCATAACCCCTTGGGG
CCTCTAAACGGGTCTTGAGGGGTTTTTTGCTGAAAGGAGGAACTATATCCGGATATCCCGGGGTGGGCGA
AGAACTCCAGCATGAGATCCCCGCGCTGGAGGATCATCCAGCCGGCGTCCCGGAAAACGATTCCGAAGC
CCAACCTTTCATAGAAGGCGGCGGTGGAATCGAAATCTCGTGATGGCAGGTTGGGCGTCGCTTGGTCGGT
CATTTCGAACCCCAGAGTCCCGCTCAGAAGAACTCGTCAAGAAGGCGATAGAAGGCGATGCGCTGCGAA
TCGGGAGCGGCGATACCGTAAAGCACGAGGAAGCGGTCAGCCCATTCGCCGCCAAGCTCTTCAGCAATA
TCACGGGTAGCCAACGCTATGTCCTGATAGCGGTCCGCCACACCCAGCCGGCCACAGTCGATGAATCCAG
AAAAGCGGCCATTTTCCACCATGATATTCGGCAAGCAGGCATCGCCATGTGTCACGACGAGATCCTCGCC
GTCGGGCATGCGCGCCTTGAGCCTGGCGAACAGTTCGGCTGGCGCGAGCCCCTGATGCTCTTCGTCCAGA
TCATCCTGATCGACAAGACCGGCTTCCATCCGAGTACGTGCTCGCTCGATGCGATGTTTCGCTTGGTGGTC
GAATGGGCAGGTAGCCGGATCAAGCGTATGCAGCCGCCGCATTGCATCAGCCATGATGGATACTTTCTCG
GCAGGAGCAAGGTGAGATGACAGGAGATCCTGCCCCGGCACTTCGCCCAATAGCAGCCAGTCCCTTCCC
GCTTCAGTGACAACGTCGAGCACAGCTGCGCAAGGAACGCCCGTCGTGGCCAGCCACGATAGCCGCGCT
GCCTCGTCCTGCAGTTCATTCAGGGCACCGGACAGGTCGGTCTTGACAAAAAGAACCGGGCGCCCCTGCG
CTGACAGCCGGAACACGGCGGCATCAGAGCAGCCGATTGTCTGTTGTGCCCAGTCATAGCCGAATAGCCT
CTCCACCCAAGCGGCCGGAGAACCTGCGTGCAATCCATCTTGTTCAATCATGCGAAACGATCCTCATCCT
GTCTCTTGATCAGATCTTGATCCCCTGCGCCATCAGATCCTTGGCGGCAAGAAAGCCATCCAGTTTACTTT
GCAGGGCTTCCCAACCTTACCAGAGGGCGCCCCAGCTGGCAATTCCGGTTCGCTTGCTGTCCATAAAACC
GCCCAGTCTAGCTATCGCCATGTAAGCCCACTGCAAGCTACCTGCTTTCTCTTTGCGCTTGCGTTTTCCCTT
GTCCAGATAGCCCAGTAGCTGACATTCATCCGGGGTCAGCACCGTTTCTGCGGACTGGCTTTCTACGTGTT
CC GCTTCCTTTAGCAGCCCTTGCGCCCTGAGTGCTTGCGGCAGCGTGAAGCT
```

FIGURE 5

Sequence of pCR 2.1

```
AGCGCCCAATACGCAAACCGCCTCTCCCCGCGCGTTGGCCGATTCATTAATGCAGCTGGCACGACAGGTT
TCCCGACTGGAAAGCGGGCAGTGAGCGCAACGCAATTAATGTGAGTTAGCTCACTCATTAGGCACCCCAG
GCTTTACACTTTATGCTTCCGGCTCGTATGTTGTGTGGAATTGTGAGCGGATAACAATTTCACACAGGAA
ACAGCTATGACCATGATTACGCCAAGCTTGGTACCGAGCTCGGATCCACTAGTAACGGCCGCCAGTGTGC
TGGAATTCGGCTTAAGCCGAATTCTGCAGATATCCATCACACTGGCGGCCGCTCGAGCATGCATCTAGAG
GGCCCAATTCGCCCTATAGTGAGTCGTATTACAATTCACTGGCCGTCGTTTTACAACGTCGTGACTGGGA
AAACCCTGGCGTTACCCAACTTAATCGCCTTGCAGCACATCCCCCTTTCGCCAGCTGGCGTAATAGCGAA
GAGGCCCGCACCGATCGCCCTTCCCAACAGTTGCGCAGCCTGAATGGCGAATGGGACGCGCCCTGTAGCG
GCGCATTAAGCGCGGCGGGTGTGGTGGTTACGCGCAGCGTGACCGCTACACTTGCCAGCGCCCTAGCGCC
CGCTCCTTTCGCTTTCTTCCCTTCCTTTCTCGCCACGTTCGCCGGCTTTCCCCGTCAAGCTCTAAATCGG
GGGCTCCCTTTAGGGTTCCGATTTAGAGCTTTACGGCACCTCGACCGCAAAAAACTTGATTTGGGTGATG
GTTCACGTAGTGGGCCATCGCCCTGATAGACGGTTTTTCGCCCTTTGACGTTGGAGTCCACGTTCTTTAA
TAGTGGACTCTTGTTCCAAACTGGAACAACACTCAACCCTATCGCGGTCTATTCTTTTGATTTATAAGGG
ATTTTGCCGATTTCGGCCTATTGGTTAAAAAATGAGCTGATTTAACAAATTCAGGGCGCAAGGGCTGCTA
AAGGAACCGGAACACGTAGAAAGCCAGTCCGCAGAAACGGTGCTGACCCCGGATGAATGTCAGCTACTGG
GCTATCTGGACAAGGGAAAACGCAAGCGCAAAGAGAAAGCAGGTAGCTTGCAGTGGGCTTACATGGCGAT
AGCTAGACTGGGCGGTTTTATGGACAGCAAGCGAACCGGAATTGCCAGCTGGGGCGCCCTCTGGTAAGGT
TGGGAAGCCCTGCAAAGTAAACTGGATGGCTTTCTTGCCGCCAAGGATCTGATGGCGCAGGGGATCAAGA
TCTGATCAAGAGACAGGATGAGGATCGTTTCGCATGATTGAACAAGATGGATTGCACGCAGGTTCTCCGG
CCGCTTGGGTGGAGAGGCTATTCGGCTATGACTGGGCACAACAGACAATCGGCTGCTCTGATGCCGCCGT
GTTCCGGCTGTCAGCGCAGGGGCGCCCGGTTCTTTTTGTCAAGACCGACCTGTCCGGTGCCCTGAATGAA
CTGCAGGACGAGGCAGCGCGGCTATCGTGGCTGGCCACGACGGGCGTTCCTTGCGCAGCTGTGCTCGACG
TTGTCACTGAAGCGGGAAGGGACTGGCTGCTATTGGGCGAAGTGCCGGGGCAGGATCTCCTGTCATCTCG
CCTTGCTCCTGCCGAGAAAGTATCCATCATGGCTGATGCAATGCGGCGGCTGCATACGCTTGATCCGGCT
ACCTGCCCATTCGACCACCAAGCGAAACATCGCATCGAGCGAGCACGTACTCGGATGGAAGCCGGTCTTG
TCGATCAGGATGATCTGGACGAAGAGCATCAGGGGCTCGCGCCAGCCGAACTGTTCGCCAGGCTCAAGGC
GCGCATGCCCGACGGCGAGGATCTCGTCGTGATCCATGGCGATGCCTGCTTGCCGAATATCATGGTGGAA
AATGGCCGCTTTTCTGGATTCAACGACTGTGGCCGGCTGGGTGTGGCGGACCGCTATCAGGACATAGCGT
TGGATACCCGTGATATTGCTGAAGAGCTTGGCGGCGAATGGGCTGACCGCTTCCTCGTGCTTTACGGTAT
CGCCGCTCCCGATTCGCAGCGCATCGCCTTCTATCGCCTTCTTGACGAGTTCTTCTGAATTGAAAAAGGA
AGAGTATGAGTATTCAACATTTCCGTGTCGCCCTTATTCCCTTTTTTGCGGCATTTTGCCTTCCTGTTTT
TGCTCACCCAGAAACGCTGGTGAAAGTAAAAGATGCTGAAGATCAGTTGGGTGCACGAGTGGGTTACATC
GAACTGGATCTCAACAGCGGTAAGATCCTTGAGAGTTTTCGCCCCGAAGAACGTTTTCCAATGATGAGCA
CTTTTAAAGTTCTGCTATGTCATACACTATTATCCCGTATTGACGCCGGGCAAGAGCAACTCGGTCGCCG
GGCGCGGTATTCTCAGAATGACTTGGTTGAGTACTCACCAGTCACAGAAAAGCATCTTACGGATGGCATG
ACAGTAAGAGAATTATGCAGTGCTGCCATAACCATGAGTGATAACACTGCGGCCAACTTACTTCTGACAA
CGATCGGAGGACCGAAGGAGCTAACCGCTTTTTTGCACAACATGGGGGATCATGTAACTCGCCTTGATCG
TTGGGAACCGGAGCTGAATGAAGCCATACCAAACGACGAGAGTGACACCACGATGCCTGTAGCAATGCCA
ACAACGTTGCGCAAACTATTAACTGGCGAACTACTTACTCTAGCTTCCCGGCAACAATTAATAGACTGGA
TGGAGGCGGATAAAGTTGCAGGACCACTTCTGCGCTCGGCCCTTCCGGCTGGCTGGTTTATTGCTGATAA
ATCTGGAGCCGGTGAGCGTGGGTCTCGCGGTATCATTGCAGCACTGGGGCCAGATGGTAAGCCCTCCCGT
ATCGTAGTTATCTACACGACGGGGAGTCAGGCAACTATGGATGAACGAAATAGACAGATCGCTGAGATAG
GTGCCTCACTGATTAAGCATTGGTAACTGTCAGACCAAGTTTACTCATATATACTTTAGATTGATTTAAA
ACTTCATTTTTAATTTAAAAGGATCTAGGTGAAGATCCTTTTTTGATAATCTCATGACCAAAATCCCTTAA
CGTGAGTTTTCGTTCCACTGAGCGTCAGACCCCGTAGAAAAGATCAAAGGATCTTCTTGAGATCCTTTTT
TTCTGCGCGTAATCTGCTGCTTGCAAACAAAAAAACCACCGCTACCAGCGGTGGTTTGTTTGCCGGATCA
AGAGCTACCAACTCTTTTTCCGAAGGTAACTGGCTTCAGCAGAGCGCAGATACCAAATACTGTCCTTCTA
GTGTAGCCGTAGTTAGGCCACCACTTCAAGAACTCTGTAGCACCGCCTACATACCTCGCTCTGCTAATCC
TGTTACCAGTGGCTGCTGCCAGTGGCGATAAGTCGTGTCTTACCGGGTTGGACTCAAGACGATAGTTACC
GGATAAGGCGCAGCGGTCGGGCTGAACGGGGGGTTCGTGCACACAGCCCAGCTTGGAGCGAACGACCTAC
ACCGAACTGAGATACCTACAGCGTGAGCATTGAGAAAGCGCCACGCTTCCCGAAGGGAGAAAGGCGGACA
GGTATCCGGTAAGCGGCAGGGTCGGAACAGGAGAGCGCACGAGGGAGCTTCCAGGGGGAAACGCCTGGTA
TCTTTATAGTCCTGTCGGGTTTCGCCACCTCTGACTTGAGCGTCGATTTTTGTGATGCTCGTCAGGGGGG
CGGAGCCTATGGAAAAACGCCAGCAACGCGGCCTTTTTACGGTTCCTGGCCTTTTGCTGGCCTTTTGCTC
ACATGTTCTTTCCTGCGTTATCCCCTGATTCTGTGGATAACCGTATTACCGCCTTTGAGTGAGCTGATAC
CGCTCGCCGCAGCCGAACGACCGAGCGCAGCGAGTCAGTGAGCGAGGAAGCGGAAG
```

FIGURE 12

METHODS AND REAGENTS FOR MOLECULAR CLONING

This application is a continuation application of U.S. application Ser. No. 09/935,280 filed Aug. 21, 2001, now U.S. Pat. No. 6,916,632; which claims benefit under 35 USC § 119(e) to U.S. Application Ser. No. 60/226,563 filed Aug. 21, 2000, now abandoned. The disclosure of each of the prior applications is considered part of and is incorporated by reference in the disclosure of this application.

BACKGROUND OF THE INVENTION

1. Field of the Invention

The invention relates generally to compositions and methods for facilitating the construction of recombinant nucleic acid molecules, and more specifically to compositions useful for covalently linking two or more nucleic acid molecules, including for directionally or non-directionally linking the nucleic acid molecules, and to methods of generating such covalently linked recombinant nucleic acid molecules.

2. Background Information

The ability to clone large numbers of nucleotides sequences, including gene sequences and open reading frames allows a great deal of information to be obtained about gene expression and the regulation thereof. In addition, such sequences can be useful for understanding the etiology of disease conditions and, ideally, can provide a means to diagnose and treat such diseases. However, while it is relatively simple matter to clone large numbers of expressed nucleotides sequences, for example, it is a more difficult undertaking to characterize the regulatory elements involved in the expression of such sequence and to properly express a polypeptide encoded by the sequence. In particular, there is a need for improved methods for ligating nucleic acid molecules and cloning nucleic acid molecules such that a functional recombinant nucleic acid molecule is produced. There is a particular need for directional cloning methods, wherein an insert can be cloned into a vector or linked to one or more other nucleic acid molecules in a predetermined orientation.

The use of topoisomerases provides a convenient means to improve cloning and ligation methods. For example, the use of topoisomerase to perform rapid ligation of polymerase chain reaction (PCR) products into a vector has cut traditionally laborious cloning methods down to a five minute procedure. As such, topoisomerase is particularly useful for high throughput cloning applications. However, given the current demand for expressing open reading frames (ORF) in genome scale molecular cloning procedures, there still remains a need to better control the orientation in which two or more nucleic acid molecules are linked such that functional recombinant nucleic acid molecules such as expressible cloned nucleic acid molecules can be prepared.

Expression of cloned ORFs demands that the PCR product be inserted into the vector in its correct orientation, so as to work in accord with functional expression domains located on the vector. In the current state of the art for topoisomerase mediated cloning, ORFs are amplified by PCR using various DNA polymerases. A polymerase such at Taq, which does not have a proof-reading function and has an inherent terminal transferase activity, is commonly used, and produces PCR products containing a single, non-template derived 3' A overhang at each end. These amplification products can be efficiently cloned into topoisomerase-modified vectors containing a single 3' T overhang at each end (TOPO TA Cloning® Kit, Invitrogen Corp., Carlsbad, Calif.). In comparison, a polymerase such as pfu, which has an inherent 3' to 5' exonuclease proof-reading activity, produces PCR products that are blunt-ended. Topoisomerase-modified vectors containing blunt ends are available for cloning of PCR products produced with proofreading polymerases (Zero Blunt TOPO® PCR Cloning Kit, Invitrogen Corp., Carlsbad, Calif.). Incubation of either PCR product and the proper topoisomerase-modified vector results in five minute ligation. However, the orientation of the insert obtained using such cloning methods is random.

Because the orientation of DNA fragment insertion into topoisomerase-modified cloning vectors is random, users must screen clones to identify those having the proper orientation. Insert orientation can be determined using various methods including, for example, restriction enzyme analysis, in vitro transcription from vector-encoded promoter elements, and PCR using, for example, one insert-specific primer and one vector-specific primer. As is evident, however, the requirement for determining insert orientation requires an investment of time and can substantially increase the cost for identifying a nucleic acid molecule of interest, particularly where a high throughput cloning method is used. As such, current cloning methods are severely limited, particularly for high throughput gene expression analysis for several reasons, because numerous laborious steps must be performed in order to select clones with correctly oriented inserts, and there is a need to screen as many as eight colonies of each clone to identify one having the proper orientation. Thus, a need exists for methods and reagents that are useful for covalently linking two or more nucleic acid molecules in a directional orientation. The present invention satisfies this need and provides additional advantages.

SUMMARY OF THE INVENTION

The present invention provides compositions and methods for covalently linking two or more (e.g., 2, 3, 4, 5, 6, 7, 8, 9, 10, etc.) double stranded ("ds") nucleic acid molecules, including directionally or non-directionally linking two or more ds nucleic acid molecules. Nucleic acid molecules used in accordance with the invention preferably comprise a first end and a second end. The first and/or second end of such molecules preferably has a 5' and/or 3' extension or overhang. Thus, one or both ends of the nucleic acid molecules used in the invention can have a 3' and/or 5' overhang. The overhang sequences can be the same or different sequences, and can be the same or different types (e.g., 3' or 5' overhang) at both ends of the molecule. In addition, while one end of the nucleic acid molecule can have a 3' extension and 5' extension, the other end of the molecule can, but need not, have an extension. In some aspects, one end of nucleic acid molecule can contain a 3' overhang or 5' overhang while the other end can be blunt ended (i.e., it has no overhang). In accordance with the invention, the 3' and/or 5' extension sequences (i.e., overhangs) at any terminus can be any length (i.e., any number of nucleotides), and can have any sequence. Thus, the invention relates to nucleic acid molecules having single or multiple nucleotide overhangs. In some aspects, the nucleic acid molecules and their termini can include modified or labeled nucleotides. In the use of the invention, enzymes or proteins capable of fusing or joining or ligating nucleic acid molecules can be used. Thus, two or more nucleic acid molecules, which can be the same or different, can be joined directionally using such enzymes. Such enzymes or proteins include, but are not limited to, topoisomerases (including types IA, IB, II, etc.), recombinase proteins (including FLIP recombinase, Int integrase, cre recombinase, etc.), and ligases (including T4 DNA ligase, etc.).

In the methods of the invention, the 3' or 5' overhang of one terminus of the first nucleic acid molecule can have homology (or is complementary) to at least one sequence at or near the terminus of at least a second nucleic acid molecule. Thus, through base pairing or hybridization of the 3' or 5' overhang or extension with the homologous or complementary sequence on the second molecule, the invention allows directional or non-directional association or joining of two different molecules. In a preferred aspect, the 3' or 5' overhang of one terminus of at least a first molecule can engage in strand invasion as it associates or hybridizes with its complementary sequence at or near the terminus of the second molecule. In one aspect, Such a strand invasion event allows the 3' or 5' overhang to directionally associate with a desired end of its partner molecule. By designing the overhangs and the termini of the molecules to be joined, two or multiple partner molecules can be joined in the presence of one or more proteins or enzymes having ligase activity (e.g., topoisomerases, ligases, recombinases, etc.) in accordance with the invention. Thus, the invention provides methods for connecting two or more nucleic acid molecules (e.g., double stranded nucleic acid molecules) which involve covalently linking at least one strand of one molecule to at least one strand of another molecule. The invention further provides compositions for preparing nucleic acid molecules connected by methods of the invention and compositions produced by methods of the invention.

Processes of the invention are exemplified by methods described herein which involve the covalent linkage of strands of different nucleic acid molecules catalyzed by topoisomerase. Thus, the present invention relates, in part, to an isolated ds nucleic acid molecule having a first end and a second end, wherein the first end contains a first 5' overhang and a first topoisomerase covalently bound at the 3' terminus, and the second end contains a second topoisomerase covalently bound at the 3' terminus and contains a second 5' overhang, a blunt end, or a 3' thymidine overhang, wherein the first 5' overhang is different from the second 5' overhang. The first topoisomerase and second topoisomerase can be the same or different. The first 5' overhang can have any nucleotide sequence, including, for example, the nucleotide sequence 5-GGTG-3'.

In one embodiment, the ds nucleic acid molecule is a vector, which can be a linear vector such as a lambda vector or a linearized vector such as a linearized plasmid. The vector can be a cloning vector or an expression vector, and can contain, for example, one or more (e.g., 1, 2, 3, 4, 5, 6, etc.) recombinase recognition sites such as one or more lox sites or one or more att sites, one or more transcriptional regulatory elements, one or more translational regulatory elements, one or more nucleotide sequences encoding a peptide of interest such as one or more selectable markers or one or more tags, or combinations thereof. For example, the vector can be a pUni/V5-His version A (SEQ ID NO: 16) vector or a pCR®2.1 (SEQ ID NO: 17) vector.

The present invention also relates to methods of directionally or non-directionally linking two, three, four or more nucleic acid molecules, including, as desired, operatively linking two or more of the nucleic acid molecules. A method for generating a directionally linked recombinant nucleic acid molecule can be performed, for example, by contacting a first topoisomerase-charged first ds nucleic acid molecule, which has a first topoisomerase covalently bound at a first end, and a second topoisomerase covalently bound at a second end, and also contains a 5' overhang at the first end and a blunt end, a 3' uridine overhang, a 3' thymidine overhang, or a second 5' overhang at the second end; and at least a second ds nucleic acid molecule, which has a first blunt end and a second end, wherein the first blunt end has 5' nucleotide sequence that is complementary to the first 5' overhang of the first end of the first nucleic acid molecule. The first and second topoisomerases can be the same, for example, two type IB topoisomerases such as two Vaccinia type IB topoisomerases, or can be different, including two type IB topoisomerases from different organisms or a type IB topoisomerase and a type IA or a type II topoisomerase.

In performing a method of the invention, the first and second (or other) ds nucleic acid molecules are contacted under conditions such that the 5' nucleotide sequence of the first blunt end of the second nucleic acid molecule can selectively hybridize to the first 5' overhang, whereby the first topoisomerase can covalently link the 3' terminus of the first end of the first ds nucleic acid molecule to the 5' terminus of the first blunt end of the second ds nucleic acid molecule, and the second topoisomerase can covalently link the 3' terminus of the second end of the first ds nucleic acid molecule to the 5' terminus of the second end of the second ds nucleic acid molecule, to generate a directionally linked recombinant nucleic acid molecule. Accordingly, the present invention provides a directionally or non-directionally linked recombinant nucleic acid molecule produced by such a method.

In one aspect of performing a method of the invention, the second end of the first topoisomerase-charged ds nucleic acid molecule has a blunt end, and the second end of the second ds nucleic acid molecule has a blunt end. In another aspect, the second end of the topoisomerase-charged first ds nucleic acid molecule has a 3' thymidine overhang, and the second end of the second ds nucleic acid molecule has a 3' adenosine overhang, or the second end of the topoisomerase-charged first ds nucleic acid molecule has a 3' uridine (or modified form thereof, for example, deoxyuridine) overhang, and the second end of the second ds nucleic acid molecule has a 3' adenosine overhang. In yet another aspect, the topoisomerase-charged first ds nucleic acid molecule has a second 5' overhang at the second end, and the second end of the second ds nucleic acid has a nucleotide sequence complementary to the second 5' overhang. The topoisomerase-charged first ds nucleic acid molecule can, but need not be, a vector, including a cloning vector or an expression vector.

A method of the invention can further include introducing a directionally or non-directionally-linked recombinant nucleic acid molecule into a cell, which can be a prokaryotic cell such as a bacterium or a eukaryotic cell such as a mammalian cell. Accordingly, the present invention also provides a cell produced by a method of the invention, as well as a non-human transgenic organism produced from such a cell.

The topoisomerase-charged first ds nucleic acid molecule can be a vector, and the second ds nucleic acid molecule used in a method of the invention can be an amplification product. In addition, the second ds nucleic acid molecule can be one of a plurality of second ds nucleotide molecules, for example, individual members of a cDNA library or a combinatorial library.

A method for generating a directionally or non-directionally linked recombinant nucleic acid molecule also can be performed, for example, by contacting a first precursor ds nucleic acid molecule having a first end, which has a first 5' target sequence at the 5' terminus and a topoisomerase recognition site at the 3' terminus, and a second end, which has a topoisomerase recognition site at the 3' terminus; a second ds nucleic acid molecule having a first blunt end and a second end, wherein the first blunt end has a 5' nucleotide sequence complementary to the 5' target sequence of the first precursor ds nucleic acid molecule; and a topoisomerase that is specific for the topoisomerase recognition site. The first ds nucleic acid molecule, second ds nucleic acid molecule and topoisomerase are contacted under conditions that allow topoisomerase activity, i.e., such that the topoisomerase can bind to and cleave the recognition site, to produce a topoisomerase-charged 3' terminus, and can ligate the 3' terminus to an appropriate 5' terminus. Such conditions also allow hybridization of the portion of the first 5' target sequence that remains following cleavage by the topoisomerase and the 5' nucleotide sequence of the first blunt end of the second ds nucleic acid molecule, wherein the 5' nucleotide sequence of the first blunt end is complementary to that portion of the 5' target sequence.

In one aspect of performing a method of the invention, the second end of the first precursor ds nucleic acid molecule is a blunt end upon cleavage by the topoisomerase, and the second end of the second ds nucleic acid molecule is a blunt end. In another aspect, the second end of the first precursor ds nucleic acid molecule has a 3' thymidine extension upon cleavage by the topoisomerase, and the second end of the second ds nucleic acid molecule comprises a 3' adenosine or 3'-uridine, for example, deoxyuridine overhang. In yet another aspect, the first precursor ds nucleic acid molecule has a second 5' target sequence at the second end, and the second end of the second ds nucleic acid molecule has a 5' nucleotide sequence complementary to at least a portion of the second 5' target sequence.

The first precursor ds nucleic acid molecule can be a vector, including a cloning vector and an expression vector, and, where the vector generally is available in a circular form, can be linearized due to the action of the topoisomerase, or can be linearized by including, for example, one or two restriction endonucleases that linearize the vector such that, upon contact with the topoisomerase, the first and second ds nucleic acid molecules can be directionally or non-directionally linked according to a method of the invention. The present invention also provides a directionally or non-directionally linked recombinant nucleic acid molecule produced according to a method of the invention, which can further include, for example, a step of introducing the directionally-linked recombinant nucleic acid molecule into a cell. Accordingly, the present invention also provides a cell containing such a directionally or non-directionally linked recombinant nucleic acid molecule, as well as a transgenic non-human organism generated from such a cell.

The first precursor ds nucleic acid molecule can include one or more (e.g., 1, 2, 3, 4, 5, 6, 7, etc.) expression control elements, which can be operatively linked to each other, and the second ds nucleic acid molecule can encode all or a portion of an open reading frame, wherein the expression control element is operatively linked to the open reading frame in a directionally linked recombinant nucleic acid molecule generated according to a method of the invention. In addition, the second ds nucleic acid molecule can be one of a plurality of second ds nucleic acid molecules, for example, individual members of a cDNA library.

A method for generating a directionally linked recombinant nucleic acid molecule also can be performed by contacting a topoisomerase-charged first ds nucleic acid molecule, which has, at a first end, a first 5' overhang and a first topoisomerase covalently bound to the 3' terminus, and a second ds nucleic acid molecule, which has a first blunt end and a second end, wherein the first blunt end includes a 5' nucleotide sequence complementary to the first 5' overhang. The method is performed under conditions such that the 5' nucleotide sequence of the first blunt end can selectively hybridize to the first 5' overhang, whereby the first topoisomerase can covalently link the 3' terminus of the first end of the first ds nucleic acid molecule with the 5' terminus of the first end of the second ds nucleic acid molecule.

Such a method can further include contacting the topoisomerase-charged first ds nucleic acid molecule and the second ds nucleic acid molecule with a third ds nucleic acid molecule, wherein a first end of the third nucleic ds acid molecule has a 5' overhang and a second topoisomerase covalently bound at the 3' terminus, and wherein the second ds nucleic acid molecule has a second blunt end, which includes a 5' nucleotide sequence complementary to the second 5' overhang. The contacting can be performed, for example, under conditions such that the 5' nucleotide sequence of the second blunt end of the second ds nucleic acid can selectively hybridize to the 5' overhang of the first end of the third ds nucleic acid molecule, whereby the second topoisomerase can covalently link the 3' terminus of the first end of the third ds nucleic acid molecule with the 5' terminus of the second blunt end of the second ds nucleic acid molecule. Similarly, the method can be used to directionally or non-directionally link a fourth, fifth, sixth, or more ds nucleic acid molecules, wherein the ends of such ds nucleic acid molecules are selected as exemplified herein. The first and second (or other) topoisomerases can be the same or different and, if desired, the first or third ds nucleic acid molecules, instead of being topoisomerase-charged, can contain a topoisomerase recognition site, wherein the method can further include contacting the reactants with a topoisomerase.

A method of the invention can be performed simultaneously or sequentially. A method of the invention can be performed sequentially, for example, such that the first ds nucleic acid molecule is directionally linked to the second ds nucleic acid molecule and, at a later time or in a different reaction vessel, the third ds nucleic acid molecule is directionally linked to the second ds nucleic acid molecule. Alternatively, the method can be performed simultaneous, wherein all of the reactants are included together at the same time.

Methods of the invention are particularly useful for operatively linking two or more (e.g., 2, 3, 4, 5, 6, 7, 8, etc.) ds nucleic acid molecules, including, for example, operatively linking an expression control element to an open reading frame, or operatively linking a first and second open reading frame to generate a recombinant nucleic acid molecule encoding a fusion protein, which can be further operatively linked to one or more expression control element. For example, in practicing a method of the invention, a first ds nucleic acid molecule can include an expression control element, a second ds nucleic acid molecule can encode an open reading frame, and a third ds nucleic acid molecule can encode a peptide, wherein, in the directionally linked recombinant nucleic acid molecule, the expression control element is operatively linked to the open reading frame, and the second ds nucleic acid molecule is operatively linked to the third ds nucleic acid molecule, and wherein the operatively linked second and third ds nucleic acid molecules encode a fusion protein comprising the open reading frame and the peptide. The peptide can be any peptide or polypeptide, including a gene product or other open reading frame, a tag (e.g., an affinity tag), a detectable label, and/or the like.

The present invention also relates to a composition, which includes a first ds nucleic acid molecule having a first end and a second end, wherein the first end has a 5' overhang and a topoisomerase covalently bound at the 3' terminus; and a second ds nucleic acid molecule having a first blunt end and a second end, wherein the first blunt end has a first 5' nucleotide sequence, which is complementary to the first 5'-overhang, and a first 3' nucleotide sequence complementary to the first 5' nucleotide sequence. In such a composition, the first 5' nucleotide sequence of the first blunt end of the second ds nucleic acid molecule can be hybridized to the first 5' overhang of the first end of the first nucleic acid molecule, wherein the first 3' nucleotide sequence of the first blunt end of the second ds nucleic acid molecule is displaced. The first ds nucleic acid molecule in such a composition can further have a second 5' overhang at the second end, and the second end of the second ds nucleic acid molecule can further include a second 5' nucleotide sequence, which is complementary to the second 5' overhang, and a second 3' nucleotide sequence complementary to the second 5' nucleotide sequence.

The present invention also relates to kits, which contain one or more reagents useful for directionally linking ds nucleic acid molecules. In one embodiment, a kit of the invention contains a ds nucleic acid molecule having a first end and a second end, wherein the first end contains a first 5' overhang and a first topoisomerase covalently bound at the 3' terminus, and the second end contains a second topoisomerase covalently bound at the 3' terminus and contains a second 5' overhang, a blunt end, or a 3' thymidine overhang, wherein the first 5' overhang is different from the second 5' overhang. The topoisomerases can be the same or different, and the ds nucleic acid molecule can be a vector, and can contain an expression control element.

In another embodiment, a kit of the invention contains a first ds nucleic acid molecule, which has a first topoisomerase covalently bound at a 3' terminus of a first end, and a second topoisomerase covalently bound at a 3' terminus of a second end, wherein the first end also has a first 5' overhang and the second end also has a blunt end, a 3' thymidine overhang, or a second 5' overhang, wherein, when present, the second 5' overhang is different from the first 5' overhang; and a plurality of second ds nucleic acid molecules, wherein each ds nucleic acid molecule in the plurality has a first blunt end, and wherein the first blunt end includes a 5' nucleotide sequence complementary to the first 5' overhang of the first ds nucleic acid molecule. The second ds nucleic acid molecules in the plurality can be a plurality transcriptional regulatory elements, translational regulatory elements, or a combination thereof, or can encode a plurality of peptides such as peptide tags, cell compartmentalization domains, and the like.

A kit of the invention can contain one or more (e.g., 1, 2, 3, 4, 5, 6, 7, 8, etc.) topoisomerase-charged ds nucleic acid molecules of the invention, for example, one or more (e.g., 1, 2, 3, 4, 5, 6, 7, 8, etc.) topoisomerase-charged vectors; one or more (e.g., 1, 2, 3, 4, 5, 6, 7, 8, etc.) precursor ds nucleic acid molecules, which can be contacted with a topoisomerase to produce a topoisomerase-charged ds nucleic acid molecule of the invention; or a combination thereof. The kit also can contain one or more primers or primer pairs, for example, for preparing one or a plurality of second ds nucleic acid molecules using an amplification reaction; one or more control ds nucleic acid molecules to test or standardize the components of the kit; one or more cells, which can be, for example, competent cells into which a recombinant nucleic acid molecule generated according to a method of the invention can be introduced; one or more (e.g., 1, 2, 3, 4, 5, 6, 7, 8, etc.) reaction buffers for performing a method of the invention; instructions for carrying out the method; and the like.

In one embodiment, a method for generating a directionally or non-directionally linked recombinant nucleic acid molecule is performed using a first ds nucleic acid molecule with one single stranded overhang, and one topoisomerase site or one topoisomerase bound thereto. In another embodiment, a third nucleic acid molecule is included. In accordance with this aspect of the invention, unique overhang sequences for the different ds nucleic acid molecules to be linked can be prepared having unique overhangs such that the nucleic acid molecules can be linked directionally and in any desired order. Similarly, the method can be used to link any number of nucleic acid molecules, including directionally linking two or more of the number of nucleic acid molecules. In certain embodiments involving a topoisomerase-charged ds nucleic acid molecule containing an expression control element, a third (or other) ds nucleotide sequence also can comprise one, two or more expression control elements or other sequence of interest.

The present invention provides a method for the directional insertion of DNA fragments into cloning or expression vectors with the ease and efficiency of topoisomerase-mediated cloning. This method has advantages over current cloning systems because it decreases the laborious screening process necessary to identify cloned inserts in the desired orientation. In one aspect, the method utilizes a linearized expression vector having a single topoisomerase molecule covalently attached at both 3' ends. A first end of the linearized vector also can contain a 5' single stranded overhang, and the second end can be either blunt, possess a single 3' thymidine extension for T/A cloning, or can itself contain a second 5' single stranded overhang sequence. The single stranded overhang sequences can be any convenient or desired sequence.

Construction of a topoisomerase-charged cloning vector can be accomplished by endonuclease digestion of the vector, followed by complementary annealing of synthetic oligonucleotides and site-specific cleavage of the heteroduplex by Vaccinia topoisomerase I. Digestion of a vector with any compatible endonuclease creates specific sticky ends. Custom oligonucleotides are annealed to these sticky ends, and possess sequences that, following topoisomerase I modification, form custom ends of the vector. The sequence and length of the single stranded overhang will vary based on the desires of the user.

In a preferred use of the single strand sequence topoisomerase-charged ds nucleic acid vectors provided by the present invention, the DNA fragment to be inserted into the vector is an amplification reaction product such as a PCR product. Following PCR amplification with custom primers, the product can be directionally inserted into a topoisomerase I charged cloning vector having a single strand sequence on one or both ends of the insertion site. The custom primers can be designed such that at least one primer of a given primer pair contains an additional sequence at its 5' end. The added sequence is designed to be complementary to the sequence of the single stranded overhang in the vector. The complementarity between the 5' single stranded overhang in the vector and the 5' end of the PCR product mediates the directional insertion of the PCR product into the topoisomerase-mediated vector. Specifically, since only one end of the vector and one end of the PCR product possess complementary single stranded sequence regions, the insertion of the product in this instance is directional, and topoisomerase can catalyze ligation of the PCR product to the vector.

BRIEF DESCRIPTION OF THE FIGURES

FIG. 1A shows two ds nucleic acid molecules (labeled "first" and "second" molecules) which each contain one terminus that is capable of engaging in strand invasion with a terminus of the second molecule (see boxes). When a topoisomerase is used to covalently link (e.g., ligate) strands of each molecule, the 3' recessed strand of the terminus of the first molecule will generally be charged with topoisomerase. Further, this topoisomerase will generally catalyze the covalent linkage of the 3' recessed strand of the terminus of the first molecule to the 5' strand of the second molecule with which it engages in strand invasion (i.e., the 5' terminus of the second nucleic acid molecule which is shown in the box).

FIG. 1B shows two ds nucleic acid molecules (labeled "first" and "second" molecules), each of which contains two termini that are capable of engaging in strand invasion with termini of the other molecule. Further, each of these two nucleic acid molecules has a blunt terminus and a terminus with a 5' single stranded overhang (see circles and boxes). The nucleic acid molecules in this depiction can thus engage in two separate strand invasion events which, upon covalent linkage of nucleic acid strands at each termini, result in the formation of a single, circular nucleic acid molecule. Covalent linkage of the termini can be performed as described, for example, for FIG. 1A, above.

FIG. 1C shows two ds nucleic acid molecules (labeled "first" and "second" molecules), each of which contains two termini that are capable of engaging in strand invasion with different termini of the other molecule. Further, one of these molecules has two blunt termini and the other molecule has 5' single stranded overhangs on each terminus. The molecules in this depiction can thus engage in two separate strand invasion events which, upon covalent linkage of nucleic acid strand at each termini, result in the formation of a circular nucleic acid molecule. Covalent linkage of the termini can be performed as described for FIG. 1A, above.

FIG. 1D shows three ds nucleic acid molecules (labeled "first", "second" and "third" molecules). Two of these molecules ("first" and "third" molecules) contain 5' single stranded overhangs which are capable of engaging in strand invasion with different blunt termini of the other molecule ("second" molecule). The molecules in this depiction can thus engage in two separate strand invasion events, which result in the generation of a linear nucleic acid molecule composed of all three molecules. Covalent linkage of the termini can be performed as described for FIG. 1A, above.

FIG. 1E shows nucleic acid molecules similar to those set out in FIG. 1D, above, except that one of the nucleic acid molecules ("second" molecule) has 5' overhangs at both termini and the other two nucleic acid molecules ("first" and "second" molecules) each have two blunt termini.

FIG. 3 provides the nucleotide sequence and the location of restriction endonuclease recognition sequences of the Multiple Cloning Site of pUni/V5-His version A (SEQ ID NO: 18), and a plasmid map of this 2.3 kb vector. EcoRI cloning site is located at nucleotide 471, and SacI cloning site is located at nucleotide 528.

FIG. 5 provides the nucleotide sequence of the Vector pUni/V5-His version A sequence (SEQ ID NO:16).

```
TOPO D1:
5'-AATTGATCCCTTCACCGACATAGTACAG-3'    (SEQ ID NO:5)

TOPO D2:
3'-CTAGGGAAGTGG-5'                     (SEQ ID NO:6)

TOPO D3:
3'-GACATGATACAGTTCCCGC-5'              (SEQ ID NO:8)

TOPO D4:
5'-AAGGGCGAGCT-3'                      (SEQ ID NO:7)
```

T4 ligation reaction will yield the indicated linearized cloning vector, adapter sequences are underlined for demarcation.

Figure 8:
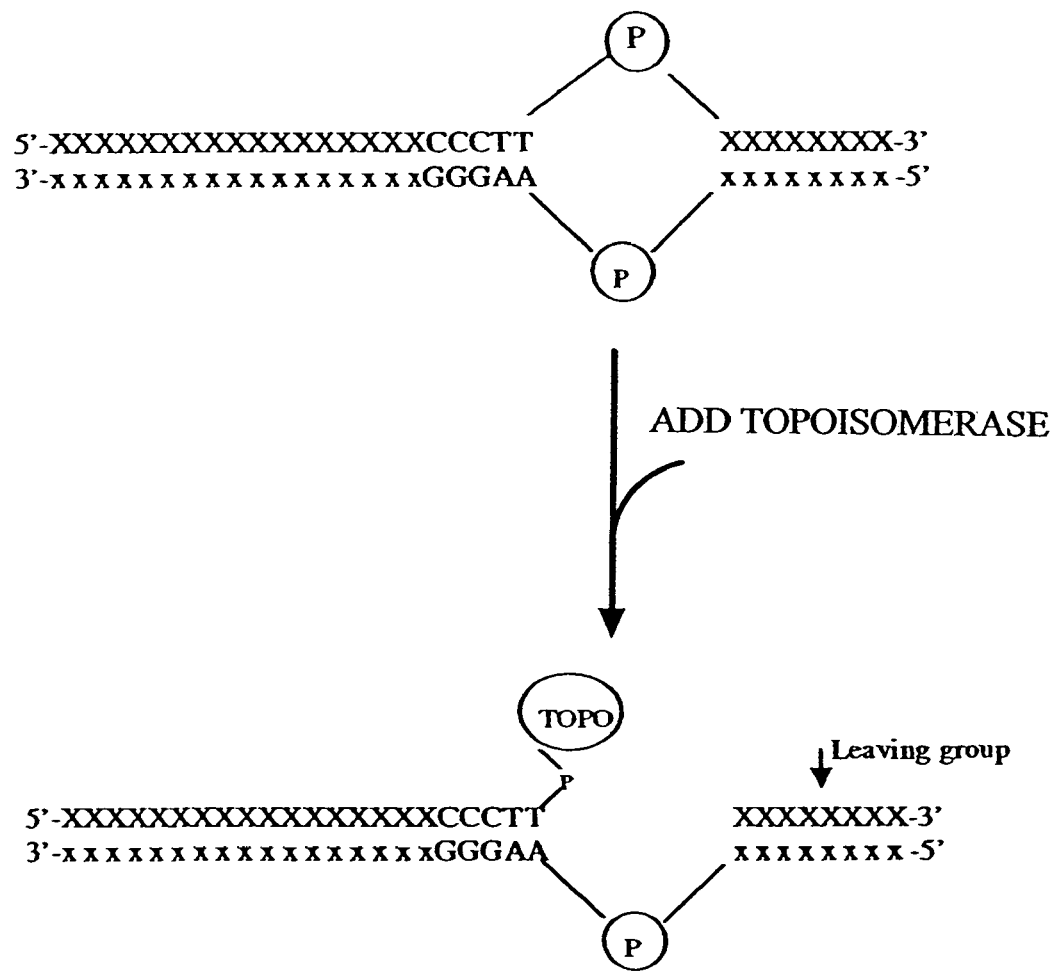

FIG. 8 illustrates a topoisomerase cleavage reaction wherein following topoisomerase cleavage of the scissile strand, a phosphate bond in the non-scissile strand keeps the leaving group associated to the vector. In the reaction shown, topoisomerase is added to the depicted ds nucleic acid molecule. Topoisomerase binds CCCTT and breaks the adjacent phosphodiester bond. Phosphodiester bonds between the adapted vector and the annealing oligo in the non-scissile strand prevent the dissociation of the leaving group upon cleavage. In the double stranded DNA model illustrated, X and x represent complementary nucleotide bases.

Figure 9:
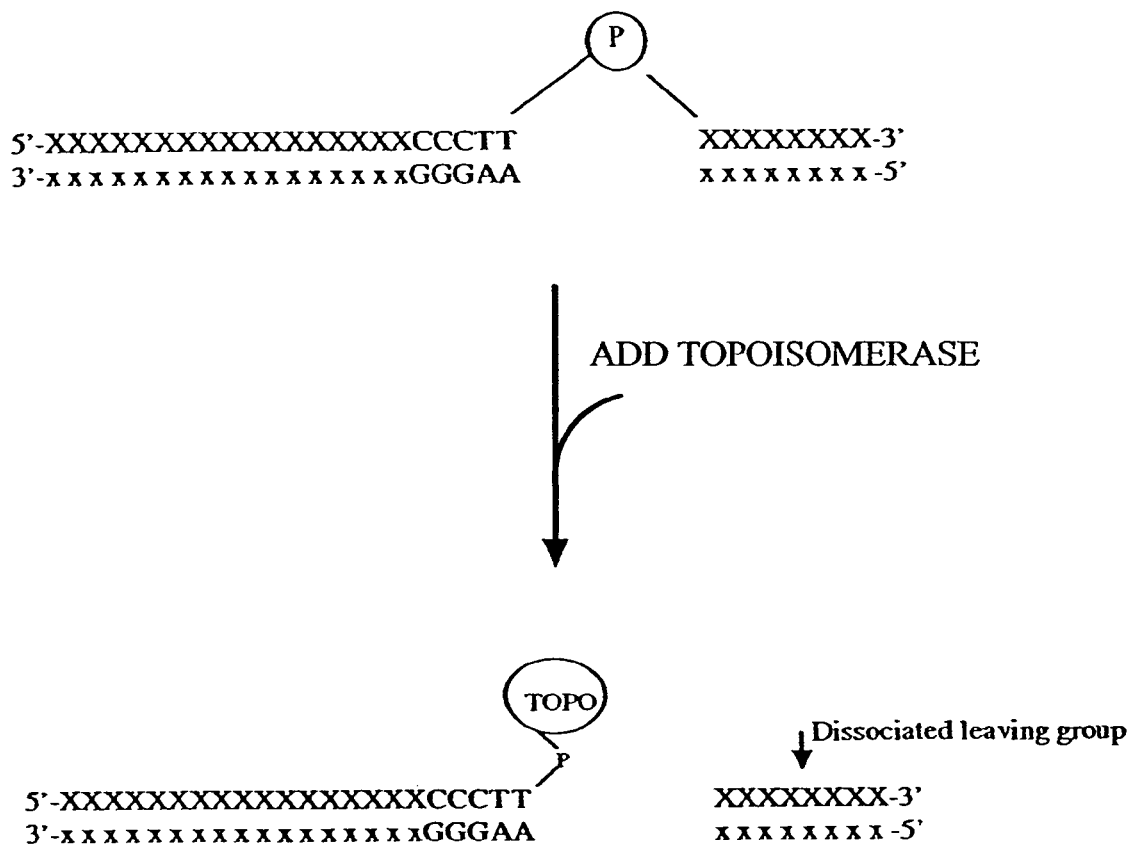

FIG. 9 illustrates a topoisomerase cleavage reaction wherein following topoisomerase cleavage of the scissile strand, the lack of a phosphate bond in the non-scissile strand allows the leaving group to dissociate from the vector. In the reaction shown, topoisomerase is added to the depicted ds nucleic acid molecule. Topoisomerase binds CCCTT and breaks the adjacent phosphodiester bond. Lack of a phosphodiester bond between the adapted vector and the annealing oligo in the non-scissile strand allows the dissociation of the leaving group upon cleavage. In the double stranded DNA model illustrated, X and x represent complementary nucleotide bases.

Figure 10:
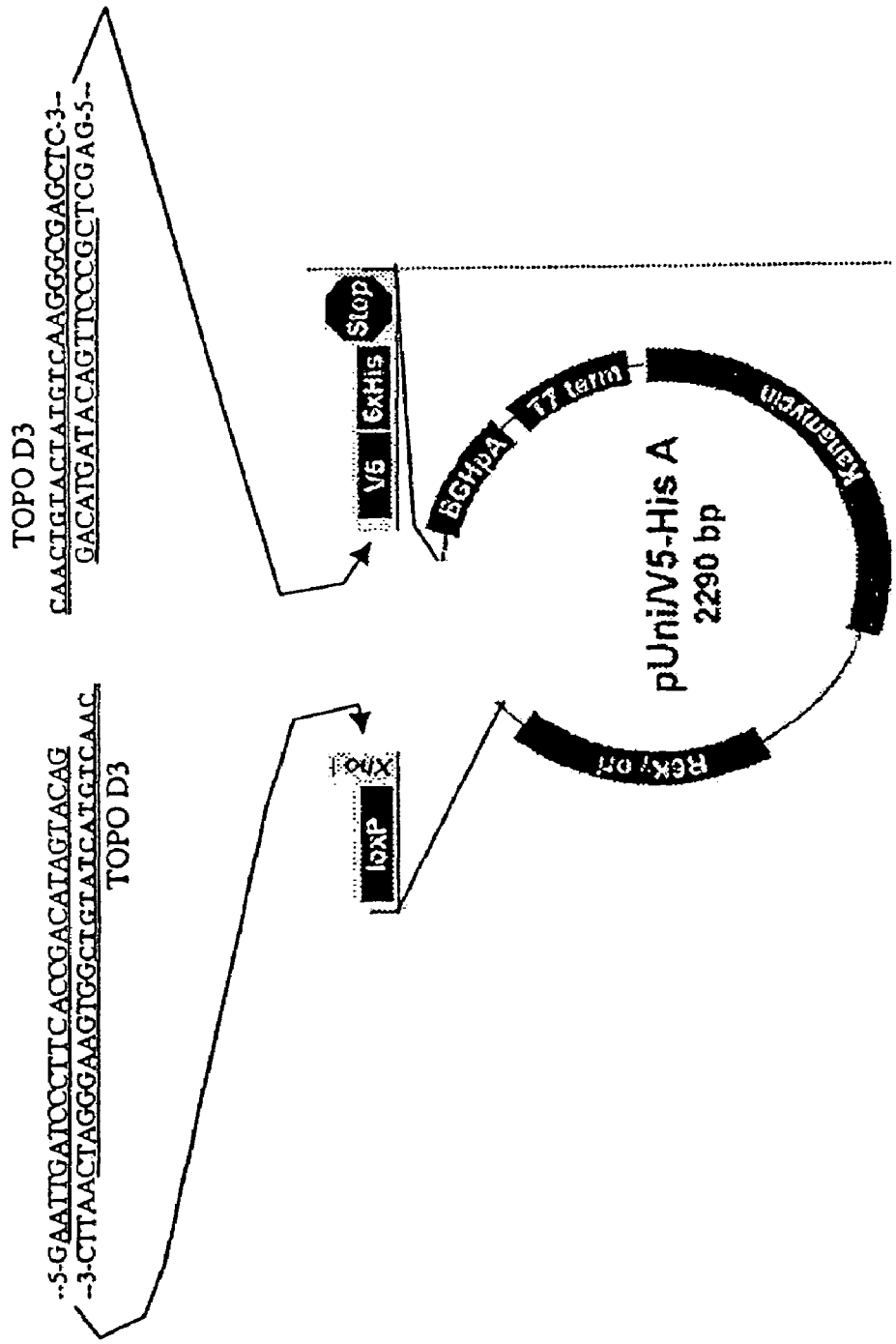

FIG. 10 illustrates that addition of an annealing oligonucleotide to the linearized, adapted vector in the absence of DNA ligase yields the exhibited linearized, adapted and annealed vector. Note that the annealing oligonucleotide is not bound to the vector by a phosphate bond, thus, allowing dissociation following topoisomerase mediated cleavage. Adapter oligonucleotides are demarcated by a single underline, while annealing oligonucleotides are demarcated by a double underline. There are no phophodiester linkages between either of the TOPO D3s and their adjacent oligonucleotides TOPO D2 and TOPO D5 The annealing oligonucleotide has the following sequence and is complementary to both TOPO D1's and TOPO D4's single stranded overhang: TOPO D3 3'-CTGTATCATGTCAAC-5' (SEQ ID NO:10).

Figure 11:
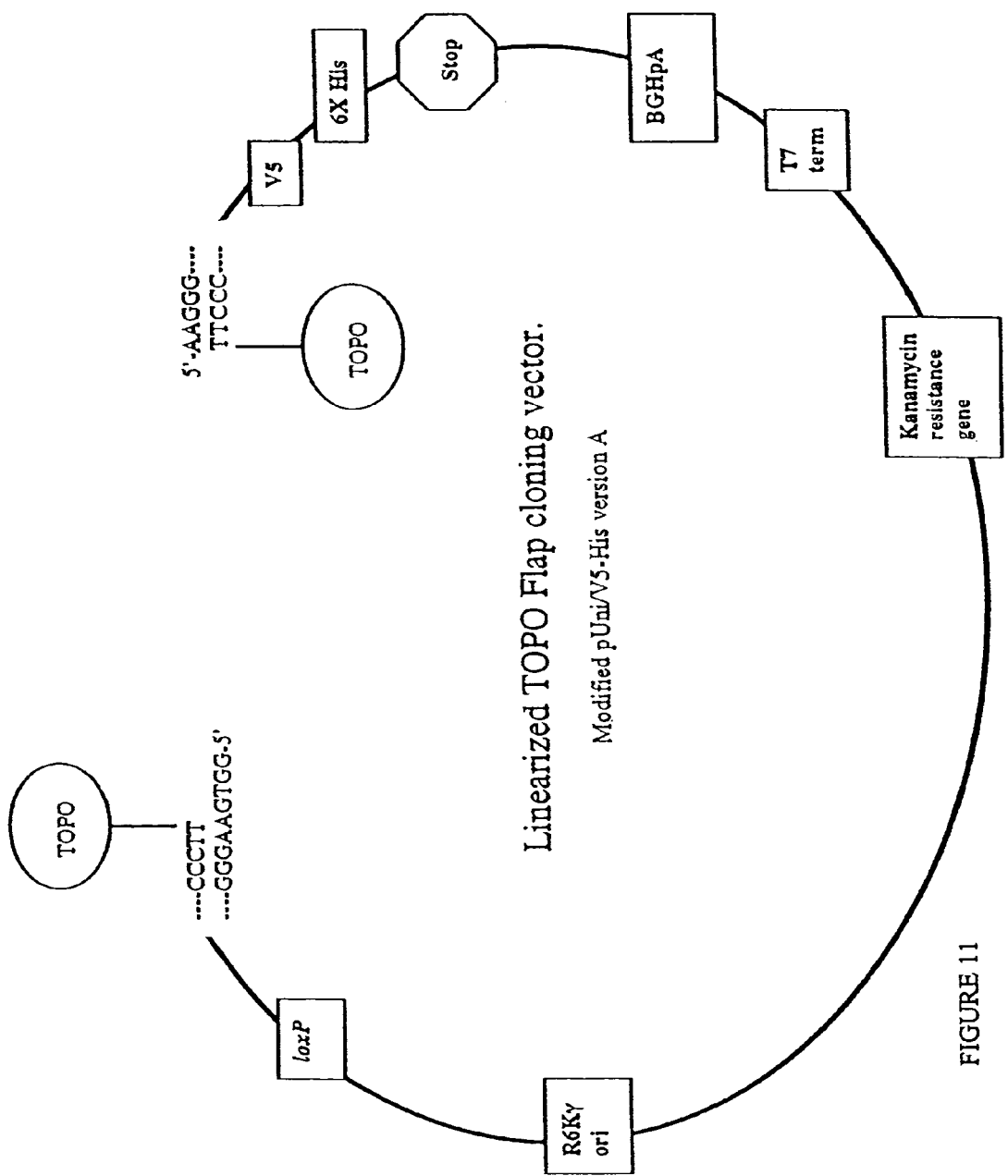

FIG. 11 shows an example of a linearized topoisomerase-charged ds nucleic acid cloning vector of the invention. The single stranded overhang corresponds to a Kozak transcription sequence. The vector illustrated is a linearized TOPO flap cloning vector, modified pUni/His version A.

FIG. 12 is the nucleotide sequence of vector pCR 2.1 sequence (SEQ ID NO:17).

FIGS. 13A and 13B show forms of the pCR2.1® vector.

FIG. 13A shows pCR2.1® following restriction digestion with EcoRI and HindIII (note the resulting sticky ends). Four adapter oligonucleotides were ligated to the linearized vector. TOPO binding sites on the oligonucleotides have the sequence CCCTT (underlined). Sticky end complementary bases are depicted in bold. The four adapter oligonucleotides had the following sequences:

```
TOPO H:
5'-AGCTCGCCCTTATTCCGATAGTG-3';    (SEQ ID NO:11)

TOPO 16:
3'-GCGGGAATAAG;                    (SEQ ID NO:12)

TOPO 1:
5'-AATTCGCCCTTATTCCGATAGTG-3';    (SEQ ID NO:13)
and

TOPO 2:
3'-GCGGGAA-5'
```

TOPO H and TOPO 1 have 5' ends that complement the HindIII and EcoRI sticky ends, respectively.

FIG. 13B shows the adapted version of pCR2.1® following incubation with the adapter oligos in the presence of T4 ligase.

Figure 14:
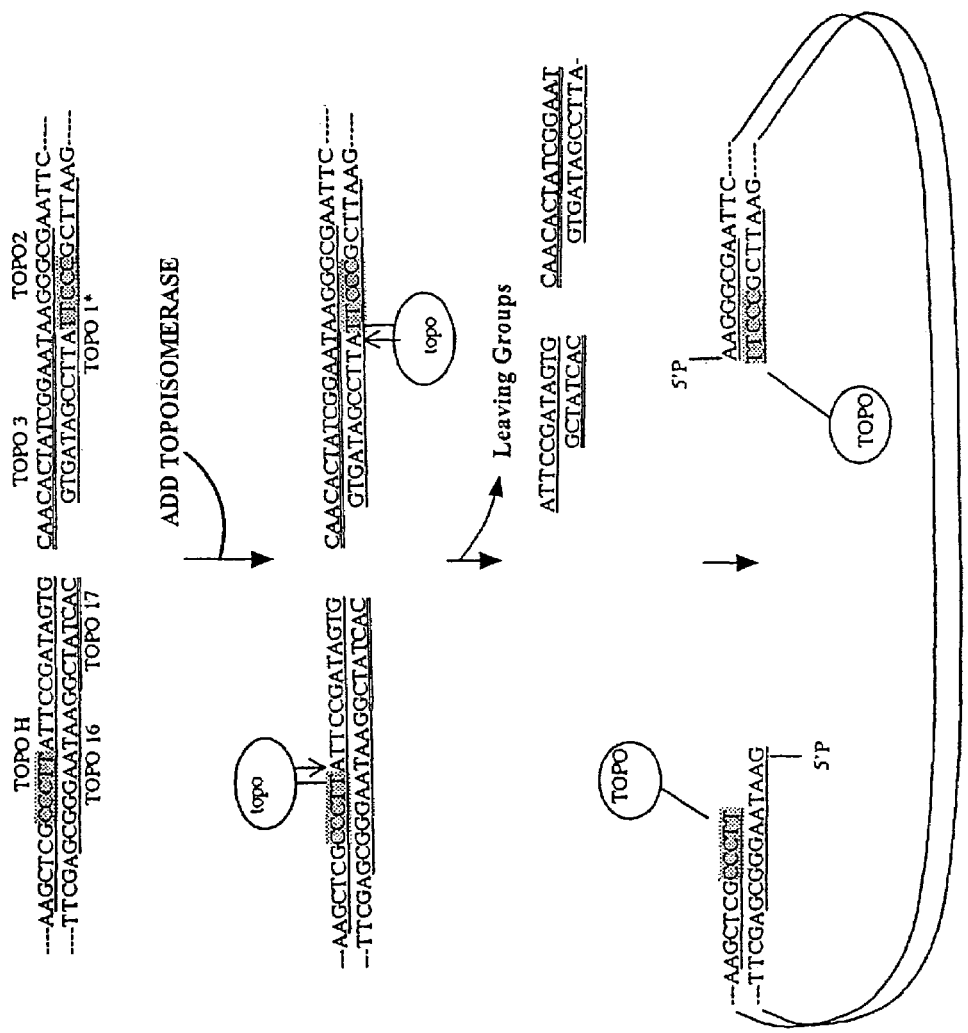

FIG. 14 illustrates the addition of annealing oligonucleotides to the adapted pCR2.1® vector, followed by the binding of topoisomerase I and the topoisomerase mediated cleavage of the double stranded vector. The resulting vector is linear and charged with topoisomerase I on both ends. Also, one end of the vector has the custom 4 bp single stranded sequence, while the other end is blunt. In the initial reaction illustrated, topoisomerase binds and cleaves the double stranded DNA at the 5' end of the covalent binding site located near the ends of pCR2.1®, which contain the bound adapter and annealing oligonucleotides. This step is performed in the presence of T4 polynucleotide kinase. The annealing oligonucleotides have the following sequences:

```
TOPO 3:    3'-TAAGGCTATCACAAC-5';    (SEQ ID NO:15)
and

TOPO 17:   3'-GCTATCAC-5'
```

There are no phophodiester bonds formed between TOPO 3 and TOPO 2, or between TOPO 17 and TOPO 16. The annealing oligonucleotides are double underlined for demarcation.

Figure 15:
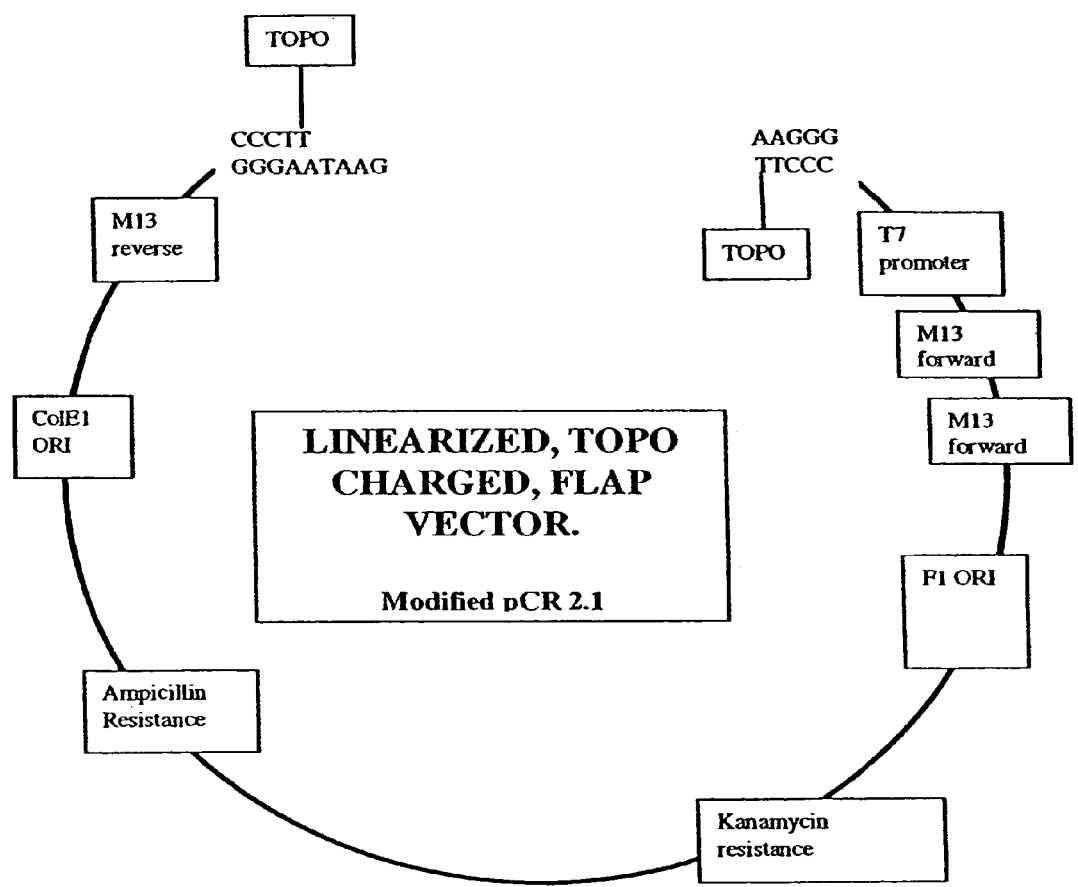

FIG. 15 illustrates a second example of a linearized topoisomerase-charged ds nucleic acid cloning vector of the present invention. In this example the single stranded overhang sequence is 3'-TAAG-5'. This vector is the linearized, TOPO charged, FLAP vector, modified pCR2.1®.

Figure 16:
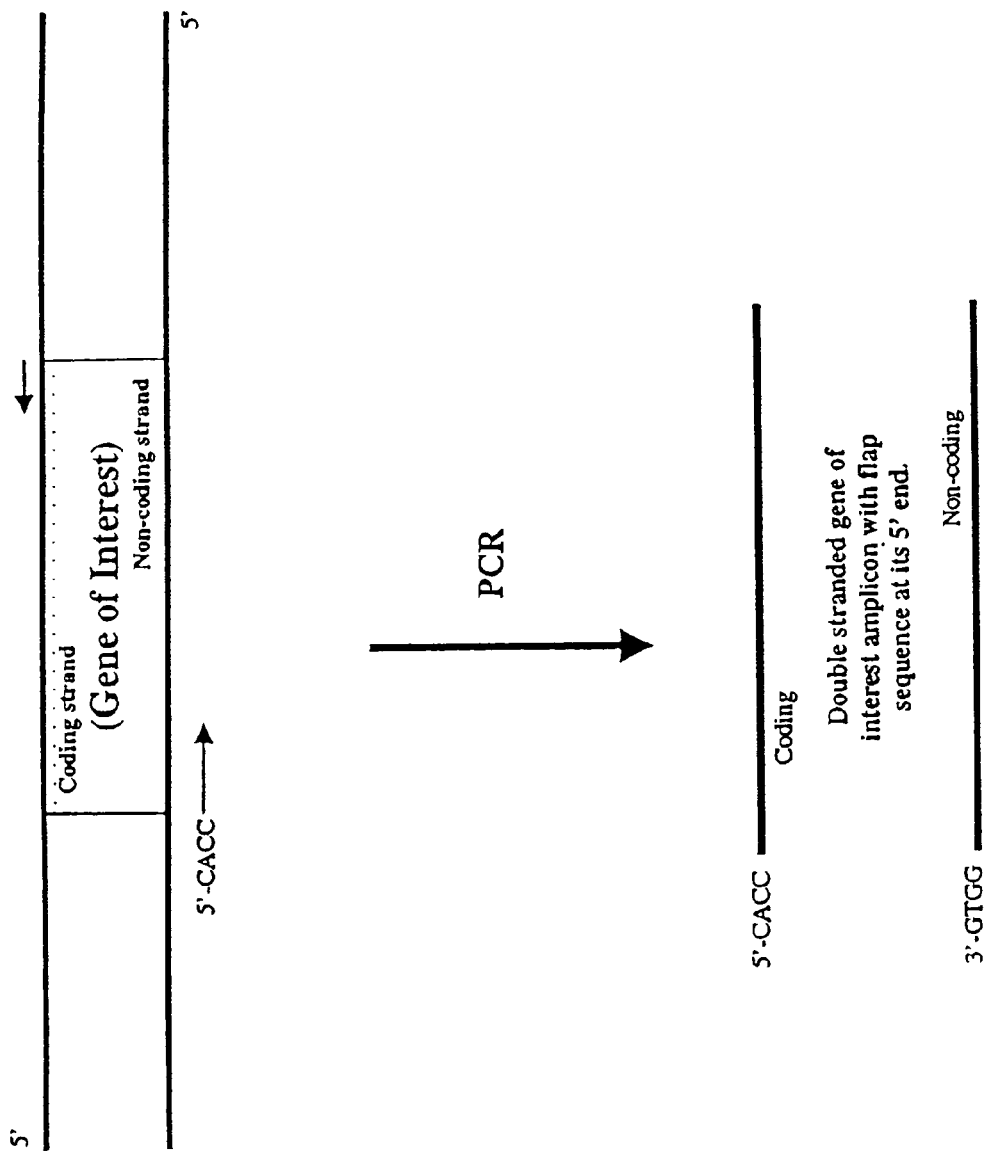

FIG. 16 illustrates PCR amplification of a gene of interest using primers designed for directional cloning. The resulting product possesses the necessary single stranded overhang for directional cloning using a vector of the invention. The primer CACC depicted in the top illustration is homologous to the coding strand of the gene of interest, and has the "FLAP" sequence added to its 5' end. Standard PCR amplification of the gene of interest in the presence of the appropriate primers, including the CACC containing primer, gives the product depicted in the bottom illustration. The product is a double stranded gene of interest amplicon with flap sequence at its 5' end.

Figure 17:
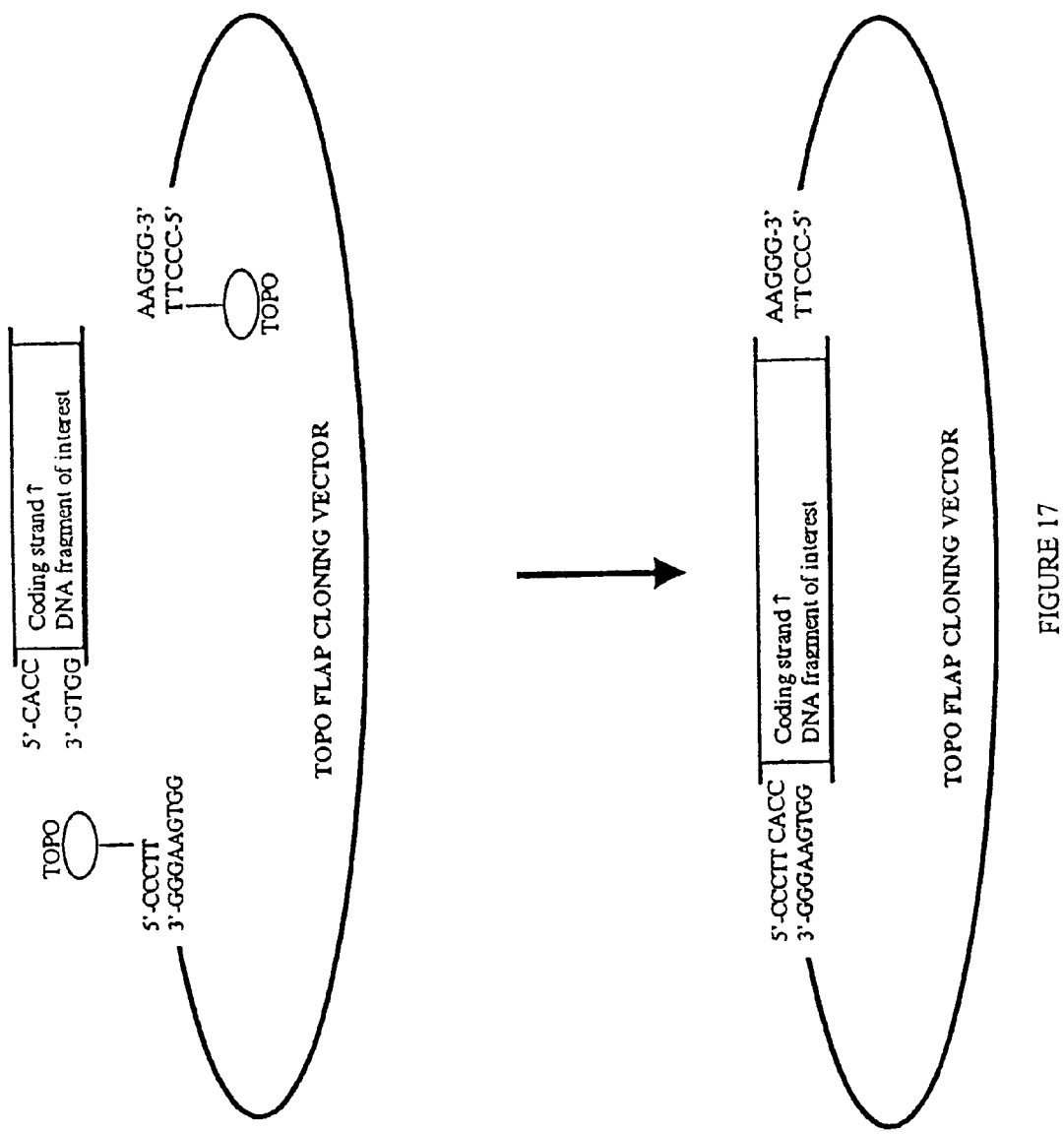

FIG. 17 illustrates double stranded nucleic acid vectors of the present invention, including a TOPO FLAP cloning vector, which possesses a single stranded overhang, can facilitate insertion of amplified DNA towards proper orientation. Once correctly inserted, topoisomerase will ligate the product to the vector.

DETAILED DESCRIPTION OF THE INVENTION

The present invention provides compositions and methods of using strand invasion to directionally or non-directionally link two or more double stranded (ds) nucleic acid molecules. For example, the present invention provides a ds nucleic acid molecule having a first end and a second end, wherein the first end contains a first 5' overhang and a first topoisomerase covalently bound at the 3' terminus, and the second end contains a second topoisomerase covalently bound at the 3' terminus and contains a second 5' overhang, a blunt end, a 3' uridine overhang, or a 3' thymidine overhang, wherein the first 5' overhang is different from the second 5' overhang. The first topoisomerase and second topoisomerase can be the same or different. The first 5' overhang can have any nucleotide sequence, including, for example, the nucleotide sequence 5-GGTG.

Aspects of the present invention modify topoisomerase-mediated cloning so as to allow DNA fragments, including PCR-generated ORFs, to be directionally inserted into cloning vectors, while maintaining the advantages provided by ligation using topoisomerase. The system greatly reduces the amount of work involved in screening to identify clones containing inserts in the desired orientation by enabling directional cloning efficiencies that are routinely in excess of 90%. The present invention streamlines high throughput gene expression operations and reduces costs associated with the screening process, and provides additional advantages.

A topoisomerase-charged ds nucleic acid molecule of the invention generally has a single stranded overhang and a first topoisomerase covalently bound at or near a terminus of a first end. In addition, a topoisomerase-charged ds nucleic acid molecule of the invention can include a second topoisomerase covalently bound at or near a terminus of the second end. The single stranded overhang can be a 5' overhang, and each topoisomerase can be bound at or near one or both 3' termini. Where a topoisomerase is bound to one, or preferably both, 3' termini, the second end of the topoisomerase-charged ds nucleic acid molecule of the present invention typically is a blunt end, a 3' thymidine overhang, or a second 5' overhang that is different from the first 5' overhang.

As used herein, reference to a nucleic acid molecule having "a first end" and "a second end" means that the nucleic acid molecule is linear. The term "single stranded overhang" or "overhang" is used herein to refer to a strand of a ds nucleic acid molecule that extends beyond the terminus of the complementary strand of the ds nucleic acid molecule. The term "5' overhang" or "5' overhanging sequence" is used herein to refer to a strand of a ds nucleic acid molecule that extends in a 5' direction beyond the 3' terminus of the complementary strand of the ds nucleic acid molecule. The term "3' overhang" or "3' overhanging sequence" is used herein to refer to a strand of a ds nucleic acid molecule that extends in a 3' direction beyond the 5' terminus of the complementary strand of the ds nucleic acid molecule. Conveniently, a 5' overhang can be produced as a result of site specific cleavage of a ds nucleic acid molecule by a type IB topoisomerase (see Examples 1 and 2). Similarly, a 3' overhang can be produced upon cleavage of a ds nucleic acid molecule by a type IA or type II topoisomerase.

The 3' overhang and 5' overhang can have any nucleotide sequence and can be any length (e.g., 2, 3, 4, 5, 6, 7, 8, 9, 10, etc. nucleotides), but will generally be at least two nucleotides. The overhanging sequences can be selected such that the allow ligation of a predetermined end of one ds nucleic acid molecule to a predetermined end of a second nucleic acid molecule according to a method of the invention. Where the double stranded nucleic acid molecules are directionally linked, the 3' or 5' overhangs are generally not palindromic because ds nucleic acid molecules having palindromic overhangs can associate with each other, thus reducing the yield of a directionally linked recombinant nucleic acid molecule comprising two or more ds nucleic acid molecules in a predetermined orientation. The overhang can comprise, for example, a nucleotide sequence of a transcriptional or translational regulatory element such as a promoter, Kozak sequence, start codon, or the like, or a complement of such a nucleotide sequence."

A 3' overhang or 5' overhang can include virtually any nucleotide or nucleotide analog or modified nucleotide that can hybridize with a complementary nucleotide residue, provided that at least a portion of the nucleotide sequence of the overhang can hybridize with the complementary sequence. Thus, the nucleosides in a overhang can include naturally occurring nucleotides such as purines (guanosine (G) or adenosine (A)), or pyrimidines (thymidine (T), uridine (U) or cytidine (C)). Additionally, the overhang can include substitutes for the nucleosides, for example, a nucleoside such as inosine, or a modified form of a nucleoside such as methyl guanosine, or a 5-halogenated pyrimidine nucleoside (e.g., 5-bromodeoxy uridine or 5-methyl deoxycytidine). If desired, the overhang can have a relatively high GC content, for example, the overhang can have a greater than 50% GC content, such as 66% GC or 75% GC or 80% GC or 100% GC content. In one embodiment, the overhang has the sequence 5-GGTG-3'.

A 5' or 3' overhang of a first nucleic acid molecule, for example, can include one or two or a few nucleotide residues, for example, at the free terminus of the overhang, for which a complementary nucleotide residue is not present in the complementary sequence at or near the substantially blunt end of the second (or other) ds nucleic acid molecule to which it is being linked. Nevertheless, the overhang at the end of the first nucleic acid molecule can selectively hybridize to the complementary sequence of the second nucleic acid molecule due to the other nucleotide residues in the overhang. For example, where a 5' overhang consists of six nucleotides, the 5'-most one or two nucleotides need not be complementary to the corresponding nucleotides in the complementary nucleotide sequence in the second nucleic acid molecule, but selective hybridization nevertheless can occur due to the complementarity of the remaining four nucleotide residues. The number or specific positions of non-complementary nucleotide residues that can be in an overhang (or in the "complementary" sequence in the second nucleic acid molecule) without substantially reducing or inhibiting hybridization specificity can be determined using routine hybridization methods.

The nucleotide residues of the overhang can include locked nucleic acid ("LNA") analogues (Proligo; Boulder Colo.). LNA monomers are bicyclic compounds that are structurally similar to ribonucleosides. The term "Locked Nucleic Acid" was coined to emphasize that the furanose ring conformation is restricted in an LNA by a methylene linker that connects the 2'-O position to the 4'-C position. As used herein, all nucleic acid molecules containing one or more LNA modifications are referred to as LNA molecules. LNA oligomers obey Watson-Crick base pairing rules and hybridize to complementary oligonucleotides. LNA can provide vastly improved hybridization, stability, and increased thermal stability performance when compared to DNA and other nucleic acid derivatives in a number of situations (Koshkin et al., *Tetrahedron* 54:3607-30, 1998; Koshkin et al., *J. Am. Chem. Soc.* 120:13252-53, 1998; Wahlestedt et al., *Proc. Natl. Acad. Sci., USA* 97:5633-38, 2000).

It should be recognized that reference to a first end or a second end of a ds nucleic acid molecule is not intended to imply any particular orientation of the nucleic acid molecule, and is not intended to imply a relative importance of the ends with respect to each other. Where a nucleic acid molecule having a first end and second end is a double stranded nucleic acid molecule, each end contains a 5' terminus and a 3' terminus. Thus, reference is made herein, for example, to a nucleic acid molecule containing a topoisomerase recognition site at a 3' terminus and a hydroxyl group at the 5' terminus of the same end, which can be the first end or the second end.

Topoisomerase when bound to a nucleic acid molecule, will generally be bound "at or near" a terminus of a ds nucleic acid molecule. The term "at or near" when used with respect to a topoisomerase, means that the topoisomerase is covalently bound to one strand of a ds nucleic acid molecule such that it can ligate the terminus of the strand to which it is bound, to a second nucleic acid molecule containing a free 5' terminal hydroxyl group. Generally, the topoisomerase is "at or near" an end by virtue of being covalently bound to one terminus of the end. For example, where the topoisomerase is a type IB topoisomerase such as a Vaccinia topoisomerase, the topoisomerase is bound at the 3' terminus of an end of a ds nucleic acid molecule. However, an end having a topoisomerase covalently bound to a terminus of the end also can contain a single stranded overhang sequence in the complementary strand, thus extending beyond the terminus to which the topoisomerase is bound. Such a topoisomerase is an example of a topoisomerase near an end of the ds nucleic acid molecule.

As used herein, the term "isolated," when used in reference to a molecule, means that the molecule is in a form other than that in which it exists in nature. In general, an isolated nucleic acid molecule, for example, can be any nucleic acid molecule that is not part of a genome in a cell, or is separated physically from a cell that normally contains the nucleic acid molecule. It should be recognized that various compositions of the invention comprise a mixture of isolated ds nucleic acid molecules. As such, it will be understood that the term "isolated" only is used in respect to the isolation of the molecule from its natural state, but does not indicate that the molecule is an only constituent.

Topoisomerases are a class of enzymes that modify the topological state of DNA via the breakage and rejoining of DNA strands (Shuman et al., U.S. Pat. No. 5,766,891, incorporated herein by reference). Topoisomerases are categorized as type I, including type IA and type IB topoisomerases, which cleave a single strand of a double stranded nucleic acid molecule, and type II topoisomerases (gyrases), which cleave both strands of a nucleic acid molecule. As disclosed herein, type I and type II topoisomerases, as well as catalytic domains and mutant forms thereof, are useful for generating directionally linked recombinant nucleic acid molecules according to a method of the invention. Type II topoisomerases have not generally been used for generating recombinant nucleic acid molecules or cloning procedures, whereas type IB topoisomerases, are used in a variety of procedures.

Type IA and IB topoisomerases cleave one strand of a ds nucleic acid molecule. Cleavage of a ds nucleic acid molecule by type IA topoisomerases generates a 5' phosphate and a 3' hydroxyl at the cleavage site, with the type IA topoisomerase covalently binding to the 5' terminus of a cleaved strand. In comparison, cleavage of a ds nucleic acid molecule by type IB topoisomerases generates a 3' phosphate and a 5' hydroxyl at the cleavage site, with the type IB topoisomerase covalently binding to the 3' terminus of a cleaved strand. Type IA topoisomerases include, for example, *E. coli* topoisomerase I and topoisomerase III, eukaryotic topoisomerase II, and archeal reverse gyrase (see Berger, *Biochim. Biophys. Acta* 1400:3-18, 1998, which is incorporated herein by reference).

Type IB topoisomerases include the nuclear type I topoisomerases present in all eukaryotic cells and those encoded by Vaccinia and other cellular poxviruses (see Cheng et al., *Cell* 92:841-850, 1998, which is incorporated herein by reference). The eukaryotic type IB topoisomerases are exemplified by those expressed in yeast, *Drosophila* and mammalian cells, including human cells (see Caron and Wang, *Adv. Pharmacol.* 29B:271-297, 1994; Gupta et al., *Biochim. Biophys. Acta* 1262:1-14, 1995, each of which is incorporated herein by reference; see, also, Berger, supra, 1998). Viral type IB topoisomerases are exemplified by those produced by the vertebrate poxviruses (Vaccinia, Shope fibroma virus, ORF virus, fowlpox virus, and molluscum contagiosum virus), and the insect poxvirus (Amsacta moorei entomopoxvirus) (see Shuman, *Biochim. Biophys. Acta* 1400:321-337, 1998; Petersen et al., *Virology* 230:197-206, 1997; Shuman and Prescott, *Proc. Natl. Acad. Sci., USA* 84:7478-7482, 1987; Shuman, *J. Biol. Chem.* 269:32678-32684, 1994; U.S. Pat. No. 5,766,891; PCT/US95/16099; PCT/US98/12372, each of which is incorporated herein by reference; see, also, Cheng et al., supra, 1998).

Type II topoisomerases include, for example, bacterial gyrase, bacterial DNA topoisomerase IV, eukaryotic DNA topoisomerase II, and T-even phage encoded DNA topoisomerases (Roca and Wang, *Cell* 71:833-840, 1992; Wang, *J. Biol. Chem.* 266:6659-6662, 1991, each of which is incorporated herein by reference; Berger, supra, 1998). Like the type IB topoisomerases, the type II topoisomerases have both cleaving and ligating activities. In addition, like type IB topoisomerase, substrate ds nucleic acid molecules can be prepared such that the type II topoisomerase can form a covalent linkage to one strand at a cleavage site. For example, calf thymus type II topoisomerase can cleave a substrate ds nucleic acid molecule containing a 5' recessed topoisomerase recognition site positioned three nucleotides from the 5' end, resulting in dissociation of the three nucleic acid molecule 5' to the cleavage site and covalent binding of the topoisomerase to the 5' terminus of the ds nucleic acid molecule (Andersen et al., supra, 1991). Furthermore, upon contacting such a type II topoisomerase-charged ds nucleic acid molecule with a second nucleic acid molecule containing a 3' hydroxyl group, the type II topoisomerase can ligate the sequences together, and then is released from the recombinant nucleic acid molecule. As such, type II topoisomerases also are useful for performing methods of the invention.

Structural analysis of topoisomerases indicates that the members of each particular topoisomerase families, including type IA, type IB and type II topoisomerases, share common structural features with other members of the family (Berger, supra, 1998). In addition, sequence analysis of various type IB topoisomerases indicates that the structures are highly conserved, particularly in the catalytic domain (Shuman, supra, 1998; Cheng et al., supra, 1998; Petersen et al., supra 1997). For example, a domain comprising amino acids 81 to 314 of the 314 amino acid Vaccinia topoisomerase shares substantial homology with other type IB topoisomerases, and the isolated domain has essentially the same activity as the full length topoisomerase, although the isolated domain has a slower turnover rate and lower binding affinity to the recognition site (see Shuman, supra, 1998; Cheng et al., supra, 1998). In addition, a mutant Vaccinia topoisomerase, which is mutated in the amino terminal domain (at amino acid residues 70 and 72) displays identical properties as the full length topoisomerase (Cheng et al., supra, 1998). In fact, mutation analysis of Vaccinia type IB topoisomerase reveals a large number of amino acid residues that can be mutated without affecting the activity of the topoisomerase, and has identified several amino acids that are required for activity (Shuman, supra, 1998). In view of the high homology shared among the Vaccinia topoisomerase catalytic domain and the other type IB topoisomerases, and the detailed mutation analysis of Vaccinia topoisomerase, it will be recognized that isolated catalytic domains of the type IB topoisomerases and type IB topoisomerases having various amino acid mutations can be used in the methods of the invention and thus are considered to be topoisomerases for purposes of the present invention.

The various topoisomerases exhibit a range of sequence specificity. For example, type II topoisomerases can bind to a variety of sequences, but cleave at a highly specific recognition site (see Andersen et al., *J. Biol. Chem.* 266:9203-9210, 1991, which is incorporated herein by reference.). In comparison, the type IB topoisomerases include site specific topoisomerases, which bind to and cleave a specific nucleotide sequence ("topoisomerase recognition site"). Upon cleavage of a ds nucleic acid molecule by a topoisomerase, for example, a type IB topoisomerase, the energy of the phosphodiester bond is conserved via the formation of a phosphotyrosyl linkage between a specific tyrosine residue in the topoisomerase and the 3' nucleotide of the topoisomerase recognition site. Where the topoisomerase cleavage site is near the 3' terminus of the nucleic acid molecule, the downstream sequence (3' to the cleavage site) can dissociate, leaving a nucleic acid molecule having the topoisomerase covalently bound to the newly generated 3' end (see FIG. 9).

The covalently bound topoisomerase also can catalyze the reverse reaction, for example, covalent linkage of the 3' nucleotide of the recognition sequence, to which a type IB topoisomerase is linked through the phosphotyrosyl bond, and a nucleic acid molecule containing a free 5' hydroxyl group. As such, methods have been developed for using a type IB topoisomerase to produce recombinant nucleic acid molecules. As such, cloning vectors containing a bound type IB topoisomerase have been developed and are commercially available (Invitrogen Corp., Carlsbad Calif.). Such cloning vectors, when linearized, contain a covalently bound type IB topoisomerase at each 3' end ("topoisomerase-charged"). Nucleic acid molecules such as those comprising a cDNA library, or restriction fragments, or sheared genomic DNA sequences that are to be cloned into such a vector are treated, for example, with a phosphatase to produce 5' hydroxyl termini, then are added to the linearized vector under conditions that allow the topoisomerase to ligate the nucleic acid molecules at the 5' terminus containing the hydroxyl group and the 3' termilus containing the covalently bound topoisomerase. A nucleic acid molecule such as a PCR amplification product, which is produced containing 5' hydroxyl ends, can be cloned into a topoisomerase-charged vector in a rapid joining reaction (approximately 5 min at room temperature). The rapid joining and broad temperature range inherent to the topoisomerase joining reaction makes the use of topoisomerase-charged vectors ideal for high throughput applications, which generally are performed using automated systems.

Vaccinia virus encodes a 314 amino acid type I topoisomerase enzyme capable of site-specific single-strand nicking of double stranded DNA, as well as 5' hydroxyl driven religation. Site-specific type I topoisomerases include, but are not limited to, viral topoisomerases such as pox virus topoisomerase. Examples of pox virus topoisomerases include Shope fibroma virus and ORF virus. Other site-specific topoisomerases are well known to those skilled in the art and can be used to practice this invention.

Vaccinia topoisomerase binds to duplex DNA and cleaves the phosphodiester backbone of one strand while exhibiting a high level of sequence specificity. Cleavage occurs at a consensus pentapyrimidine element 5'-(C/T)CCTT↓, or related sequences in the scissile strand. In one embodiment the scissile bond is situated in the range of 2 to 12 bp from the 3' end of the duplex DNA. In another embodiment cleavable complex formation by Vaccinia topoisomerase requires six duplex nucleotides upstream and two nucleotides downstream of the cleavage site. Examples of Vaccinia topoisomerase cleavable sequences include, but are not limited to, +6/−6 duplex G CCCTTATTCCC (SEQ ID NO:1), +8/−4 duplex TCG CCCTTATTC (SEQ ID NO:2), +10/−2 duplex TGTCG CCCTTAT (SEQ ID NO:3), +11/−1 duplex GTGTCG CCCTTA (SEQ ID NO:4).

Examples of other site-specific type I topoisomerases are well known in the art. These enzymes are encoded by many organisms including, but not limited to *Saccharomyces cerevisiae, Saccharomyces pombe* and *Tetrahymena*, however, the topoisomerase I enzymes of these species have less specificity for a consensus sequence than does the Vaccinia topoisomerase. (Lynn et al., *Proc. Natl. Acad. Sci. USA* 86: 3559-3563, 1989; Eng et al., *J. Biol. Chem.* 264: 13373-13376, 1989; Busk et al., *Nature* 327: 638-640, 1987).

The compositions and methods of the invention are exemplified generally herein with reference to the use of type IB topoisomerase such as the Vaccinia topoisomerase. However, it will be recognized that the methods also can be performed using other topoisomerases merely by adjusting the components accordingly. For example, as described in greater detail below, methods are disclosed for incorporating a type IB topoisomerase recognition site at one or both 3' termini of a ds nucleic acid molecule. Accordingly, in view of the present disclosure, the artisan will recognize that a topoisomerase recognition site for a type IA or type II topoisomerase similarly can be incorporated into a ds nucleic acid molecule.

A topoisomerase-charged ds nucleic acid molecule that contains a 5' overhang on a first end generally contains a topoisomerase covalently bound to the 3' terminus of the first end. A ds nucleic acid containing a 5' overhang and first topoisomerase at a first end, also can contain a second topoisomerase covalently bound to the second end. The topoisomerase covalently bound to the first end can be the same as or different from the topoisomerase covalently bound to the second end. Thus, a Vaccinia topoisomerase can be covalently bound to a first end and another poxvirus or eukaryotic nuclear type IB topoisomerase can be bound to the second end. Generally, where the topoisomerases at each end are different, they are members of the same general family, for example, type IA or type IB or type II topoisomerase.

In one embodiment, a topoisomerase-charged double stranded nucleic acid molecule of the invention is a vector, which can be a cloning vector or an expression vector. The vector can include elements such as a bacterial origin of replication, a eukaryotic origin of replication, antibiotic resistance genes, and the like, and can further include topoisomerase recognition sites or topoisomerase-charged ends or a combination thereof. Such vectors of the invention can conveniently be packaged into kits as disclosed herein. A vector of the invention can be a plasmid vector, a cosmid vector, an artificial chromosome (e.g., a bacterial artificial chromosome, a yeast artificial chromosome, a mammalian artificial chromosome, etc.) or a viral vector such as a bacteriophage, baculovirus, retrovirus, lentivirus, adenovirus, Vaccinia virus, semliki forest virus and adeno-associated virus vector, all of which are well known and can be purchased from commercial sources (Promega, Madison Wis.; Stratagene, La Jolla Calif.; GIBCO/BRL, Gaithersburg Md.). Viral expression vectors can be particularly useful where a method of the invention is practiced for the purpose of generating a directionally linked recombinant nucleic acid molecule that is to be introduced into a cell, particularly a cell in a subject. Viral vectors provide the advantage that they can infect host cells with relatively high efficiency and can infect specific cell types or can be modified to infect particular cells in a host.

Viral vectors have been developed for use in particular host systems and include, for example, baculovirus vectors, which infect insect cells; retroviral vectors, other lentivirus vectors such as those based on the human immunodeficiency virus (HIV), adenovirus vectors, adeno-associated virus (AAV) vectors, herpesvirus vectors, Vaccinia virus vectors, and the like, which infect mammalian cells (see Miller and Rosman, *BioTechniques* 7:980-990, 1992; Anderson et al., *Nature* 392: 25-30 Suppl., 1998; Verma and Somia, *Nature* 389:239-242, 1997; Wilson, *New Engl. J. Med.* 334:1185-1187, 1996, each of which is incorporated herein by reference). For example, a viral vector based on an HIV can be used to infect T cells, a viral vector based on an adenovirus can be used, for example, to infect respiratory epithelial cells, and a viral vector based on a herpesvirus can be used to infect neuronal cells. Other vectors, such as AAV vectors can have greater host cell range and, therefore, can be used to infect various cell types, although viral or non-viral vectors also can be modified with specific receptors or ligands to alter target specificity through receptor mediated events.

A linearized vector of the invention, which is topoisomerase-charged or contains topoisomerase recognition sites can be generated using methods as disclosed herein or otherwise known in the art. For example, a circular vector can be linearized, and modified by ligating or hybridizing one or more oligonucleotides, to generate a topoisomerase recognition site, or a cleavage product thereof, and a target 5' sequence or 5' overhang, at one or both ends (see Examples 1 and 2). The vector also can contain, for example, expression control elements required for replication in a prokaryotic host cell, a eukaryotic host cell, or both, and can contain a nucleotide sequence encoding a polypeptide that confers antibiotic resistance or the like, or such elements can be introduced into the vector using the methods of the invention. Furthermore, the vector can contain one, two, or more site specific integration recognition site such as an att site or lox site. The incorporation, for example, of attB or attP sequences into an isolated nucleic acid molecule of the present invention allows for the convenient manipulation of the nucleic acid molecule using the GATEWAY™ Cloning System (Invitrogen Corp., La Jolla Calif.).

The invention provides a modified cloning vector having an overhanging single stranded piece of DNA charged with topoisomerase. The modified vector allows the directional insertion of linear ds nucleic acid molecules, for example PCR amplified, or otherwise suitable ORFs, for subsequent expression, and takes advantage of topoisomerase cloning efficiency. As used herein, the term donor signifies molecules such as a duplex DNA which contains a 5'-CCCTT cleavage site near the 3' end, and the term acceptor signifies a duplex DNA which contains a 5'—OH terminus. Once covalently activated by topoisomerase the donor will be transferred to those acceptors to which it has single strand sequence complementation.

According to the present invention, in particular embodiments topoisomerase-modified vectors are further adapted to contain at least one 5' single-stranded overhang sequence to facilitate the directional insertion of DNA segments. A nucleic acid molecule to be cloned into such a vector can be a PCR product constituting an ORF, which can be expressed from the resultant recombinant vector. The primers used for amplifying the ORF are designed such that at least one primer of the primer pair contains an additional sequence at its 5' end. This sequence is designed to be complementary to the sequence of the 5' single-stranded overhang present in the topoisomerase-modified vector of the present invention.

The present invention generally provides methods for generating a directionally or non-directionally linked recombinant nucleic acid molecule, by using a strand invasion event and a ligation event to link, in a directional or non-directional manner, a first nucleic acid molecule and at least a second nucleic acid molecule. As used herein, the term "strand invasion" refers to the displacement of one strand of a first double stranded nucleic acid molecule by a single stranded portion of a second nucleic acid molecule, wherein the single strand has nucleotide sequence that is substantially identical to the displaced strand and can selectively hybridize to the strand complementary to the displaced strand.

A method for generating a directionally or non-directionally linked recombinant nucleic acid molecule can be performed, for example, by contacting a first ds nucleic acid molecule having a first overhang on a first strand (e.g., a 3' or 5' strand) at a first end; and a second ds nucleic acid molecule having a first substantially blunt end and a second end, wherein a nucleotide sequence that is complementary to the first overhang of the first end of the first nucleic acid molecule, is present at or near the first substantially blunt end. The method is performed under conditions such that the first overhang can selectively hybridize to the complementary nucleotide sequence of the first substantially blunt end of the second ds nucleic acid molecule, and the first end of the first ds nucleic acid molecule and the first end of the second ds nucleic acid molecule can be linked. The first overhang can be a 3' overhang or a 5' overhang. The invention further provides precursor nucleic acid molecules which can be used to prepare molecules suitable for use in the method described above. The invention also provides nucleic acid molecules prepared by the above method.

Figure 1:
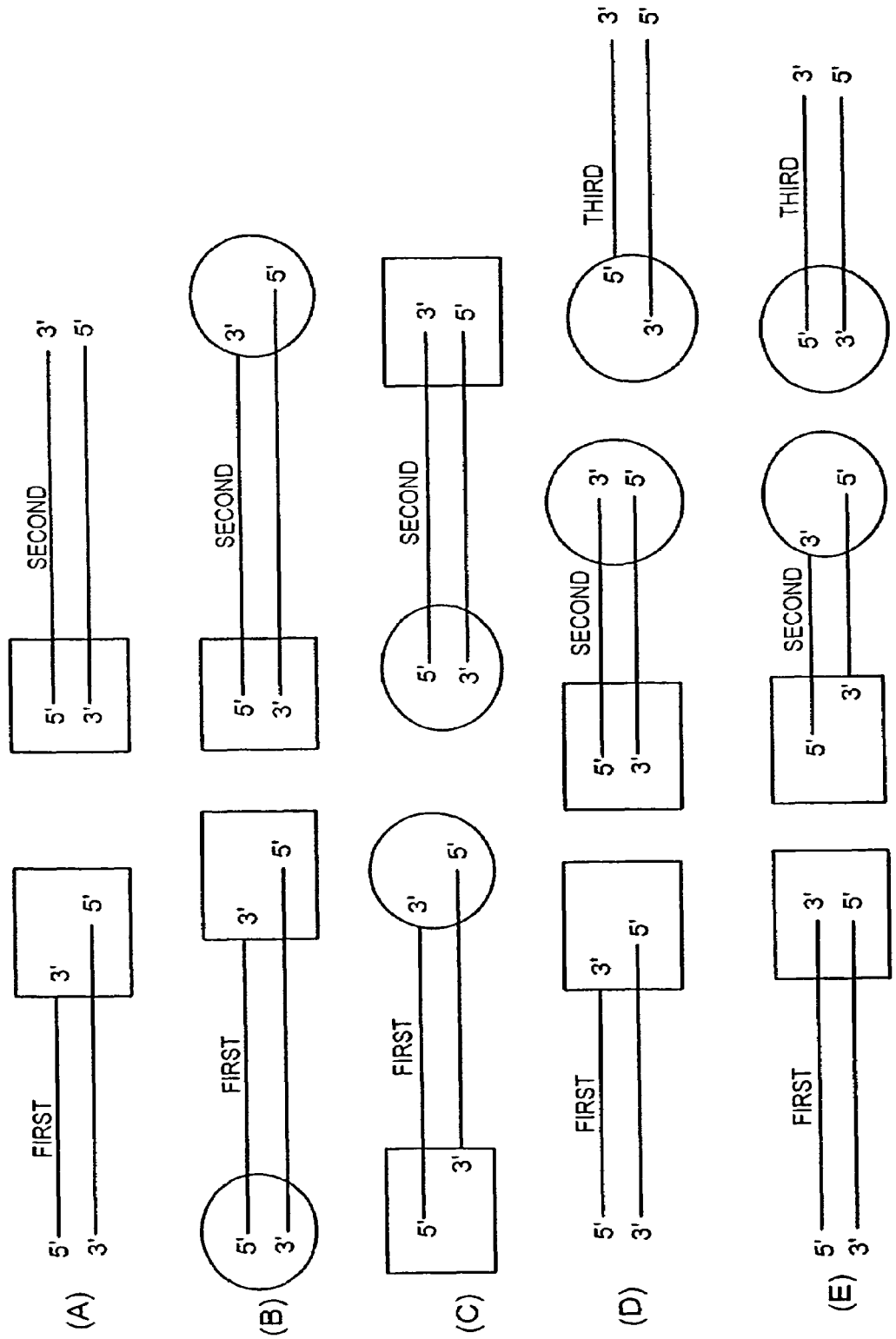
FIGS. 1A to 1E depict a number of ds nucleic acid molecules that can be used to practice various aspects of the invention. The circled and boxed areas shown in these depictions indicate regions which contain sufficient nucleotide sequence complementarity to engage in strand invasion with each other.

FIG. 1 illustrates examples of ways in which the methods of the invention can be used to generate a covalently linked recombinant nucleic acid molecule. The boxes and circles in FIG. 1 are used to depict regions of sequence complementarity such that a strand displacement event can occur. The other end of the ds nucleic acid molecules, which do not necessarily (but can) involve a strand displacement event, can have any structure, including, can be substantially blunt or can include a 3' or 5' overhang. Other combinations of blunt ends and/or overhangs on the first, second, third, etc. ds nucleic acid molecules can be linked according to the methods of the invention and will be evident to those in the art based, in part, on the examples provided in FIG. 1.

As shown in FIG. 1A, a method for generating a directionally or non-directionally linked recombinant nucleic acid molecule can be performed, for example, by contacting a first ds nucleic acid molecule, which has a first overhang on a first strand at a first end; a second ds nucleic acid molecule, which has a first substantially blunt end and a second end, wherein the first substantially blunt end has a nucleotide sequence that is complementary to the first overhang of the first end of the first nucleic acid molecule; and a reagent for ligating the nucleic acid molecules (e.g., a reagent comprising a topoisomerase, a ligase, or a recombinase). The method is performed under conditions such that the first overhang can selectively hybridize to the complementary nucleotide sequence of the first substantially blunt end of the second ds nucleic acid molecule. Furthermore, the method is performed in the presence of a reagent that can ligate a 5' strand of one nucleic acid molecule to a 3' strand of a second nucleic acid molecule, and under conditions such that the 3' terminus of the first end of the first ds nucleic acid molecule and the 5' terminus of the first end of the second ds nucleic acid molecule are linked. In various modifications of the method described above, as well as in other methods described above, the first overhang can be a 3' overhang or a 5' overhang.

As shown in FIG. 1B, a method for generating a linked, for example directionally linked, recombinant nucleic acid molecule can be performed by contacting a first ds nucleic acid molecule with a first overhang on a first strand at a first end and a second substantially blunt end; and a second ds nucleic acid molecule, which has a first substantially blunt end and a second end which has a second overhang, wherein the first substantially blunt end of the second ds nucleic acid molecule has a nucleotide sequence that is complementary to the first overhang of the first end of the first nucleic acid molecule, and wherein the second substantially blunt end of the first nucleic acid molecule has a nucleotide sequence that is complementary to the second overhang of the second end of the second ds nucleic acid molecule. The method is performed under conditions such that the first overhang can selectively hybridize to the complementary nucleotide sequence of the first substantially blunt end of the second ds nucleic acid molecule, and wherein the second overhang can selectively hybridize to the complementary nucleotide sequence of the second substantially blunt end of the first ds nucleic acid molecule.

Furthermore, the method may be performed in the presence of a reagent which can catalyze the ligation of a 3' strand of one nucleic acid molecule to a 5' strand of another nucleic acid molecule, and under conditions such that the 3' terminus of the first end of the first ds nucleic acid molecule is linked to the 5' terminus of the first end of the second ds nucleic acid molecule, and the 3' terminus of the second substantially blunt end of the first ds nucleic acid molecule is linked to the 5' terminus of the second end of the second ds nucleic acid molecule. In various modifications of the method described above, one or both the first and second overhangs can be 3' overhangs or 5' overhangs. The ds nucleic acid molecules can thus engage in two separate strand invasion events which, upon covalent linkage of nucleic acid strands at each termini, result in the formation of a circular recombinant nucleic acid molecule.

As shown in FIG. 1C, a method for generating a linked, for example directionally linked, recombinant nucleic acid molecule can be performed, for example, by contacting a first ds nucleic acid molecule with a first overhang on a first strand at a first end and a second end having a second overhang; and a second ds nucleic acid molecule, which has a first substantially blunt end and a second substantially blunt end, wherein the first substantially blunt end of the second ds nucleic acid molecule has a nucleotide sequence that is complementary to the first overhang of the first end of the first nucleic acid molecule, and wherein the second substantially blunt end of the second nucleic acid molecule has a nucleotide sequence that is complementary to the second overhang of the second end of the first ds nucleic acid molecule. The method may be performed under conditions such that the first overhang can selectively hybridize to the complementary nucleotide sequence of the first substantially blunt end of the second ds nucleic acid molecule, and wherein the second overhang can selectively hybridize to the complementary nucleotide sequence of the second substantially blunt end of the second ds nucleic acid molecule. Furthermore, the method is performed under conditions such that the first end of the first ds nucleic acid molecule is linked to the first end of the second ds nucleic acid molecule, and the second end of the first ds nucleic acid molecule is linked to the second substantially blunt end of the second ds nucleic acid molecule. In various modifications of the method described above, one or both the first and second overhangs can be 3' overhangs or 5' overhangs. The ds nucleic acid molecules can thus engage in two separate strand invasion events, which, upon covalent linkage of nucleic acid strands at each termini, result in the formation of a circular recombinant nucleic acid molecule.

As shown in FIG. 1D, a method for generating a linked, for example directionally linked, recombinant nucleic acid molecule can be performed, for example, by contacting a first ds nucleic acid molecule, which has a first overhang on a first strand at a first end; a second ds nucleic acid molecule, which has a first substantially blunt end and a second substantially blunt end; and a third ds nucleic acid molecule which has a second overhang on a first strand at a first end, wherein the first substantially blunt end of the second ds nucleic acid molecule has a nucleotide sequence that is complementary to the first overhang, and the second substantially blunt end of the second ds nucleic acid molecule has a nucleotide sequence that is complementary to the second overhang. The method is performed under conditions such that the first overhang can selectively hybridize to the complementary nucleotide sequence of the first substantially blunt end of the second ds nucleic acid molecule, and wherein the second overhang can selectively hybridize to the complementary nucleotide sequence of the second substantially blunt end of the second ds nucleic acid molecule. Furthermore, the method may be performed under conditions such that the first end of the first ds nucleic acid molecule is linked to the first end of the second ds nucleic acid molecule, and the first end of the third ds nucleic acid molecule is linked to the second substantially blunt end of the second ds nucleic acid molecule. In various modifications of the method described above, one or both the first and second overhangs can be 3' overhangs or 5' overhangs.

As shown in FIG. 1E, a method for generating a linked, for example directionally linked, recombinant nucleic acid molecule can be performed, for example, by contacting a first ds nucleic acid molecule, which has a first substantially blunt end; a second ds nucleic acid molecule which has a first overhang on a first strand at a first end and a second overhang on a second strand at a second end; and third ds nucleic acid molecule, which has a second substantially blunt end, wherein the first substantially blunt end of the first ds nucleic acid molecule has a nucleotide sequence that is complementary to the first overhang of the first end of the second nucleic acid molecule, and wherein the second substantially blunt end has a nucleotide sequence that is complementary to the second overhang of the second end of the second ds nucleic acid molecule. The method is performed under conditions such that the first overhang can selectively hybridize to the complementary nucleotide sequence of the first substantially blunt end of the first ds nucleic acid molecule, and wherein the second overhang can selectively hybridize to the complementary nucleotide sequence of the second substantially blunt end. Furthermore, the method may be performed under conditions such that the first substantially blunt end of the first ds nucleic acid molecule is linked to the first end of the second ds nucleic acid molecule, and the second substantially blunt end, located on the third ds nucleic acid molecule, is linked to the second end of the second ds nucleic acid molecule. In various modifications of the method described above, one or both the first and second overhangs can be 3' overhangs or 5' overhangs.

Figure 2:
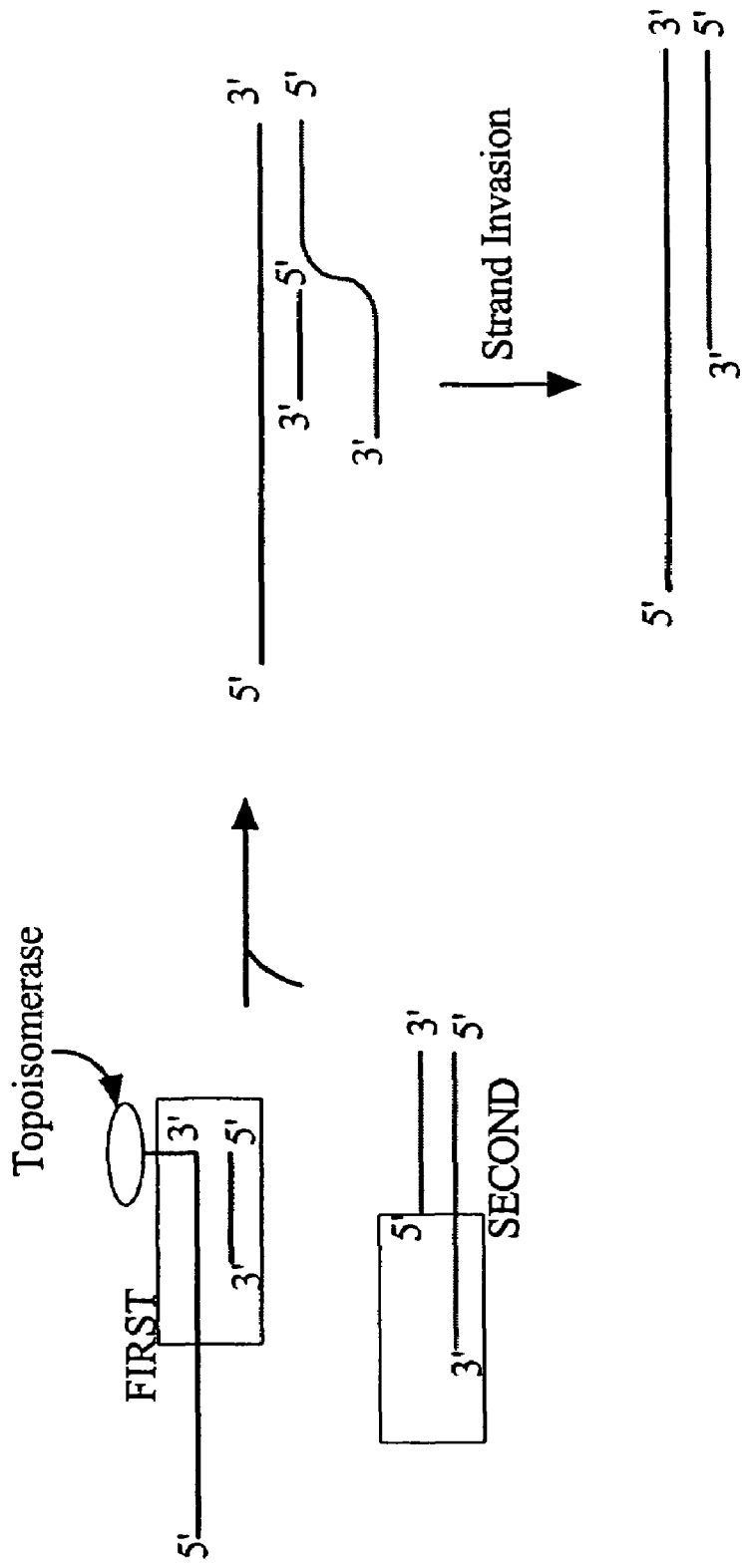
FIG. 2 illustrates an aspect of the invention involving strand invasion of a first ds nucleic acid molecule with a substantially blunt end containing a topoisomerase at a 3' terminus of a first strand containing a 5' tail upstream of a topoisomerase recognition site; and a second ds nucleic acid molecule having a 3' overhang complementary to the 5' tail (see Cheng and Shuman, *Mol. Cell. Biol.* 20:8059-8068, 2000). The boxed areas shown in these depictions indicate regions which contain sufficient nucleotide sequence complementarity to engage in strand invasion with each other.

A method for generating a directionally or non-directionally linked recombinant nucleic acid molecule can be performed, for example, by contacting a first ds nucleic acid molecule, which has a first topoisomerase covalently bound at or near a first substantially blunt end; and a second ds nucleic acid molecule, which has a first 3' overhang on a first strand at a first end, wherein the first substantially blunt end of the first ds nucleic acid molecule has a nucleotide sequence that is complementary to the first 3' overhang (see FIG. 2). The method is performed under conditions such that the first 3' overhang can selectively hybridize to the complementary nucleotide sequence of the first substantially blunt end of the first ds nucleic acid molecule. Furthermore, the method is performed such that topoisomerase can covalently link the 3' terminus of the first end of the first ds nucleic acid molecule to the 5' terminus of the first end of the second ds nucleic acid molecule (Cheng and Shuman, *Mol. Cell. Biol.* 20:8059-8068, 2000, which is incorporated herein by reference in its entirety).

The ability of a topoisomerase covalently bound at or near a first substantially blunt end of a first ds nucleic acid molecule to covalently linked to a second ds nucleic acid molecule with a 3' overhang (FIG. 2) illuminates a previously unappreciated conformational flexibility of covalently bound topoisomerase with respect to its DNA contacts on the 5' side of the scissile phosphodiester. In catalyzing the relaxation of supercoiled DNA, covalently bound topoisomerase type IB releases the downstream duplex and permits rotation of the duplex around the phosphodiester bond opposite the scissile phosphate before resealing the backbone.

A method of the present invention can be performed in a manner that obviates the need to perform an additional reaction to repair a remaining nick after the homology dependent ligation, by substantially replacing one strand of a nucleic acid molecule (see FIG. 2). For example, the methods can be performed such that the overhang sequence of one nucleic acid molecule extends the entire length of and, upon strand invasion, replaces a strand of the other ds nucleic acid molecule. Thus, in this embodiment, there is no nick in the strand that was not ligated by the topoisomerase.

The termini of the ds nucleic acid molecules that are linked using the methods of the current invention can be covalently linked, using any reagent useful for linking a 5' terminus of a one nucleic acid molecule to a 3' terminus of a second nucleic acid molecule. Thus, the reagent for covalently linking the termini can be, for example, a topoisomerase, including a type IA, type IB or type II topoisomerase; a ligase such as T4 DNA ligase; a recombinase, including FLIP recombinase, Int integrase, or cre recombinase; or another INT family member (see, for example, *Nucl. Acids Res.* 26:391-406, 1998). Furthermore, where one nick remains after a ligation of one strand, the nick can be closed by an in vivo ligation, for example by introduction into a cell, such as *E. coli*, of the nicked ds nucleic acid molecule. In certain preferred embodiments, the linking of the two ends involved in a strand displacement event involves topoisomerase ligation. Furthermore, in a method as disclosed for linking a first ds nucleic acid molecule and a second ds nucleic acid molecule, a third nucleic acid molecule also can be linked to an end of the first or second nucleic acid molecule that is not involved in a strand displacement event.

Methods of the present invention can be performed to link a first ds nucleic acid molecule to at least a second ds nucleic acid molecule in a non-directional or, preferably, a directional manner. However, the methods can be used to non-directionally link the first ds nucleic acid molecule and the second ds nucleic acid molecule in embodiments where complementarity exists between nucleotide sequences at or near a terminus of both ends of one of the ds nucleic acid molecules and nucleotide sequences at or near a terminus of at least one end of the other ds nucleic acid molecule. Such complementarity between nucleotide sequences at or near a terminus of both ends of one ds nucleic acid molecule and at least one strand of the second ds nucleic acid molecule can be achieved, for example, by including identical nucleotide sequences at the same terminus (i.e., 5' or 3') of both ends of a ds nucleic acid molecule. This can be accomplished, for example, by designing target sequences that can be cleaved with the same restriction enzyme and which contain the same nucleotide sequence.

The present invention also relates to methods of directionally or non-directionally linking a first and at least a second nucleic acid molecule, including, as desired, operatively linking two or more (e.g., 2, 3, 4, 5, 6, 7, etc.) of the nucleic acid molecules. A method for generating a directionally or non-directionally linked recombinant nucleic acid molecule can be performed, for example, by contacting a topoisomerase-charged first ds nucleic acid molecule, which has a first topoisomerase covalently bound at a first end, and a second topoisomerase covalently bound at a second end, and also contains a 5' overhang at the first end and a blunt end, a 3' uridine overhang, a 3' thymidine overhang, or a second 5' overhang at the second end; and a second ds nucleic acid molecule, which has a first blunt end and a second end, wherein the first blunt end has a 5' nucleotide sequence that is complementary to the first 5' overhang of the first end of the first nucleic acid molecule. The first and second topoisomerases can be the same, for example, two type IB topoisomerases, including two Vaccinia type IB topoisomerases, or can be different, including two type IB topoisomerases from different organisms or a type IB topoisomerase and a type IA or a type II topoisomerase.

In performing a method of the invention, the first and second ds nucleic acid molecules are contacted under conditions such that the 5' nucleotide sequence of the second nucleic acid molecule can selectively hybridize to the first 5' overhang, whereby the first topoisomerase can covalently link the 3' terminus of the first end of the first ds nucleic acid molecule to the 5' terminus of the first end of the second ds nucleic acid molecule, and the second topoisomerase can covalently link the 3' terminus of the second end of the first ds nucleic acid molecule to the 5' terminus of the second end of the second ds nucleic acid molecule, to generate a directionally or non-directionally linked recombinant nucleic acid molecule. Accordingly, the present invention provides a directionally or non-directionally linked recombinant nucleic acid molecule produced by such a method.

As disclosed herein, a method of the invention can provide a means to directionally link two or more ds nucleotides in a predetermined directional orientation. The term "directionally link" is used herein to refer to the covalent linkage of two or more nucleic acid molecules in a particular predetermined order and/or orientation. Thus, a method of the invention provides a means, for example, to covalently link a promoter expression control element upstream of a coding sequence, and to covalently link a polyadenylation signal downstream of the coding region to generate a functional expressible recombinant nucleic acid molecule; or to covalently link two coding sequences such that they can be transcribed and translated in frame to produce a fusion polypeptide. The term "non-directionally link" is used herein to refer to the covalent linkage of two or more nucleic acid molecules in a random order, i.e., either of the first or second end of the nucleic acid molecule can be linked to an end of another nucleic acid molecule.

The term "substantially blunt," when used in reference to an end of a ds nucleic acid molecule, means that the end can be blunt or can have a short overhang that does not reduce or inhibit a strand invasion event by a second nucleic acid molecule having an overhang. For example, a substantially blunt end can include an end having an overhang of 1, 2, or a few nucleotides, provided the overhang at the substantially blunt end does not block strand invasion. For example, the second ds nucleic acid molecule can have a 5' adenosine or 5' inosine overhang.

It should be recognized that reference herein to a "first nucleic acid molecule," "second nucleic acid molecule," "third nucleic acid molecule," and the like, is used only to provide a means to indicate which of several nucleic acid molecules is being referred to. Thus, absent any specifically defined characteristic with respect to a particular nucleic acid molecule, the terms "first," "second," "third" and the like, when used in reference to a nucleic acid molecule, or a population or plurality of nucleic acid molecules, are not intended to indicate any particular order, importance or other information about the nucleic acid molecule. Thus, where an exemplified method refers, for example, to using PCR to amplify a first ds nucleic acid molecule such that the amplification product contains a topoisomerase recognition site at one or both ends, it will be recognized that, similarly, a second (or other) ds nucleic acid molecule also can be so amplified.

The term "at least a second," when used in reference to a ds nucleic acid molecule, means one or more (e.g., 1, 2, 3, 4, 5, 6, 7, 8, 9, 10, etc.) nucleic acid molecules in addition to a first ds nucleic acid molecule. Thus, the term can refer to only a second nucleic acid molecule, or to a second nucleic acid molecule and a third nucleic acid molecule (or more). As such, the term "second (or other) ds nucleic acid molecule" or "second (and other) ds nucleic acid molecules" is used herein in recognition of the fact that the term "at least a second nucleic acid molecule" can refer to a second, third or more nucleic acid molecules. It should be recognized that, unless indicated otherwise, a nucleic acid molecule encompassed within the meaning of the term "at least a second nucleic acid molecule" can be the same or substantially the same as a first nucleic acid molecule. For example, a first and second ds nucleic acid molecule can be the same except that only one of the molecules, for example, the first ds nucleic acid molecule, has a topoisomerase recognition site, or except for having complementary 5' overhanging sequences, for example, produced upon cleavage by a topoisomerase, such that the first and second ds nucleic acid molecules can be directionally linked using a method of the invention. As such, a method of the invention can be used to produce a concatenate of first and second ds nucleic acid molecules, which, optionally, can be interspersed, for example, by a third ds nucleic acid molecule such as an expression control element, and can contain the directionally linked sequences in a predetermined directional orientation, for example, each in a 5' to 3' orientation with respect to each other.

It will be recognized that each of the ds nucleic acid molecules, for example, a sequence referred to as a first ds nucleic acid molecule, generally comprises a population of such nucleic acid molecules, which are identical or substantially identical to each other. Thus, it should be clear that the term "different" is used in comparing, for example, a first (or population of first) ds nucleic acid molecules with a second (and other) ds nucleic acid molecule. As used herein, the term "different," when used in reference to the ds nucleic acid molecules of a composition of the invention, means that the ds nucleic acid molecules share less than 95% sequence identity with each when optimally aligned, generally less than 90% sequence identity, and usually less than 70% sequence identity. Thus, ds nucleic acid molecules that, for example, differ only in being polymorphic variants of each other or that merely contain different 5' or 3' overhanging sequences are not considered to be "different" for purposes of a composition of the invention. In comparison, different ds nucleic acid molecules are exemplified by a first sequence encoding a polypeptide and second sequence comprising a expression control element, or a first sequence encoding a first polypeptide a second sequence encoding a non-homologous polypeptide.

The term "recombinant" is used herein to refer to a nucleic acid molecule that is produced by linking at least two nucleic acid molecules. As such, a recombinant nucleic acid molecule encompassed within or generated according to a method of the invention is distinguishable from a nucleic acid molecule that may be produced in nature, for example, during meiosis. A recombinant nucleic acid molecule generated according to a method of the invention can be identified, for example, by the presence of the complementary nucleic acid sequence in close proximity, generally directly adjacent, and usually directly 3', to a topoisomerase binding site in a double stranded nucleic acid molecule.

As disclosed herein, a method of the invention can be used to directionally or non-directionally link a first ds nucleic acid molecule to a second ds nucleic acid molecule. In many embodiments, the method may be used to directionally link a first ds nucleic acid molecule and a second (or other) ds nucleic acid molecule. However, use of the method to non-directionally link a first ds nucleic acid molecule and a second (or other) ds nucleic acid molecule also provides advantages. Non-directional linking can be performed, for example, 1) where a second nucleotide sequence is present at or near the 5' terminus of the second end of the first ds nucleic acid molecule, which can form all or part of a second overhang, and is capable of hybridizing to the 5' complementary nucleotide sequence of the second ds nucleic acid molecule; and 2) where a nucleotide sequence is present at or near the 5' terminus of both the first end and the second end of the second ds nucleic acid molecule that is capable of hybridizing to the 5' overhang of the first end of the first ds nucleic acid molecule. In these embodiments, the second end of the first ds nucleic acid molecule and the second end of the second ds nucleic acid molecule can be either blunt, or include an overhang.

In another embodiment, a method for generating a directionally or non-directionally linked recombinant nucleic acid molecule can be performed, for example, by contacting a first precursor ds nucleic acid molecule having a first end, which has a first 5' target sequence at the 5' terminus and a topoisomerase recognition site at or near the 3' terminus, and a second end, which has a topoisomerase recognition site at or near the 3' terminus; a second ds nucleic acid molecule having a first blunt end and a second end, wherein the first blunt end has a 5' nucleotide sequence complementary to the 5' target sequence of the first precursor ds nucleic acid molecule; and a topoisomerase that is specific for the topoisomerase recognition site. As used herein, reference to a "precursor" ds nucleic acid molecule means a ds nucleic acid molecule that contains a topoisomerase recognition site and that, upon cleavage by a topoisomerase specific for the recognition site, produces an end having a desired 5' terminal nucleotide sequence, 3' terminal nucleotide sequence, or both. Such a desired end is produced, in part, due to the presence of the 5' target sequence, which, upon cleavage of the ds nucleic acid molecule containing the 5' target sequence, is converted to a 5' nucleotide sequence that allows directionally linking the ds nucleic acid molecule to a second ds nucleic acid molecule.

According to a method of the invention, the first ds nucleic acid molecule, second ds nucleic acid molecule and topoisomerase are contacted under conditions that allow topoisomerase activity, i.e., such that the topoisomerase can bind to and cleave the recognition site, to produce a topoisomerase-charged 3' terminus, and can ligate the 3' terminus to an appropriate 5' terminus. Such conditions also allow hybridization of the portion of the portion of the first 5' target sequence that remains following cleavage by the topoisomerase and the 5' nucleotide sequence of the second ds nucleic acid molecule that is complementary to that portion of the 5' target sequence.

In performing a method of the invention, a precursor ds nucleic acid molecule can be combined in the same reaction vessel and at the same time with the topoisomerase and the second ds nucleic acid molecule before the precursor ds nucleic acid molecule is converted into a topoisomerase-charged ds nucleic acid molecule that can be directionally linked to a second ds nucleic acid molecule. By combining the topoisomerase in the same reaction vessel as the precursor ds nucleic acid and the second nucleic acid, the methods of the present invention are simplified. Alternatively, a first precursor ds nucleic acid molecule can be combined with topoisomerase under conditions that allow topoisomerase cleavage and binding, then a second ds nucleic acid molecule can be added.

A precursor ds nucleic acid molecule can be linear or circular, including supercoiled, and, as a result of cleavage by one or more topoisomerases and, if desired a restriction endonuclease, a linear topoisomerase-charged first ds nucleic acid molecule is produced. For example, a circular ds nucleic acid molecule containing two type IB topoisomerase recognition sites within about 100 nucleotides of each other and in the complementary strands, preferably within about twenty nucleotides of each other and in the complementary strands, can be contacted with a site specific type IB topoisomerase such that each strand is cleaved and the intervening sequence dissociates, thereby generating a linear ds nucleic acid molecule having a topoisomerase covalently bound to each end.

In general, a topoisomerase-charged double stranded nucleic acid, which can be directionally linked to a second or other ds nucleic acid molecule, is generated by contacting topoisomerase with a precursor ds nucleic acid that has at least one topoisomerase recognition site at or near one end and a first target sequence. As used herein, the term "topoisomerase recognition site" means a defined nucleotide sequence that is recognized and bound by a site specific topoisomerase. For example, the nucleotide sequence 5'-(C/T)CCTT-3' is a topoisomerase recognition site that is bound specifically by most poxvirus topoisomerases, including Vaccinia virus DNA topoisomerase I, which then can cleave the strand after the 3'-most thymidine of the recognition site to produce a nucleic acid molecule comprising 5'-(C/T)CCTT-P $O_4$-TOPO, i.e., a complex of the topoisomerase covalently bound to the 3' phosphate through a tyrosine residue in the topoisomerase (see Shuman, *J. Biol. Chem.* 266: 11372-11379, 1991; Sekiguchi and Shuman, *Nucl. Acids Res.* 22:5360-5365, 1994; each of which is incorporated herein by reference; see, also, U.S. Pat. No. 5,766,891; PCT/US95/16099 (WO 96/19497); PCT/US98/12372 (WO 98/56943 )).

An advantage of constructing a precursor ds nucleic acid molecule to comprise, for example, a type IB topoisomerase recognition site about 2 to 15 nucleotides (e.g., 2, 3, 4, 5, 6, 7, 8, 9, 12, 14, 15, or 20 nucleotides) from one or both ends is that a 5' overhang is generated following cleavage of the ds nucleic acid molecule by a site specific topoisomerase. Such a 5' overhanging sequence, which would contain 2 to 20 nucleotides, respectively, can be designed using a PCR method as disclosed herein to have any sequence as desired. Thus, where a cleaved first ds nucleic acid molecule is to be directionally linked to a selected second (or other) ds nucleic acid molecule according to a method of the invention, and where the selected sequence has a 5' overhanging sequence, the 5' overhang on the first ds nucleic acid molecule can be designed to be complementary to the 5' overhang on the selected second (or other) ds sequence such that the two (or more) sequences are directionally linked in a predetermined orientation due to the complementarity of the 5' overhangs. As discussed above, similar methods can be utilized with respect to 3' overhanging sequences generated upon cleavage by a type IA or type II topoisomerase.

As used herein, the term "cleavage product," when used in reference to a topoisomerase recognition site, refers to a nucleic acid molecule that has been cleaved by a topoisomerase, generally at its recognition site, and comprises a complex of the topoisomerase covalently bound, in the case of a type IB topoisomerase to the 3' phosphate group of the 3' terminal nucleotide in the topoisomerase recognition site, or, in the case of type IA or type II topoisomerase, to the 5' phosphate group of the 5' terminal nucleotide in the topoisomerase recognition site. Such a complex, which comprises a topoisomerase cleaved ds nucleic acid molecule having the topoisomerase covalently bound thereto, is referred to herein as a "topoisomerase-activated" or a "topoisomerase-charged" nucleic acid molecule. Topoisomerase-activated ds nucleic acid molecules can be used in a method of the invention, as can ds nucleic acid molecules that contain an uncleaved topoisomerase recognition site and a topoisomerase, wherein the topoisomerase can cleave the ds nucleic acid molecule at the recognition site and become covalently bound thereto.

As will be readily apparent from the present disclosure, the ends of ds nucleic acid molecules to be linked according to a method of the invention can have various characteristics. For example, in one aspect, the second end of a first precursor ds nucleic acid is a blunt end upon cleavage by the topoisomerase, and the second end of a second ds nucleic acid molecule is a blunt end. In another aspect, the second end of a first precursor ds nucleic acid molecule has a 3' thymidine extension upon cleavage by the topoisomerase, and the second end of a second ds nucleic acid molecule has a 3' adenosine overhang, or the termini can comprise 3' adenosine and 3' deoxyuridine overhangs (see U.S. Pat. Nos. 5,487,993 and 5,856,144, each of which is incorporated herein by reference). In yet another aspect, a first precursor ds nucleic acid molecule has a second 5' target sequence at the second end, and the second end of a second ds nucleic acid molecule has a 5' nucleotide sequence complementary to at least a portion of the second 5' target sequence. The first precursor ds nucleic acid molecule can be a vector, including a cloning vector and an expression vector, and, where generally present in a circular form, can be linearized due to the action of the topoisomerase, or can be linearized by including, for example, one or two restriction endonucleases that linearize the vector such that, upon contact with the topoisomerase, the first and second ds nucleic acid molecules can be directionally linked according to a method of the invention.

As used herein, the term "at or near," when used in reference to the proximity of a topoisomerase recognition site to the 3' (type IB) or 5' (type IA or type II) terminus of a nucleic acid molecule, means that the site is within about 1 to 100 nucleotides from the 3' terminus or 5' terminus, respectively, generally within about 1 to 20 nucleotides from the terminus, and particularly within about 2 to 12 nucleotides from the respective terminus. An advantage of positioning the topoisomerase recognition site within about 10 to 15 nucleotides of a terminus is that, upon cleavage by the topoisomerase, the portion of the sequence downstream of the cleavage site can spontaneously dissociate from the remaining nucleic acid molecule, which contains the covalently bound topoisomerase (referred to generally as "suicide cleavage"; see, for example, Shuman, supra, 1991; Andersen et al., supra, 1991). Where a topoisomerase recognition site is greater than about 12 to 15 nucleotides from the terminus, the nucleic acid molecule upstream or downstream of the cleavage site can be induced to dissociate from the remainder of the sequence by modifying the reaction conditions, for example, by providing an incubation step at a temperature above the melting temperature of the portion of the duplex including the topoisomerase cleavage site.

A method of the invention using a first precursor ds nucleic acid molecule having a 5' target sequence and a topoisomerase on a first end and a second end, can be performed to directionally or non-directionally link a first precursor ds nucleic acid molecule to a second ds nucleic acid molecule. The method typically is used to directionally link the first precursor ds nucleic acid molecule and the second ds nucleic acid molecule, and also can be used to non-directionally link the first precursor ds nucleic acid molecule and the second ds nucleic acid molecule. Non-directional linking can be performed, for example, 1) where a second nucleotide sequence is present at or near the 5' terminus of the second end of the first precursor ds nucleic acid molecule, that is capable of hybridizing to the 5' complementary nucleotide sequence of the second ds nucleic acid molecule; and 2) where a nucleotide sequence is present at or near the 5' terminus of both the first end and the second end of the second ds nucleic acid molecule that is capable of hybridizing to the 5' target sequences at or near the first end of the first precursor ds nucleic acid molecule. In these embodiments, the second end of the first precursor ds nucleic acid molecule and the second end of the second ds nucleic acid molecule can be either blunt, or include an overhang.

A method for generating a directionally or non-directionally linked recombinant nucleic acid molecule also can be performed by contacting a topoisomerase-charged first ds nucleic acid molecule, which has, at a first end, a first 5' overhang and a first topoisomerase covalently bound to the 3' terminus, and a second ds nucleic acid molecule, which has a first blunt end and a second end, wherein the first blunt end includes a 5' nucleotide sequence complementary to the first 5' overhang. The method is performed under conditions such that the 5' nucleotide sequence of the first blunt end can selectively hybridize to the first 5' overhang, whereby the first topoisomerase can covalently link the 3' terminus of the first end of the first ds nucleic acid molecule with the 5' terminus of the first end of the second ds nucleic acid molecule.

Such a method can further include contacting the topoisomerase-charged first ds nucleic acid molecule and the second ds nucleic acid molecule with a third ds nucleic acid molecule, wherein a first end of the third nucleic ds acid molecule has a 5' overhang and a second topoisomerase covalently bound at the 3' terminus, and wherein the second ds nucleic acid molecule has a second blunt end, which includes a 5' nucleotide sequence complementary to the 5' overhang of the third nucleic acid molecule. The contacting can be performed, for example, under conditions such that the 5' nucleotide sequence of the second blunt end of the second ds nucleic acid can selectively hybridize to the 5' overhang of the first end of the third ds nucleic acid molecule, whereby the second topoisomerase can covalently link the 3' terminus of the first end of the third ds nucleic acid molecule with the 5' terminus of the second blunt end of the second ds nucleic acid molecule. The first and second topoisomerases can be the same or different and, if desired, the first or third ds nucleic acid molecules, instead of being topoisomerase-charged, can contain a topoisomerase recognition site, wherein the method can further include contacting the reactants with a topoisomerase. A method of the invention can be performed such that the first ds nucleic acid molecule is directionally linked to the second ds nucleic acid molecule and, thereafter, the third ds nucleic acid molecule is directionally or non-directionally linked to the second ds nucleic acid molecule, or all of the reactants can be included together at the same time.

A method of the invention provides a means to render an open reading from a cDNA or an isolated genomic DNA sequence expressible by operatively linking one or more expression control elements to the putative coding sequence. Examples of expression control elements useful in the present invention are disclosed herein and include transcriptional expression control elements, translational expression control elements, elements that facilitate the transport or localization of a nucleic acid molecule or polypeptide in (or out of) a cell, elements that confer a detectable phenotype, and the like. Transcriptional expression control elements include, for example, promoters such as those from cytomegalovirus, Moloney leukemia virus, and herpes virus, as well as those from the genes encoding metallothionein, skeletal actin, phosphoenolpyruvate carboxylase, phosphoglycerate, dihydrofolate reductase, and thymidine kinase, as well as promoters from viral long terminal repeats (LTRs) such as Rous sarcoma virus LTR; enhancers, which can be constitutively active such as an immunoglobulin enhancer, or inducible such as SV40 enhancer; and the like. For example, a metallothionein promoter is a constitutively active promoter that also can be induced to a higher level of expression upon exposure to a metal ion such as copper, nickel or cadmium ion. In comparison, a tetracycline (tet) inducible promoter is an example of a promoter that is induced upon exposure to tetracycline, or a tetracycline analog, but otherwise is inactive.

A transcriptional expression control element also can be a tissue specific expression control element, for example, a muscle cell specific expression control element, such that expression of an encoded product is restricted to the muscle cells in an individual, or to muscle cells in a mixed population of cells in culture, for example, an organ culture. Muscle cell specific expression control elements including, for example, the muscle creatine kinase promoter (Sternberg et al., *Mol. Cell. Biol.* 8:2896-2909, 1988, which is incorporated herein by reference) and the myosin light chain enhancer/promoter (Donoghue et al., *Proc. Natl. Acad. Sci., USA* 88:5847-5851, 1991, which is incorporated herein by reference) are well known in the art. Other tissue specific promoters, as well as expression control elements only expressed during particular developmental stages of a cell or organism are well known in the art.

Expression control or other elements useful in generating a construct according to a method of the invention can be obtained in various ways. In particular, many of the elements are included in commercially available vectors and can be isolated therefrom and can be modified to contain a topoisomerase recognition site at one or both ends, for example, using a PCR method as disclosed herein. In addition, the sequences of or encoding the elements useful herein generally are well known and disclosed in publications. In many cases, the elements, for example, transcriptional and translational expression control elements, as well as cell compartmentalization domains, are relatively short sequences and, therefore, are amenable to chemical synthesis of the element or a nucleotide sequence encoding the element. Thus, in one embodiment, an element comprising a composition of the invention, useful in generating a recombinant nucleic acid molecule according to a method of the invention, or included within a kit of the invention, can be chemically synthesized and, if desired, can be synthesized to contain a topoisomerase recognition site at one or both ends of the element and, further, to contain an overhanging sequence following cleavage by a site specific topoisomerase.

Where ds nucleic acid molecules are to be directionally linked according to a method of the invention, the nucleic acid molecules generally are operatively linked such that the recombinant nucleic acid molecule that is generated has a desired structure, performs a desired function, encodes a desired expression product, or the like. As used herein, the term "operatively linked" means that two or more nucleic acid molecules are positioned with respect to each other such that they act as a unit to effect a function attributable to one or both sequences or a combination thereof. For example, a nucleic acid molecule containing an open reading frame can be operatively linked to a promoter such that the promoter confers its regulatory effect on the open reading frame similarly to the way in which it would effect expression of an open reading frame that it normally is associated with in a genome in a cell. Similarly, two or more nucleic acid molecules comprising open reading frames can be operatively linked in frame such that, upon transcription and translation, a chimeric fusion polypeptide is produced.

A first ds nucleic acid molecule comprising an open reading frame can be amplified using any amplification method, for example, by PCR using a primer pair, to generate an amplified first ds nucleic acid molecule having a 5' nucleotide sequence complementary to a 5' overhang of a topoisomerase-charged ds nucleic acid molecule of the present invention. Where both ends of the amplified first ds nucleic acid molecule are complements of two overhangs on the topoisomerase-charged ds nucleic acid molecule, the 5' overhangs are different from each other. The amplified first ds nucleic acid molecule then can be contacted with the topoisomerase-charged ds nucleic acid molecule comprising a desired expression control element such as a promoter such that the second nucleic acid molecule is operatively linked to the 5' end of the coding sequence according to a method of the invention.

Various combinations of components can be used in a method of the invention. For example, the method can be performed by contacting a topoisomerase-activated first ds nucleic acid molecule; a second ds nucleic acid molecule having a first end and a second end, wherein at the first end or second end or both, the second nucleic acid molecule has a hydroxyl group at the 5' terminus of the same end; and a 5' overhang. Where the 5' terminus of one or both ends to be linked has a 5' phosphate group, a phosphatase also can be contacted with the components of the reaction mixture. Upon contacting, the phosphatase, if necessary, can generate a 5' hydroxyl group at the same end, and the second ds nucleic acid molecule then can be directionally linked to the topoisomerase-activated first ds nucleic acid molecule. The skilled artisan will recognize other combinations of components useful for performing a method of the invention.

As used herein, reference to contacting a first nucleic acid molecule and a second nucleic acid molecule "under conditions such that all components are in contact" means that the reaction conditions are appropriate for a topoisomerase-cleaved end of a first ds nucleic acid molecule to come into sufficient proximity such that a topoisomerase can effect its enzymatic activity and covalently link the 3' terminus of the first ds nucleic acid molecule to a 5' hydroxyl group at the terminus of a second nucleic acid molecule. Examples of such conditions include, for example, the reaction temperature, ionic strength, and pH. Additionally, such conditions can be determined empirically or using formulas that predict conditions for specific hybridization of nucleic acid molecules, as is well known in the art (see, for example, (Sambrook et al., *Molecular Cloning: A laboratory manual* (Cold Spring Harbor Laboratory Press 1989); Ausubel et al., *Current Protocols in Molecular Biology*, John Wiley and Sons, Baltimore, Md. (1987, and supplements through 1995), each of which is incorporated herein by reference).

As disclosed herein, a PCR method using primers designed to incorporate complementary nucleotide sequences at one or both ends of an amplified ds nucleic acid molecule provides an example of a convenient means for producing ds nucleic acid molecules useful in a method of the invention. At least one of the primers of a primer pair is designed such that it comprises, in a 5' to 3' orientation, a nucleotide sequence complementary to a first overhang on the topoisomerase-charged ds nucleic acid molecule of the present invention. The second primer of the PCR primer pair can be complementary to a desired sequence of the nucleic acid molecule to be amplified, and can comprise a second complementary sequence.

A primer can contain or encode any other sequence of interest, including, for example, a site specific integration recognition site such as an att site, a lox site, or the like, or, as discussed above, can simply be used to introduce a topoisomerase recognition site into a ds nucleic acid molecule comprising such a sequence of interest. A recombinant nucleic acid molecule generated according to a method of the invention and containing a site specific integration recognition site such as an att site or lox site can be integrated specifically into a desired locus such as into a vector, a gene locus, or the like, that contains the required integration site, for example, an att site or lox site, respectively, and upon contact with the appropriate enzymes required for the site specific event, for example, lambda Int and IHF proteins or Cre recombinase, respectively. The incorporation, for example, of attB or attP sequences into a directionally or non-directionally linked recombinant nucleic acid molecule according to a method of the invention allows for the convenient manipulation of the nucleic acid molecule using the GATEWAY™ Cloning System (Invitrogen Corp., La Jolla Calif.). A first ds nucleic acid molecule used in a method of the invention can be a linearized vector containing two site specific integration sites, for example, an "entry vector" (GATEWAY™ Cloning System), and a method of the invention can be used to insert a second (or other) ds nucleic acid molecule between the site specific integration sites.

A ds nucleic acid molecule to be used in a method or kit of the invention can be amplified using any amplification reaction, for example, using the polymerase chain reaction (PCR), to contain a complementary nucleotide sequence at a 5' end. Although exemplified by PCR, other amplification methods also can be used to amplify a nucleic acid molecule such that the amplified nucleic acid molecule has a complementary sequence at the 5' terminus of one of its ends. The complementary nucleotide sequence is complementary to the 5' overhang on the topoisomerase-charged ds nucleic acid to which the amplified nucleic acid will be ligated. This complementarity facilitates the association of the nucleic acid molecules in a predetermined orientation, whereupon they can be linked by topoisomerase according to a method of the invention.

Amplification primers can be designed to impart particular characteristics to a desired ds nucleic acid molecule, for example, a ds nucleic acid molecule that encodes a transcriptional or translational expression control element or a coding sequence of interest such as an epitope tag or cell compartmentalization domain. In this aspect, the amplification primers are designed such that, upon amplification, the ds nucleic acid molecule contains a 5' complementary sequence at one or both ends, as desired.

Amplification primers also can be used to amplify a directionally linked recombinant nucleic acid molecule generated according to a method of the invention. For example, a method of the invention can generate from three ds nucleic acid molecules, including a nucleic acid molecule comprising a promoter, a nucleic acid molecule comprising a coding sequence, and a nucleic acid molecule comprising a polyadenylation signal, an expressible recombinant nucleic acid molecule. The generation of the nucleic acid molecule is facilitated by the incorporation of complementary 5' (or 3') sequences at the ends of the ds nucleotides sequences to be joined, wherein preferably one of the complementary sequences is an overhang sequence.

As such, by designing a PCR primer pair containing a first primer that is specific for an overhang of the nucleic acid molecule comprising the promoter that is upstream from the promoter, and a second primer that is specific for an overhang of the nucleic acid molecule comprising the polyadenylation signal that is down stream of the signal, only a full length functional recombinant nucleic molecule containing the promoter, coding sequence and polyadenylation signal in the correct (predetermined) orientation will be amplified. In particular, partial reaction products, for example, containing only a promoter linked to the coding sequence, and reaction products containing nicks are not amplified. Thus, PCR can be used to specifically design a ds nucleic acid molecule such that it is useful in a method of the invention, and to selectively amplify only those reaction products having the desired components and characteristics.

A method of the invention can be performed such that a second ds nucleic acid molecule to be directionally ligated to a first ds nucleic acid molecule, is one of a plurality of second ds nucleic acid molecules. As used herein, the term "plurality," when used in reference a first or at least a second nucleic acid molecule, means that the nucleic acid molecules are related but different. For purposes of the present invention, the nucleic acid molecules of a plurality are "related" in that each nucleic acid molecule in the plurality contains, for example, a 5' nucleotide sequence that is complementary to a 5' overhang sequence present on a topoisomerase-charged ds nucleic acid molecule to which the second ds nucleic acid molecules are to be directionally linked. Furthermore, the nucleic acid molecules of a plurality are "different" in that they can comprise, for example, a cDNA library, a combinatorial library of nucleic acid molecules, a variegated population of nucleic acid molecules, or the like. Methods of making cDNA libraries, combinatorial libraries, libraries comprising variegated populations of nucleic acid molecules, and the like are well known in the art (see, for example, U.S. Pat. No. 5,837,500; U.S. Pat. No. 5,622,699; U.S. Pat. No. 5,206,347; Scott and Smith, *Science* 249:386-390, 1992; Markland et al., *Gene* 109:13-19, 1991; O'Connell et al., *Proc. Natl. Acad. Sci., USA* 93:5883-5887, 1996; Tuerk and Gold, *Science* 249: 505-510, 1990; Gold et al., *Ann. Rev. Biochem.* 64:763-797, 1995; each of which is incorporated herein by reference).

Where a second ds nucleic acid molecule is one of a population of ds nucleic acid molecules, a method of the invention can further utilize a population of first ds nucleic acid molecules, each of which contains a different and randomly generated nucleotide sequence at or near a 3' and/or 5' terminus of a first and/or second end, for example, randomly generated 3' or 5' overhangs at or near a first end. Such a population of randomly generated nucleotide sequences near an end will include complementary sequences to nucleotide sequences at or near the ends of many or all of the second ds nucleic acid molecules of the plurality. Thus, the method can be used to generate linked recombinant nucleic acid molecules, including many or all of the nucleic acid molecules in the plurality of second ds nucleic acid molecules.

The methods of the invention have broad application to the field of molecular biology. As discussed in greater detail below, the methods of the invention can be used, for example, to label DNA or RNA probes, to generate sense or antisense RNA, to prepare bait or prey constructs for performing a two hybrid assay, to prepare linear expression elements, to prepare constructs useful for coupled in vitro transcription/translation assays, and to perform directional cloning.

A directionally or non-directionally linked recombinant nucleic acid molecule generated according to this aspect of the invention can be linear, but preferably is circular, particularly a vector, as described above. The circular recombinant nucleic acid molecule can be generated such that it has the characteristics of a vector, and contains, for example, expression control elements required for replication in a prokaryotic host cell, a eukaryotic host cell, or both, and can contain a nucleotide sequence encoding a polypeptide that confers antibiotic resistance or the like.

A method of the invention can further include introducing a directionally or non-directionally linked recombinant nucleic acid molecule into a cell, which can be a prokaryotic cell such as a bacterium or a eukaryotic cell such as a mammalian cell. Accordingly, the present invention also provides a cell produced by a method of the invention, as well as a non-human transgenic organism produced from such a cell. An advantage of such a method is that the generated recombinant nucleic acid molecule, which is circularized according to a method of the invention, can be transformed or transfected into an appropriate host cell, wherein the construct is amplified. Thus, an in vivo method using a host cell can be used for obtaining a large amount of a circularized product generated according to a method of the invention.

It should be recognized that a method of the invention is characterized, in part, in that a linked recombinant nucleic acid molecule generated thereby either contains a nick in one strand, because a topoisomerase is attached to only one 3'terminus of the ends to be linked, or comprises one strand that is derived completely from only one of two nucleic acid molecule linked according to the method. Where the recombinant nucleic acid molecule contains a nick, the nick can be converted to a phosphodiester bond, if desired, for example, by contacting the nicked recombinant nucleic acid molecule with a DNA ligase, by introducing the nicked recombinant nucleic acid molecule into a cell such as a bacterium that can repair the nick, or by any other method as desired. Thus, in one embodiment, a method of the invention includes a strand invasion event and a ligation.

Where a recombinant nucleic acid molecule generated according to a method of the invention does not comprise one strand that is derived completely from only one of the starting nucleic acid molecules, the method can further include a cleavage step, wherein the displaced nucleotide sequence is cleaved from the product. Such a cleaving step can be performed using any method known to cleave or degrade a single stranded nucleotide sequence, including, for example, contacting a recombinant nucleic acid molecule comprising the displaced strand with an enzyme having, 5' to 3' or 3' to 5' single stranded nucleic acid exonuclease activity (depending on the orientation of the displaced strand). Such a method conveniently can be performed in vitro. Alternatively, the recombinant ds nucleic acid molecule can be introduced into a cell, for example an *E. coli* cell, wherein the displaced nucleotide sequence is cleaved.

A method of the invention can be used to generate a directionally linked recombinant nucleic acid molecule encoding a chimeric fusion polypeptide. For generating such a recombinant nucleic acid molecule, a first and second (or other) ds nucleic acid molecule each can encode all or a portion of an open reading frame, and the first and second (or other) ds nucleic acid molecules, which have first and/or second ends as disclosed herein, are directionally linked. The chimeric polypeptide can comprise a fusion polypeptide, in which the two (or more) encoded peptides (or polypeptides) are translated into a single product, i.e., the peptides are covalently linked through a peptide bond.

For example, a first ds nucleic acid molecule can encode a cell compartmentalization domain, such as a plasma membrane localization domain, a nuclear localization signal, a mitochondrial membrane localization signal, an endoplasmic reticulum localization signal, or the like, or a protein transduction domain such as the human immunodeficiency virus TAT protein transduction domain, which can facilitate translocation of a peptide linked thereto into a cell (see Schwarze et al., *Science* 285:1569-1572, 1999; Derossi et al., J. Biol. Chem. 271:18188, 1996; Hancock et al., *EMBO J.* 10:4033-4039, 1991; Buss et al., *Mol. Cell. Biol.* 8:3960-3963, 1988; U.S. Pat. No. 5,776,689 each of which is incorporated herein by reference). Such a domain can be useful to target a fusion polypeptide comprising the domain and a polypeptide encoded by a second ds nucleic acid molecule, to which it is directionally linked according to a method of the invention, to a particular compartment in the cell, or for secretion from or entry into a cell. As such, the invention provides a means to generate directionally linked recombinant nucleic acid molecules that encode a chimeric polypeptide.

A fusion polypeptide expressed from a directionally linked recombinant nucleic acid molecule generated according to a method of the invention also can comprise a peptide having the characteristic of a detectable label or a tag such that the expressed fusion polypeptide can be detected, isolated, or the like. For example, a first, second or other ds nucleic acid molecule containing a topoisomerase recognition site, or cleavage product thereof, as disclosed herein, can encode an enzyme such as alkaline phosphatase, $\beta$-galactosidase, chloramphenicol acetyltransferase, luciferase, or other enzyme; or can encode a peptide tag such as a polyhistidine sequence (e.g., hexahistidine), a V5 epitope, a c-myc epitope; a hemagglutinin A epitope, a FLAG epitope, or the like. Expression of a fusion polypeptide comprising a detectable label can be detected using the appropriate reagent, for example, by detecting light emission upon addition of luciferin to a fusion polypeptide comprising luciferase, or by detecting binding of nickel ion to a fusion polypeptide comprising a polyhistidine tag.

A polyhistidine tag can comprise from about two to about ten contiguous histidine residues (e.g., two, three, four, five, six, seven, eight, nine, or ten contiguous histidine residues). The tag can also be a peptide tag which binds nickel ions, as well as other metal ions (e.g., copper ion), and can be used for metal chelate affinity chromatography. Examples of such tags include peptides having the formula: $R_1$-(His-X)$_n$—$R_2$, wherein (His-X)$_n$ represents a metal chelating peptide and n is a number between two through ten (e.g., two, three, four, five, six, seven, eight, nine, or ten), and X is an amino acid selected from the group consisting of alanine, arginine, aspartic acid, asparagine, cysteine, glutamic acid, glutamine, glycine, histidine, iso-leucine, leucine, lysine, methionine, phenylalanine, proline, serine, threonine, tryptophan, tyrosine and valine. Further, R2 may be a polypeptide which is covalently linked to the metal chelating peptide and R1 may be either a hydrogen or one or more (e.g., one, two, three, four, five, six, seven, eight, nine, ten, twenty, thirty, fifty, sixty, etc.) amino acid residues. In addition, R1 may be a polypeptide which is covalently linked to the metal chelating peptide and R2 may be either a hydrogen or one or more (e.g., one, two, three, four, five, six, seven, eight, nine, ten, twenty, thirty, fifty, sixty, etc.) amino acid residues. Tags of this nature are described in U.S. Pat. No. 5,594,115, the entire disclosure of which is incorporated herein by reference.

Similarly, isolation of a fusion polypeptide comprising a tag can be performed, for example, by passing a fusion polypeptide comprising a myc epitope over a column having an anti-c-myc epitope antibody bound thereto, then eluting the bound fusion polypeptide, or by passing a fusion polypeptide comprising a polyhistidine tag over a nickel ion or cobalt ion affinity column and eluting the bound fusion polypeptide. Methods for detecting or isolating such fusion polypeptides will be well known to those in the art, based on the selected detectable label or tag (see, for example, Hopp et al., Bio-Technology 6:1204, 1988; U.S. Pat. No. 5,011,912; each of which is incorporated herein by reference).

In one embodiment, the directionally linked recombinant nucleic acid molecules encode chimeric polypeptides useful for performing a two hybrid assay. In such a method, the first ds nucleic acid molecule encodes a polypeptide, or a relevant domain thereof, that is suspected of having or being examined for the ability to interact specifically with one or more (e.g., 1, 2, 3, 4, 5, 6, 7, 8, 9, 10, etc.) other polypeptides. The second ds nucleic acid molecule, to which the first ds nucleic acid molecule is to be directionally linked according to a method of the invention, can encode a transcription activation domain or a DNA binding domain. For example, a first ds nucleic acid molecules to be directionally linked is modified, for example, to contain a 5' overhang on a first end and a topoisomerase recognition site, or cleavage product thereof, at or near the first end. A second ds nucleic acid molecules to be linked contains, or is modified to contain, a 5' sequence complementary to the 5' overhang at the first end of the first ds nucleic acid molecule. Upon contact of the first and second ds nucleic acid molecules with a topoisomerase, the directionally linked nucleic acid molecule encodes a first hybrid useful for performing a two hybrid assay (see, for example, Fields and Song, Nature 340:245-246, 1989; U.S. Pat. No. 5,283,173; Fearon et al., Proc. Natl. Acad. Sci., USA 89:7958-7962, 1992; Chien et al., Proc. Natl. Acad. Sci. USA 88:9578-9582, 1991; Young, Biol. Reprod. 58:302-311(1998), each of which is incorporated herein by reference). Similar methods are used to generate the second hybrid protein, which can comprise a plurality of polypeptides to be tested for the ability to interact with the polypeptide, or domain thereof, of the first hybrid protein. Such methods similarly can be used to construct directionally linked nucleic acid molecules encoding fusion protein useful for a modified form of a two hybrid assay such as the reverse two hybrid assay (Leanna and Hannink, Nucl. Acids Res. 24:3341-3347, 1996, which is incorporated herein by reference), the repressed transactivator system (U.S. Pat. No. 5,885,779, which is incorporated herein by reference), the protein recruitment system (U.S. Pat. No. 5,776,689, which is incorporated herein by reference), and the like.

As disclosed herein, a second ds nucleic acid molecule can be one of a plurality of nucleic acid molecules, for example, a cDNA library, a combinatorial library of nucleic acid molecules, or a population of variegated nucleic acid molecules. As such, the methods of the invention are particularly useful for generating recombinant polynucleotides encoding chimeric polypeptides for performing a high throughput two hybrid assay for identifying protein-protein interactions that occur among populations of polypeptides (see U.S. Pat. No. 6,057,101 and U.S. Pat. No. 6,083,693, each of which is incorporated herein by reference). In such a method, each of the hybrid proteins of the two hybrid assay is generated using a different one of two populations (pluralities) of nucleic acid molecules encoding polypeptides, each plurality having a complexity of from a few related but different nucleic acid molecules to as high as tens of thousands of such molecules. By performing a method of the invention, for example, using a PCR primer pair to amplify each nucleic acid molecule in a plurality, directionally linked recombinant polynucleotides encoding a population of chimeric bait polypeptides and a population of chimeric prey polypeptides readily can be generated. Such populations are generated by contacting the amplified pluralities of nucleic acid molecules, each of which comprises an appropriate end, with a topoisomerase and a nucleic acid molecule which contains a topoisomerase recognition site at or near its ends and encodes a transcription activation domain or a DNA binding domain.

A first ds nucleic acid molecule useful in a method of the invention also can encode a ribonucleic acid (RNA) molecule, which can function, for example, as a riboprobe, an antisense nucleic acid molecule, a ribozyme, or a triplexing nucleic acid molecule, or can be used in an in vitro translation reaction, and the second ds nucleic acid molecule can encode an expression control element useful for expressing an RNA from the first nucleic acid molecule. For example, where it is desired to produce a large amount of RNA, a second ds nucleic acid molecule component for performing a method of the invention can comprise an RNA polymerase promoter such as a T7, T3 or SP6 RNA polymerase promoter. Where the RNA molecule is to be expressed in a cell, for example, an antisense molecule to be expressed in a mammalian cell, the second (or other) ds nucleic acid molecule can include a promoter that is active in a mammalian cell, particularly a tissue specific promoter, which is active only in a target cell. Furthermore, where the RNA molecule is to be translated, for example, in a coupled in vitro transcription/translation reaction, the first nucleic acid molecule or second (or other) nucleic acid molecule can contain appropriate translational expression control elements.

A directionally or non-directionally linked recombinant nucleic acid molecule generated according to a method of the invention can be used for various purposes for which recombinant vectors containing a directionally or non-directionally inserted nucleic acid molecule are generally used. Thus, the directionally or non-directionally linked nucleic acid molecule can be used, for example, for expressing a polypeptide in a cell, for diagnosing or treating a pathologic condition, or the like. For administration to a living subject, the directionally or non-directionally linked recombinant nucleic acid molecule generally is formulated in a pharmaceutical composition suitable for administration to the subject. Thus, the invention provides pharmaceutical compositions containing a directionally or non-directionally linked recombinant nucleic acid molecule generated according to a method of the invention and expression products of this nucleic acid molecule. As such, the nucleic acid molecule is useful as a medicament for treating a subject suffering from a pathological condition.

Pharmaceutically acceptable carriers are well known in the art and include, for example, aqueous solutions such as water or physiologically buffered saline or other solvents or vehicles such as glycols, glycerol, oils such as olive oil or injectable organic esters. A pharmaceutically acceptable carrier can contain physiologically acceptable compounds that act, for example, to stabilize or to increase the absorption of the conjugate. Such physiologically acceptable compounds include, for example, carbohydrates, such as glucose, sucrose or dextrans, antioxidants, such as ascorbic acid or glutathione, chelating agents, low molecular weight proteins or other stabilizers or excipients. One skilled in the art would know that the choice of a pharmaceutically acceptable carrier, including a physiologically acceptable compound, depends, for example, on the route of administration of the composition, which can be, for example, orally or parenterally such as intravenously, and by injection, intubation, or other such method known in the art. The pharmaceutical composition also can contain a second reagent such as a diagnostic reagent, nutritional substance, toxin, or therapeutic agent, for example, a cancer chemotherapeutic agent.

The directionally linked recombinant nucleic acid molecule can be incorporated within an encapsulating material such as into an oil-in-water emulsion, a microemulsion, micelle, mixed micelle, liposome, microsphere or other polymer matrix (see, for example, Gregoriadis, Liposome Technology, Vol. 1 (CRC Press, Boca Raton, Fla. 1984); Fraley, et al., Trends Biochem. Sci., 6:77 (1981), each of which is incorporated herein by reference). Liposomes, for example, which consist of phospholipids or other lipids, are nontoxic, physiologically acceptable and metabolizable carriers that are relatively simple to make and administer. "Stealth" liposomes (see, for example, U.S. Pat. Nos. 5,882,679; 5,395, 619; and 5,225,212, each of which is incorporated herein by reference) are an example of such encapsulating materials particularly useful for preparing a pharmaceutical composition, and other "masked" liposomes similarly can be used, such liposomes extending the time that a nucleic acid molecule remains in the circulation. Cationic liposomes, for example, also can be modified with specific receptors or ligands (Morishita et al., J. Clin. Invest., 91:2580-2585 (1993), which is incorporated herein by reference). The nucleic acid molecule also can be introduced into a cell by complexing it with an adenovirus-polylysine complex (see, for example, Michael et al., J. Biol. Chem. 268:6866-6869 (1993), which is incorporated herein by reference). Such compositions can be particularly useful for introducing a nucleic acid molecule into a cell in vivo or in vitro, including ex vivo, wherein the cell containing the nucleic acid molecule is administered back to the subject (see U.S. Pat. No. 5,399, 346, which is incorporated herein by reference). A nucleic acid molecule generated according to a method of the invention also can be introduced into a cell using a biolistic method (see, for example, Sykes and Johnston, supra, 1999).

As disclosed herein, a directionally linked nucleic acid molecule generated according to a method of the invention contains a nick, which can be resolved, for example, by contacting the nicked recombinant nucleic acid molecule with a ligase. Such a directionally linked recombinant nucleic acid molecule that is covalently linked in both strands can be used as a template for an amplification reaction such as PCR. As such, a large amount of the construct can be generated. Furthermore, an amplification reaction can provide an in vitro selection method for obtaining only a desired product, without obtaining partial reaction products. For example, a method of the invention can be used to generate a directionally linked recombinant nucleic acid molecule comprising, operatively linked in a 5' to 3' orientation, a first ds nucleic acid molecule comprising a promoter, a second ds nucleic acid molecule comprising a coding region, and a third ds nucleic acid molecule comprising a polyadenylation signal, wherein the nicks in the generated recombinant nucleic acid molecule are ligated.

By selecting a PCR primer pair including a first primer complementary to a nucleotide sequence upstream of the promoter sequence, and a second primer complementary to a nucleotide sequence downstream of the polyadenylation signal, a functional amplification product comprising the promoter, coding region and polyadenylation signal can be generated. In contrast, partial reaction products that lack either the first ds nucleic acid molecule or third ds nucleotide are not amplified because either the first or second primer, respectively, will not hybridize to the partial product. In addition, a construct lacking the second ds nucleic acid molecule would not be generated due to the lack of complementarity of the 5' overhanging sequences of the first and third ds nucleic acid molecules. As such, the invention provides, in part, a means to obtain a desired functional, directionally linked recombinant nucleic acid molecule.

The use of an amplification reaction such as PCR in such a manner further provides a means to screen a large number of nucleic acid molecules generated according to a method of the invention in order to identify constructs of interest. Since methods for utilizing PCR in automated high throughput analyses are routine and well known, it will be recognized that the methods of the invention can be readily adapted to use in a high throughput system. Using such a system, a large number of constructs can be screened in parallel, and partial or incomplete reaction products can be identified and disposed of, thereby preventing a waste of time and expense that would otherwise be required to characterize the constructs or examine the functionality of the constructs in further experiments.

Recombinant nucleic acid molecules generated by a method of the invention wherein the first ds nucleic acid molecule contains a first topoisomerase but not a second topoisomerase or topoisomerase binding site, are generally linear, whereas, in other aspects, the methods of the invention can generate circular recombinant nucleic acid molecules. However, a directionally linked recombinant nucleic acid molecule that is generated as a linear molecule can be circularized, for example, where it is to be used as a vector. In addition, a linear directionally linked recombinant nucleic acid molecule generated by a method of the invention can be cloned into a vector, which can be a plasmid vector or a viral vector such as a bacteriophage, baculovirus, retrovirus, lentivirus, adenovirus, Vaccinia virus, semliki forest virus and adeno-associated virus vector, all of which are well known and can be purchased from commercial sources (Invitrogen Corp., La Jolla Calif.; Promega, Madison Wis.; Stratagene, La Jolla Calif.; GIBCO/BRL, Gaithersburg Md.).

The methods of the invention also can be used to detectably label a nucleic acid molecule with a chemical or small organic or inorganic moiety such that the nucleic acid molecule is useful as a probe. For example, a first ds nucleic acid molecule, which has a topoisomerase recognition site, or cleavage product thereof, at a 3' terminus, can have bound thereto a detectable moiety such as a biotin, which can be detected using avidin or streptavidin, a fluorescent compound (e.g., Cy3, Cy5, Fam, fluorescein, or rhodamine), a radionuclide (e.g., sulfur-35, technicium-99, phosphorus-32, or tritium), a paramagnetic spin label (e.g., carbon-13), a chemiluminescent compound, an epitope, for example a peptide epitope, which can be detected using an antibody that recognizes the epitope, or the like, such that, upon generating a directionally linked double stranded recombinant nucleic acid molecule according to a method of the invention, the generated nucleic acid molecule will be labeled. Methods of detectably labeling a nucleic acid molecule with such moieties are well known in the art (see, for example, Hermanson, "Bioconjugate Techniques" (Academic Press 1996), which is incorporated herein by reference). It should be recognized that such elements as disclosed herein or otherwise known in the art, including nucleic acid molecules encoding cell compartmentalization domains, or detectable labels or tags, or comprising transcriptional or translation expression control elements can be useful components of a kit as disclosed herein.

A method of the invention, in which a first ds nucleic acid molecule with a first topoisomerase, but not a second topoisomerase or topoisomerase recognition site, is used can be particularly useful for generating an expressible recombinant nucleic acid molecule that can be inserted in a site specific manner into a target DNA sequence. The target DNA sequence can be any DNA sequence, particularly a genomic DNA sequence, and preferably a gene for which some or all of the nucleotide sequence is known. The method can be performed utilizing a first ds nucleic acid molecule, which has a first end and a second end and encodes a polypeptide, for example, a selectable marker, wherein the first ds nucleic acid molecule comprises a complementary sequence at both ends; and directionally linking the first ds nucleic acid molecule to first and second PCR amplification products, which are generated from sequences upstream and downstream of the site at which the construct is to be inserted, wherein each amplification products each contain a topoisomerase recognition site and a 5' target sequence selected based on the factors set forth in the present disclosure. For example, the first and second amplification products have different 5' target sequences such that, upon cleavage by a topoisomerase, each can be linked to a predetermined end of the first ds nucleic acid molecule.

The first and second amplification products are generated using two sets of PCR primer pairs. The two sets of PCR primer pairs are selected such that, in the presence of an appropriate polymerase such as Taq polymerase and a template comprising the sequences to be amplified, the primers amplify portions of a target DNA sequence that are upstream of and adjacent to, and downstream of and adjacent to, the site for insertion of the selectable marker. In addition, the sets of PCR primer pairs are designed such that the amplification products contain a topoisomerase recognition site and, following cleavage by the site specific topoisomerase, a 5' overhanging sequence at the end to be directionally linked to the selectable marker. As such, the first PCR primer pair includes 1) a first primer, which comprises, in an orientation from 5' to 3', a nucleotide sequence complementary to a 5' complementary sequence of the end of the selectable marker to which the amplification product is to be directionally linked, a nucleotide sequence complementary to a topoisomerase recognition site, and a nucleotide sequence complementary to a 3' sequence of a target DNA sequence upstream of the insertion site; and 2) a second primer, which comprises a nucleotide sequence of the target genomic DNA upstream of the 3' sequence to which the first primer is complementary, i.e., downstream of the insertion site. The second PCR primer pair includes 1) a first primer, which comprises, from 5' to 3', a nucleotide sequence complementary to the 5' complementary sequence of the end of the selectable marker to which it is to be directionally linked, a nucleotide sequence complementary to a topoisomerase recognition site, and a nucleotide sequence of a 5' sequence of a target DNA sequence, wherein the 5' sequence of the target genomic DNA is downstream of the 3' sequence of the target DNA sequence to which the first primer of the first PCR primer pair is complementary; and the second primer of the second primer pair comprises a nucleotide sequence complementary to a 3' sequence of the target DNA sequence that is downstream of the 5' sequence of the target genomic DNA contained in the first primer. The skilled artisan will recognize that the sequences of the primer that are complementary to the target genomic DNA are selected based on the sequence of the target DNA.

Upon contact of the first ds nucleic acid molecule comprising the selectable marker, the first and second amplification products (i.e., second and third ds nucleic acid molecules), and a topoisomerase (unless the molecules are topoisomerase-charged), a directionally linked recombinant nucleic acid molecule is generated. Following ligation of the nicks, the generated recombinant nucleic acid molecule can be further amplified, if desired, using PCR primers that are specific for an upstream and downstream sequence of the target genomic DNA, thus ensuring that only functional constructs are amplified. Such a generated directionally linked recombinant nucleic acid molecule is useful for performing homologous recombination in a genome, for example, to knock-out the function of a gene in a cell, or to confer a novel phenotype on the cell containing the generated recombinant nucleic acid molecule. The method can further be used to produce a transgenic non-human organism having the generated recombinant nucleic acid molecule stably maintained in its genome.

A method of the invention involving a first ds nucleic acid having a topoisomerase or topoisomerase-recognition site, for example, at a first end but not the second end, also can be useful for covalently linking an adapter or linker sequence to one or both ends of a second ds nucleic acid molecule of interest, including to each of a plurality of second (or other) ds nucleic acid molecules. For example, where it is desired to put linkers on both ends of a first ds nucleic acid molecule, the method can be performed by contacting a topoisomerase with a first ds nucleic acid molecule, which has a 5' complementary sequence at or near each 5' terminus that is complementary to an overhang sequence on a 5' terminus of each of the second and third ds nucleic acid molecules; and a second ds nucleic acid molecule and a third ds nucleic acid molecule, each of which includes a topoisomerase recognition site at the appropriate 3' terminus and a 5' overhang sequence at or near the end containing the topoisomerase recognition site. An appropriate terminus is the terminus to which the linker is to be directionally linked to the first ds nucleic acid molecule. In performing such a method, the linker sequences comprising the second and at least third nucleic acid molecule can be the same or different.

A method of the invention involving a first ds nucleic acid molecule with a 5' target sequence and a topoisomerase on a first end, can be performed to directionally or non-directionally link a first ds nucleic acid molecule to at least a second ds nucleic acid molecule. The method typically is used to directionally link the first ds nucleic acid molecule and the second ds nucleic acid molecule. However, the method can be used to non-directionally link the first ds nucleic acid molecule and the second ds nucleic acid molecule in the following embodiments: 1) Where a second nucleotide sequence is present at or near the 5' terminus of the second end of the first ds nucleic acid molecule, that is capable of hybridizing to the 5' complementary nucleotide sequence at the second end of the second ds nucleic acid molecule; and 2) Where a nucleotide sequence is present at or near the 5' terminus of both the first end and the second end of the second ds nucleic acid molecule that is capable of hybridizing to the 5' overhang at the first end of the first ds nucleic acid molecule. In these embodiments involving non-directional linking, the second end of the first ds nucleic acid molecule and the second end of the second ds nucleic acid molecule can be either blunt, or include an overhang.

In embodiments involving a linking a third ds nucleic acid molecule to the second ds nucleic acid molecule, the methods can be used to directionally or non-directionally link the two nucleic acid molecules. The method typically is used to directionally link the second ds nucleic acid molecule and the third ds nucleic acid molecule. However, the method can be used to non-directionally link the third ds nucleic acid molecule and the second ds nucleic acid molecule in the following embodiments: 1) Where a second nucleotide sequence is present at or near the 5' terminus of the second end of the third ds nucleic acid molecule, that is capable of hybridizing to the 5' complementary nucleotide sequence at the second end of the second ds nucleic acid molecule; and 2) Where a nucleotide sequence is present at or near the 5' terminus of both the first end and the second end of the second ds nucleic acid molecule that is capable of hybridizing to the 5' overhang at the first end of the third ds nucleic acid molecule. In these embodiments involving non-directional linking, the second end of the third ds nucleic acid molecule and the second end of the second ds nucleic acid molecule can be either blunt, or include an overhang.

The present invention also provides a composition, which includes a first ds nucleic acid molecule having a first end and a second end, wherein the first end has a 5' overhang and a topoisomerase covalently bound at the 3' terminus; and a second ds nucleic acid molecule having a first blunt end and a second end, wherein the first blunt end has a first 5' nucleotide sequence, which is complementary to the first 5'-overhang, and a first 3' nucleotide sequence complementary to the first 5' nucleotide sequence. In such a composition, the first 5' nucleotide sequence of the first blunt end of the second ds nucleic acid molecule can be hybridized to the first 5' overhang of the first end of the first nucleic acid molecule, wherein the first 3' nucleotide sequence of the first blunt end of the second ds nucleic acid molecule displaced. The first ds nucleic acid molecule in such a composition can further have a second 5' overhang at the second end, and the second end of the second ds nucleic acid molecule can further include a second 5' nucleotide sequence, which is complementary to the second 5' overhang, and a second 3' nucleotide sequence complementary to the second 5' nucleotide sequence.

The present invention also provides kits, which contain one or more (e.g., 1, 2, 3, 4, 5, 6, 7, 8, 9, 10, etc.) reagents useful for directionally or non-directionally linking ds nucleic acid molecules. In one embodiment, a kit of the invention contains a ds nucleic acid molecule having a first end and a second end, wherein the first end contains a first 5' overhang and a first topoisomerase covalently bound at the 3' terminus, and the second end contains a second topoisomerase covalently bound at the 3' terminus and contains a second 5' overhang, a blunt end, a 3' uridine overhang, or a 3' thymidine overhang, wherein the first 5' overhang is different from the second 5' overhang. The topoisomerases, which can be the same or different, also can be a component of the kit. The ds nucleic acid molecule in the kit can, but need not be a vector, and can contain one or more (e.g., 1, 2, 3, 4, 5, 6, 7, 8, 9, 10, etc.) expression control elements, as well as instructions for using kit components.

A kit of the invention also can include a plurality of second ds nucleic acid molecules, wherein each ds nucleic acid molecule in the plurality has a first blunt end, and wherein the first blunt end includes a 5' nucleotide sequence complementary to the first 5' overhang of the first ds nucleic acid molecule. The second ds nucleic acid molecules in the plurality can be a plurality of transcriptional regulatory elements, translational regulatory elements, or a combination thereof, or can encode a plurality of peptides such as peptide tags, cell compartmentalization domains, and the like.

A ds nucleic acid molecule component of a kit can be, for example, a linearized vector such as a cloning vector or expression vector. If desired, such a kit can contain a plurality of ds nucleic acid molecules, each comprising a different expression control element or other element such as, but not limited to, a sequence encoding a tag or other detectable molecule or a cell compartmentalization domain. The different elements can be different types of a particular expression control element, for example, constitutive or inducible promoters or tissue specific promoters, or can be different types of elements including, for example, transcriptional and translational expression control elements, epitope tags, and the like. Such ds nucleic acid molecules may be topoisomerase-activated or can be activated with topoisomerase, and contain 5' overhanging sequences, or sequences that become 5' overhanging sequences after topoisomerase activation. In addition, the plurality of ds nucleic acid molecules can have 5' overhanging sequences that are unique to a particular expression control element, or that are common to plurality of related expression control elements, for example, to a plurality of different promoter elements. The 5' overhanging sequences of ds nucleic acid molecules can be designed such that one or more expression control elements contained on the ds nucleic acid molecule can be operatively directionally linked to provide a useful function, for example, an element comprising a Kozak sequence and an element comprising a translation start site can have complementary 5' overhangs such that the elements can be operatively directionally linked according to a method of the invention.

The invention further provides kits for linking nucleic acid molecules using methods described herein. Thus, kits of the invention may comprise one or more components for performing methods described herein. In particular embodiments, kits of the invention may comprise one or more component selected from the group consisting of instructions for use of kits components, one or more buffers, one or more nucleic acid molecules (e.g., one or more nucleic acid molecules having a 5' overhang, a 3' overhang, a 5' overhang and a 3' overhang, two 3' overhangs, two 5' overhangs, etc.), one or more topoisomerase, one or more ligase, one or more recombinase, one or more adapter linker for preparing molecules having a 5' overhang and/or a 3' overhang, and/or one or more containers in which to perform methods of the invention.

The following examples are intended to illustrate but not limit the invention.

EXAMPLE 1

In a preferred embodiment of the present invention, a topoisomerase-charged ds nucleic acid molecule is made by first obtaining a commercially available cloning vector. One such vector is pUni/V5-His version A, (Invitrogen Corp, Carlsbad, Calif.), a circular supercoiled vector that contains uniquely designed elements. These elements include a BGH polyadenylation sequence to increase mRNA stability in eukaryotic hosts, a T7 transcription termination region, an R6Kγ DNA replication origin and a kanamycin resistance gene and promoter for antibiotic resistance selection. Additionally, pUni/V5-His version A contains a multiple cloning site, which is a synthetic DNA sequence encoding a series of restriction endonuclease recognition sites. These sites are engineered for cloning of DNA into a vector at a specific position. Also within the vector's multiple cloning site is a loxP site inserted 5' to the endonuclease recognition sites thereby facilitating Cre recombinase-mediated fusion into a variety of other expression vectors, (Echo™ Cloning System, Invitrogen Corp., Carlsbad, Calif.). An optional C-terminal V5 epitope tag is present for easy detection of expressed fusion proteins using an Anti-V5 Antibody. An optional C-terminus polyhistidine (6×His) tag is also present to enable rapid purification and detection of expressed proteins. A bacterial ribosomal binding site downstream from the loxP site makes transcription initiation in *E. coli* possible. Though this combination of elements is specific for pUni/V5-His version A cloning vector, many similar cloning and expression vectors are commercially available or can be assembled from sequences and by methods well known in the art. pUni/V5-His version A is a 2.2 kb double stranded plasmid (see FIGS. 3 and 5).

Figure 6:
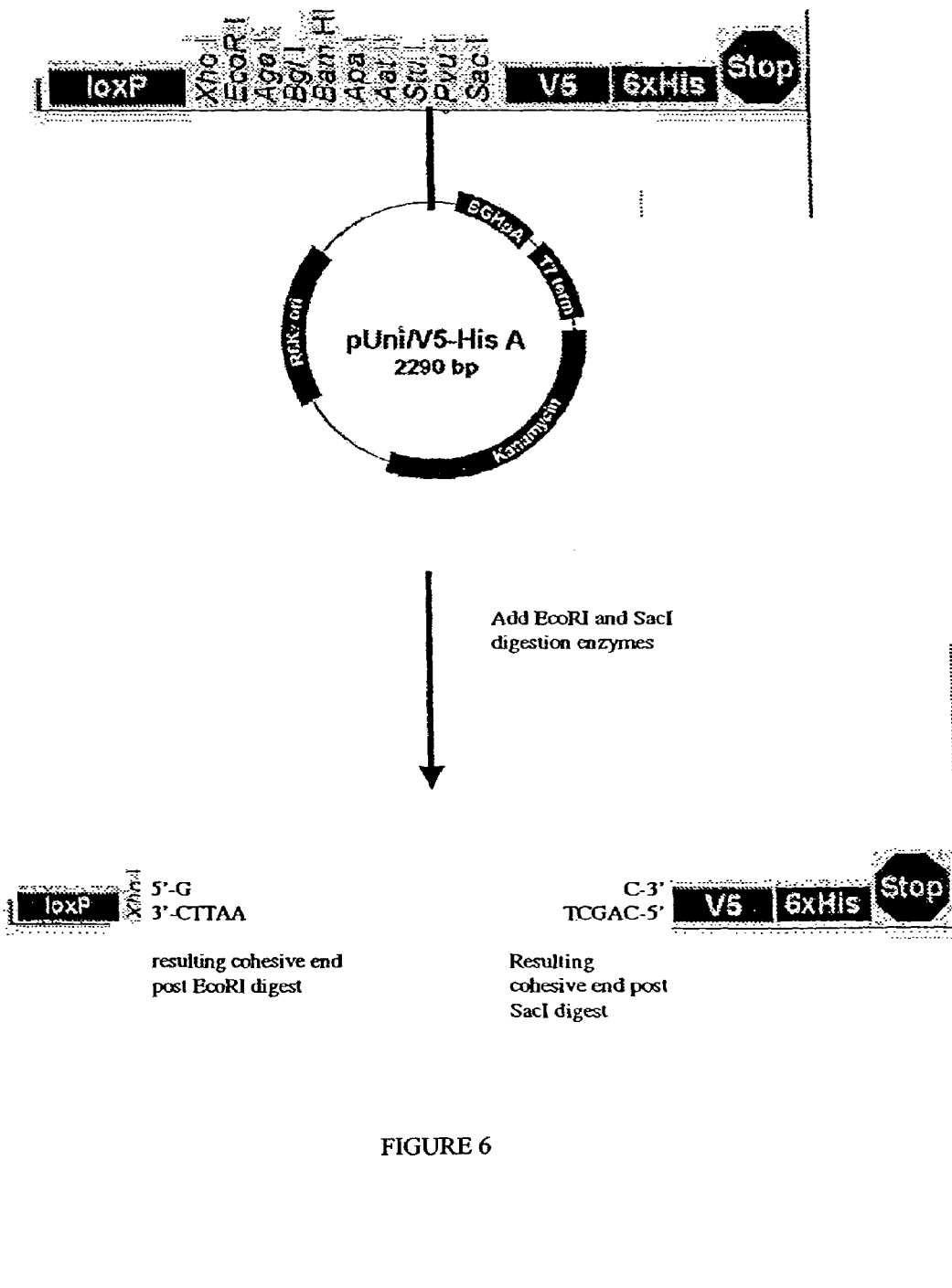
FIG. 6 illustrates digestion of pUni/V5-His version A with EcoRI and SacI, and the resulting cohesive end sequences. The resulting cohesive end on the left side of the figure near the loxP element is the resulting cohesive end post EcoRI digestion. The resulting cohesive end on the right side of the figure near the V5 element is the resulting cohesive end post SacI digestion. Vector elements including a loxP, V5, and 6xHis element as well as a stop codon in frame with these elements are indicated.

Construction of a topoisomerase I charged cloning vector from pUni/V5-His version A is accomplished by endonuclease digestion of the vector, followed by complementary annealing of synthetic oligonucleotides and site-specific cleavage of the heteroduplex by Vaccinia topoisomerase I. SacI and EcoRI are two of the many restriction endonuclease sites present within the multiple cloning site of pUni/V5-His version A, (See FIG. 3). Digestion of pUni/V5-His version A with the corresponding restriction enzymes, SacI and EcoRI will leave cohesive ends on the vector (5'-AGCT-3' and 5'-AATT-3', FIG. 6). These enzymes are readily available from numerous vendors including New England Biolabs, (Beverly, Mass. Catalogue Nos. RO156S, SacI and RO101S, EcoRI). The digested pUni/V5-His version A is easily separated from the digested fragments using isopropanol precipitation. These and other methods for digesting and isolating DNA are well known to those skilled in the art, (Sambrook et al., (1989) *Molecular Cloning, A Laboratory Manual*. Second edition. Cold Spring Harbor Laboratory Press; pages 5.28-5.32.)

The purified, digested vector is then incubated with two specific oligonucleotide adapters and T4 DNA ligase. The adapters are oligonucleotide duplexes containing ends that are compatible with the SacI and EcoRI ends of the vector. One of skill in the art will readily appreciate that other adapter oligonucleotides with appropriate sequences can be made for other vectors having different restriction sites. Following incubation with T4 DNA ligase, the vector containing the ligated adapters is purified using isopropanol.

The adapter duplex that results from the annealing of TOPO D1 and TOPO D2 has a single-stranded EcoRI overhang at one end and a 12 nucleotide single stranded overhang at the other end.

The first adapter oligonucleotide, (TOPO D1), has complementation to the EcoRI cohesive end, 3'-TTAA-5'. Furthermore, TOPO D1 has an additional 24 bp including the topoisomerase consensus pentapyrimidine element 5'-CCCTT located 16 bp upstream of the 3' end. The remaining sequence and size of TOPO D1 adapter oligo is variable, and can be modified to fit a researcher's particular needs. In the current embodiment 5'-<u>AATT</u>GAT CCCTTCACCGACATAGTACAG-3' (SEQ ID NO:5) is the full sequence of the adapter used.

The second adapter oligonucleotide, (TOPO D2), must have full complementation to TOPO D1. TOPO D2 complements directly 5' of the EcoRI cohesive flap, extending the bottom strand of the linearized vector. Additionally, TOPO D2 contains the sequence 3'-GTGG, which is the target sequence, and single-stranded overhang after topoisomerase cleavage, for directional cloning. In this embodiment, the single stranded overhang was chosen to complement the Kozak sequence known to help expression of ORFs in eukaryotic cells by increasing the efficiency of ribosome binding on the mRNA, however, sequence and length are highly variable to meet the specific needs of individual users. The complete sequence of TOPO D2 is 3'-CTAGGGAA GTGG-5' (SEQ ID NO:6).

Similar to above, the adapter duplex that results from the annealing of oligonucleotides TOPO D4 and TOPO D5 has a single-stranded SacI overhang at one end, and a 12 nucleotide single-stranded overhang at the other end.

The third adapter oligonucleotide, (TOPO D5), has complementation to the SacI cohesive end, 3'-TCGA-5'. Similar to TOPO D1, TOPO D5 has additional bases creating a single stranded overhang. The length and sequence can vary based on the needs of the user. In the current embodiment TOPO D5's sequence is 5'-AAGGGCG<u>AGCT</u>-3' (SEQ ID NO:7).

The fourth adapter oligonucleotide, (TOPO D4), has full complementation to TOPO D5, and complements directly 5' of the SacI cohesive flap extending the top strand of the linearized vector. TOPO D4 also contains the topoisomerase consensus sequence 5'-CCCTT. The remaining sequence and size of TOPO D4 adapter oligo is variable and can be modified to fit a researcher's particular needs. In the current embodiment, the sequence of TOPO D4 is 3'-GACATGATA-CAGTTCCCGC-5' (SEQ ID NO:8), which includes an additional 12 bp single stranded overhang.

These adapter oligonucleotides can be chemically synthesized using any of numerous techniques, including the phosphoramadite method (Caruthers et al., *Meth. Enzymol.* 154: 287-313, 1987). This and other methods for the chemical synthesis of oligos are well known to those of ordinary skill in the art.

Figure 7:
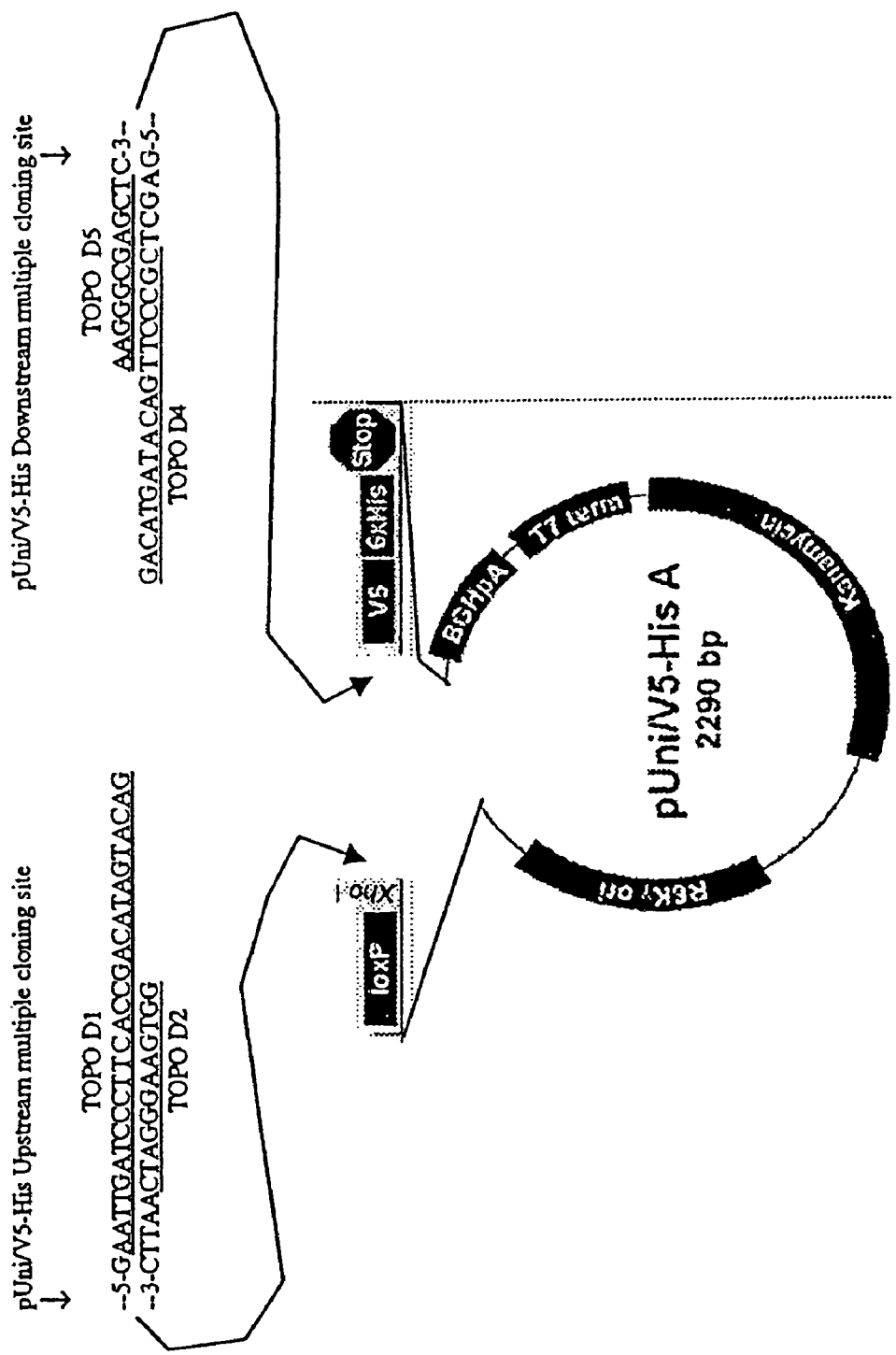
FIG. 7 illustrates the addition of adapter oligonucleotides to the digested vector in the presence of DNA ligase. The reaction yields the exhibited linearized, adapted vector. Adapter sequences are underlined for demarcation. The four adaptor oligonucleotides have the following sequences.

Complementary annealing of the purified digested vector and the adapter oligonucleotides is done by incubation of the DNA in the presence of T4 DNA ligase. Typical ligation reactions are performed by incubation of a cloning vector with suitable DNA fragments in the presence of ligase and an appropriate reaction buffer. Buffers for ligation reactions should contain ATP to provide energy to for the reaction, as well as, reducing reagents like dithiothreitol and pH stabilizers like Tris-HCl. The ratio of concentrations for the cloning vector and the DNA fragments are dependent on each individual reaction, and formulae for their determination are abundant in the literature, (See e.g., *Protocols and Applications Guide* (1991), Promega Corporation, Madison, Wis., p.45). T4 Ligase will catalyze the formation of a phosphodiester bond between adjacent 5'-phosphates and 3'-hydroxyl termini during the incubation. Cohesive end ligation can generally be accomplished in 30 minutes at 12-15° C., while blunt end ligation requires 4-16 hours at room temperature, (Ausubel et al., (1992) Second Edition; *Short Protocols in Molecular Biology*, John Wiley & Sons, Inc., New York, N.Y., pages 3.14-3.37), however parameter range varies for each experiment. In the current embodiment, purified, digested pUni/V5-His version A and the adapter oligos were incubated in the presence of T4 ligase and a suitable buffer for sixteen hours at 12.5° C. The resulting linearized and adapted vector comprises the purified cloning vector attached to the adapter oligonucleotides through base pair complementation and T4 ligase-catalyzed, phosphodiester bonds (see FIG. 7).

Efficient modification of the adapted vector with topoisomerase requires the addition of an annealing oligo to generate double stranded DNA on TOPO D1's and TOPO D4's single stranded overhangs. Vaccinia topoisomerase I initially binds non-covalently to double stranded DNA. The enzyme then diffuses along the duplex until locating and covalently attaching to the consensus pentapyrimidine sequence 5'-CCCTT, forming the topoisomerase adapted complex, (See Shuman et al., U.S. Pat. No. 5,766,891). Modification of the adapted vector takes place in the absence of DNA ligase to prevent the formation of phosphodiester bonds between the adapted vector and the annealing oligo, since phosphodiester bonds in the non-scissile strand will prevent the dissociation of the leaving group upon cleavage, (FIGS. 8 and 9).

The annealing oligonucleotide, (TOPO D3), must have complementation to the single stranded DNA overhangs of TOPO D1 and TOPO D4. In the current embodiment the overhangs both share the following sequence, 5'-GACATAG-TACAG-3' (SEQ ID NO:9). Therefore, TOPO D3 has the following sequence, 3'-CTGTATCATGTCAAC-5' (SEQ ID NO:10), which comprises full complementation to the adapter oligos' single stranded overhang and an additional 3 bp overhang, 3'-AAC-5'.

Incubation of the adapted vector with the annealing oligo in the presence of topoisomerase will create double stranded DNA to which topoisomerase can non-covalently bind, (FIG. 10). Bound topoisomerase will search the double stranded DNA by a facilitated diffusion mechanism, until the 5'-CCCTT recognition motif is located. Cleavage of the phosphodiester backbone of the scissile strand 3' of the motif is catalyzed via a nucleophilic attack on the 3' phosphorous atom of the preferred oligonucleotide cleavage sequence 5'-CCCTT↓, resulting in covalent attachment of the DNA to the enzyme by a 3'-phosphotyrosyl linkage, (See Shuman et al., (1989) *Proc. Natl. Acad. Sci. U.S.A.* 86, 9793-9796). Cleavage of the scissile strand creates a double stranded leaving group comprising the 3' end adapter oligo, downstream from the 5'-CCCTT motif, and the annealing oligo TOPO D3. Although the leaving group can religate to the topoisomerase-modified end of the vector via 5' hydroxyl-mediated attack of the phosphotyrosyl linkage, this reaction is disfavored when the leaving group is no longer covalently attached to the vector. The addition of T4 polynucleotide kinase and ATP to the cleavage/religation reaction further shifts the equilibrium toward the accumulation of trapped topoisomerase since the kinase can phosphorylate the 5' hydroxyl of the leaving group to prevent the rejoining from taking place, (Ausubel et al., (1992) Second Edition; *Short Protocols in Molecular Biology*, John Wiley & Sons, Inc., New York, N.Y., pp. 3.14-3.30). The resulting linearized vector comprises a blunt end from the TOPO D4/D3 leaving group and a single stranded overhang bearing end from the TOPO D1/D3 leaving group, (FIG. 11). Both of the linearized cloning vector's ends are charged with topoisomerase, enabling fast, efficient and directional topoisomerase mediated insertion of an acceptor molecule.

Although the above example details the modification of pUni/V5-His version A to form the topoisomerase-modified directional cloning vector, a person of ordinary skill in the art will appreciate how to apply these methods to any plasmid, cosmid, virus, or other DNA. It should also be noted that this example demonstrates a vector containing a 5' single stranded overhang comprising the sequence 5'-GGTG-3', however the design of adapter duplexes and annealing oligonucleotides would allow one of skill in the art to custom design overhangs of any sequence or length at one or both ends of a given vector.

Specifically, any plasmid, cosmid, virus or other DNA can be modified to possess a single stranded overhang of any convenient sequence and length. These are the basic steps: the vector is first subjected to a treatment that is known to linearize the DNA. Common procedures include, but are not limited to, restriction digestion and treatment with topoisomerase II. Following linearization, a custom single stranded overhang is added. In the above example, complementary oligonucleotides are added to the sticky ends of a restriction digestion giving the desired single stranded overhang, however single stranded overhang forming oligonucleotides can be added by T4 blunt end ligation, as well. The single stranded overhang sequence is exposed by a topoisomerase I mediated, single strand nicking. In turn, this single stranded overhang can be used to directionally insert a PCR product comprising one or more complimentary nucleotide sequences.

Likewise, topoisomerase modification can be applied to any double-stranded plasmid, cosmid, virus or other piece of DNA. Methods for the attachment of topoisomerase I to double stranded DNA are well known in the art, (See Shuman et al., U.S. Pat. No. 5,766,891). The strategic placement of topoisomerase on to a piece of double stranded DNA is determined by the incorporation of a topoisomerase I consensus sequence, (See Shuman et al., U.S. Pat. No. 5,766,891). The topoisomerase I will bind the double stranded DNA, nick the scissile strand thus revealing the predetermined single-stranded overhang sequence, and ligate the incoming PCR product in the correct, single stranded overhang mediated orientation.

EXAMPLE 2

As an example of the application of the present invention to another plasmid, pCR® 2.1, (FIGS. 4 and 12), was modified to create a topoisomerase I adapted vector with a custom single stranded sequence.

The pCR® 2.1 plasmid is 3.9 kb T/A cloning vector. Within the sequence of this vector are many uniquely designed elements. These elements include an f1 origin, a ColE1 origin, a kanamycin resistance gene, an ampicillin resistance gene, a LacZ-alpha fragment and a multiple cloning sequence located within the LacZ-alpha fragment allowing for blue-white selection of recombinant plasmids. The multiple cloning sequence, (FIG. 4) of the pCR® 2.1 plasmid contains; numerous restriction sites, including but not limited to, HindIII, SpeI and EcoRI; M13 forward and reverse primers and a T7 RNA polymerase promoter.

Figure 13:
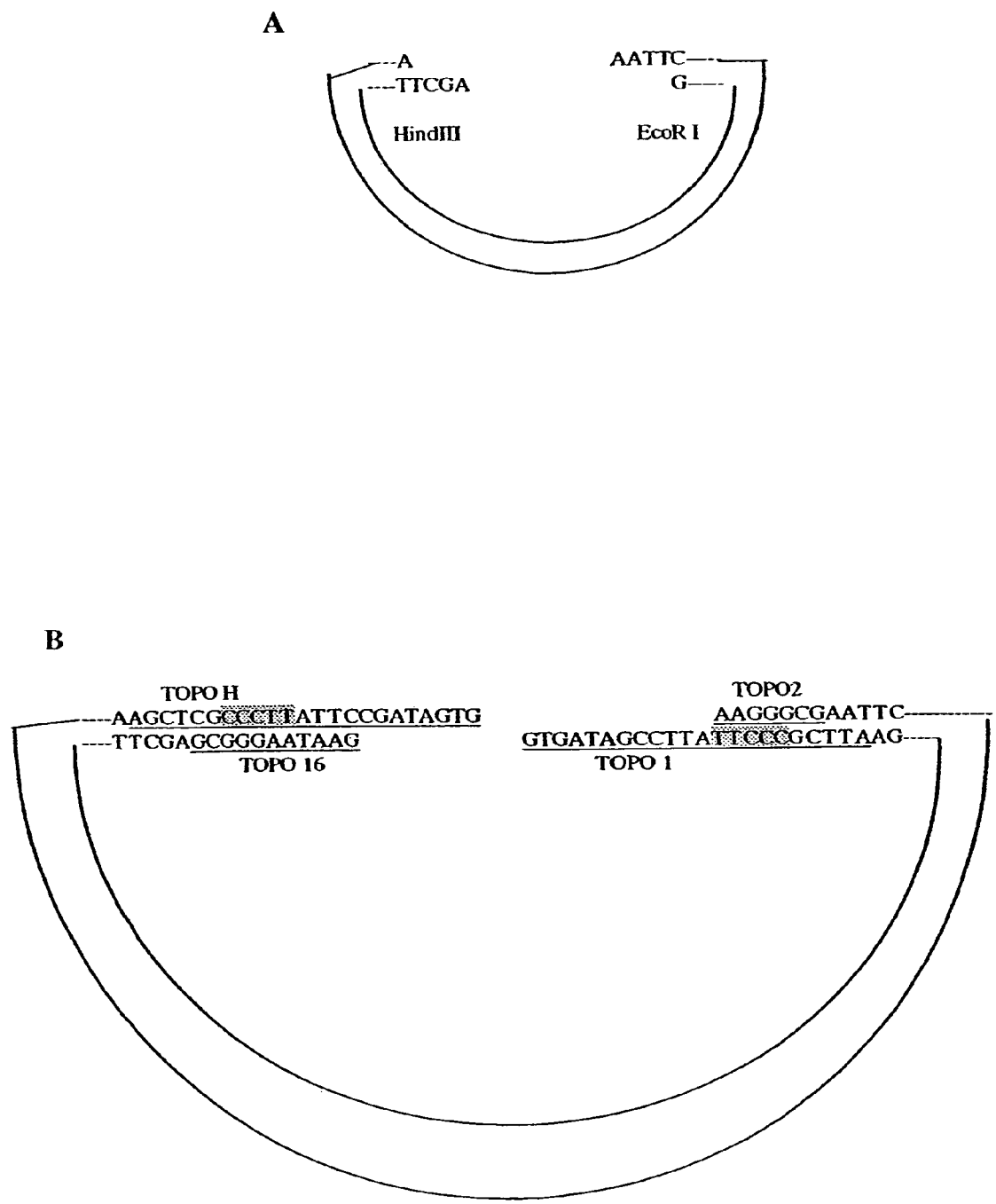

Construction of the topoisomerase I charged vector possessing a custom single stranded sequence consists of endonuclease digestion followed by complementary annealing of synthetic oligonucleotides and the site specific cleavage of the heteroduplex by Vaccinia topoisomerase I. Digestion of the PCR® 2.1 plasmid with the restriction enzymes HindIII, SpeI and EcoRI leaves HindIII and EcoRI cohesive ends on the vector (FIG. 13). The dissociated fragment of pCR® 2.1 downstream from the HindIII cleavage site is further cleaved with SpeI in order to reduce its size. By reducing the size of the fragment, the digested vector is easily purified away from the smaller digested pieces by isopropanol precipitation. These enzymes are readily available from numerous vendors including New England Biolabs, (Beverly, Mass., Catalogue Nos.; RO104S, HindIII; RO133S, SpeI; RO101S, EcoRI). Methods for the digestion and the isolation of DNA are well known to those skilled in the art, (Sambrook et al., supra, 1989).

The purified digested vector is incubated with four adapter oligonucleotides and T4 DNA ligase. These adapter oligonucleotides are designed to have complementation to either the HindIII cohesive end, the EcoRI cohesive end, or to each other. Following incubation with T4 DNA ligase the adapted vector is purified using isopropanol.

The first adapter oligonucleotide, (TOPO H), has complementation to the HindIII cohesive end, 3'-TCGA-5'. Furthermore, TOPO H has an additional 24 bp including the topoisomerase consensus pentapyrimidine element 5'-CCCTT located 19 bp upstream of the 3' end. The remaining sequence and size of TOPO H adapter oligo is variable, and can be modified to fit a researcher's particular needs. In the current embodiment 5'-AGCTCGCCCTTATTCCGATAGTG-3' (SEQ ID NO: 11) is the full sequence of the adapter used.

The second adapter oligonucleotide, (TOPO 16), must have full complementation to TOPO H. TOPO 16 complements directly 5' of the HindIII cohesive end, extending the bottom strand of the linearized vector. Additionally, TOPO 16 contains the sequence 3'-TAAG, which is the chosen single stranded sequence for directional cloning. The complete sequence of TOPO 16 is 3'-GCGGGAATAAG-5', (SEQ ID NO:12).

The third adapter oligonucleotide, (TOPO 1), has complementation to the EcoRI cohesive end, 3'-TTAA-5'. Similar to TOPO H, TOPO 1 has additional bases containing the topoisomerase I consensus sequence CCCTT located 12 bp upstream of the 3' end. The length and sequence of TOPO 1 can vary based on the needs of the user. In the current embodiment TOPO 1's sequence is 5'-AATTCGCCCTTATTCCGATAGTG-3' (SEQ ID NO:13).

The fourth adapter oligonucleotide, (TOPO 2), has full complementation to TOPO 1, and complements directly 5' of the EcoRI cohesive end extending the top strand of the linearized vector. In the current embodiment, the sequence of TOPO 2 is 3'-GCGGGAA-5'.

Complementary annealing of the purified digested vector and the adapter oligonucleotides is done by incubation of the DNA in the presence of T4 DNA ligase. T4 Ligase will catalyze the formation of a phosphodiester bond between adjacent 5'-phosphates and 3'-hydroxyl termini during the incubation. In the current embodiment, purified, digested pCR® 2.1 and the adapter oligos were incubated in the presence of T4 ligase and a suitable buffer for sixteen hours at 12.5° C. The resulting linearized and adapted vector comprises the purified cloning vector attached to the adapter oligonucleotides through base pair complementation and T4 ligase-catalyzed, phosphodiester bonds (FIG. 13). Ligation techniques are abundant in the literature, (see Ausubel et al., (1992) Second Edition; *Short Protocols in Molecular Biology*, John Wiley & Sons, Inc., New York, N.Y., pp. 3.14-3.37).

Charging of the adapted vector with topoisomerase requires the addition of annealing oligonucleotides to generate double stranded DNA on TOPO H's and TOPO 1's single stranded overhangs. Charging of the adapted vector takes place in the absence of DNA ligase to prevent the formation of phosphodiester bonds between the adapted vector and the annealing oligo, since phosphodiester bonds in the non-scissile strand will prevent the dissociation of the leaving group upon cleavage (see FIG. 9).

The annealing oligonucleotide, (TOPO 17), must have complementation to the single stranded DNA overhang of TOPO H. In the current embodiment the overhang has the following sequence, 5'-CGATAGTG-3'. Therefore, TOPO 17 has the following sequence, 3'-GCTATCAC-5', which comprises full complementation to the single stranded overhang of the adapter oligonucleotides.

The annealing oligonucleotide, (TOPO 3), must have complementation to the single stranded DNA overhang of TOPO 1. In the current embodiment the overhang has the following sequence, 3'-GTGATAGCCTTA-5' (SEQ ID NO: 14). Therefore, TOPO 3 has the following sequence, 5'-CAACACTATCGGAAT-3' (SEQ ID NO: 15), which comprises full complementation to the adapter oligonucleotide's single stranded overhang and an additional 3 bp overhang, 5'-CAA-3'.

Incubation of the adapted vector with the annealing oligo in the presence of topoisomerase will create double stranded DNA to which topoisomerase can non-covalently bind, (FIG. 14). Bound topoisomerase will search the double stranded DNA by a facilitated diffusion mechanism, until the 5'-CCCTT recognition motif is located. Cleavage of the phosphodiester backbone of the scissile strand 3' of the motif will result in the covalent attachment of the DNA to the enzyme by a 3'-phosphotyrosyl linkage, (Shuman et al., *Proc. Natl. Acad. Sci. U.S.A.* 86:9793-9796, 1989). Cleavage of the scissile strand creates a double stranded leaving group comprising the 3' end the adapter oligos, downstream from the 5'-CCCTT motif, and the complementary annealing oligonucleotide. The leaving group can religate to the topoisomerase adapted vector through its 5'hydroxyl's attack of the phosphotyrosyl linkage, also catalyzed by topoisomerase. Addition of T4 polynucleotide kinase to the equilibrium reaction prevents the back reaction via the kinase-mediated phosphorylation of the leaving group's 5' hydroxyl, (Ausubel et al., (1992) Second Edition; *Short Protocols in Molecular Biology*, John Wiley & Sons, Inc., New York, N.Y., pp. 3.14-3.30). The resulting linearized vector comprises a blunt end from the TOPO ⅓ leaving group and a single stranded sequence end from the TOPO H/17 leaving group, (FIG. 15). Both of the linearized cloning vector's ends are charged with topoisomerase, enabling fast, efficient and directional topoisomerase mediated insertion of an acceptor molecule.

Directional cloning according to the invention.

This invention also provides a method for directional cloning of DNA. In the following example, the topoisomerase-charged ds nucleic acid vector according to the present invention constructed from pUni/V5-His version A was used for the directional insertion of ORFs from the GeneStorm™ Expression Ready Clones, (Invitrogen Corp., Carlsbad, Calif.). The modified pUni vector was selected for the cloning of these ORFs because the added target sequence, which becomes a single strand overhang upon topoisomerase cleavage of the vector, has homology to the Kozak sequence known to enhance ORF expression. Note, however, that, as before, any plasmid, cosmid, virus or other DNA could be modified to possess the necessary single stranded sequence. Likewise, any DNA fragment could be modified to possess a homologous sequence to any single stranded overhang of a vector. As a point of interest, the sequence of the single stranded overhang can effect directional cloning efficiencies. For example, single stranded overhangs with low GC content will have lower annealing stability, also single stranded overhangs that have high complementation to both ends of a DNA fragment to be cloned will loose the capability to direct these DNA inserts. Thus the sequence of a single stranded overhang should be carefully designed to avoid these and similar problems.

EXAMPLE 3

The present invention is particularly useful in the directional insertion of PCR products into vectors constructed according to the present invention. In the PCR amplification of the desired insert, the PCR primers are designed so as to complement identified sequences of the insert(s) that are to be directionally cloned into the topoisomerase-charged ds nucleic acid vector of the present invention. The primer designed to bind upstream of the DNA's coding strand is modified with an additional complementary nucleotide sequence on its 5' end. The resulting PCR product will possess a complementary sequence allowing single stranded overhang mediated directional insertion into the topoisomerase-charged ds nucleic acid cloning vector of the present invention and subsequent expression of the product.

One embodiment comprises introducing to a donor duplex DNA substrate a single stranded overhang site by PCR amplifying the donor duplex DNA molecule with the 5' oligonucleotide primer containing the single stranded overhang. PCR amplification of a region of DNA is achieved by designing oligonucleotide primers that complement a known area outside of the desired region. In a preferred embodiment the primer that has homology to the coding strand of the double stranded region of DNA will possess an additional sequence of nucleotides complementary to the single strand overhang of the topoisomerase-charged ds nucleic acid cloning vector of the preset invention.

Using the present invention in a high throughput format, we selected eighty-two known ORFs from the GeneStorm™ expression system, (Invitrogen Corporation, Carlsbad, Calif.) for directional cloning into the topoisomerase-charged ds nucleic acid vector of the present invention, however, any sequence of DNA can be selected as desired by individual users. For each of these ORFs, primers are designed with homology to the coding and the non-coding strands. To clone PCR products in a directional fashion into the modified pUni/V5-His version A topoisomerase-charged ds nucleic acid vector of the present invention as described in example 1, one primer of a given pair was modified to contain primer of a given pair was modified to contain the nucleotide sequence complementary to the single strand overhang contained within the vector. In the current example, the coding primer contained the added sequence 5'-CACC-3', which complements the 'single stranded overhang', 3'-GTGG-5', of the topoisomerase-charged ds nucleic acid cloning vector of the present invention. PCR amplification of the above ORFs with their respective primers will produce double stranded DNA fragments, which possess the single strand overhang at their 5' end, (FIG. 16). We used pfu polymerase in our PCR amplification, but it is well-known that PCR reactions can be performed with either a non-thermophilic polymerase such as pfu or with a thermophilic polymerase like Taq followed by a blunting step to remove the non-template nucleotide these enzymes leave at the end of PCR products.

In the present example, 0.1 microgram of each primer was combined with 0.05 microgram of DNA containing an ORF in a PCR reaction mix totaling 50 microliters total volume. Besides the primers and vector, the reaction mix also contained water, PCR buffer salts, 10 mM dNTPs and 1.25 units of pfu polymerase. Thermal cycling temperatures were as follows; an initial 94° C. denaturation; followed by 25 repetitions of 94° C. denaturation, 55° C. primer annealing, and 72° C. elongation, each at one minute; and ended with a 72° C., fifteen minute elongation. However these parameters will vary with each DNA fragment to be amplified. PCR amplification techniques are well known to those skilled in the art, (Ausubel et al., (1992) Second Edition; Short Protocols in Molecular Biology, John Wiley & Sons, Inc., New York, N.Y., pp. 15.3-15.4), as are techniques for the conversion of 3' overhangs to blunt end termini, (*Protocols and Applications Guide*, Promega Corp.; Madison Wis., pp. 43-44, 1989).

Incubation of the PCR amplified donor duplex DNA containing the complementary nucleotide sequence with the modified pUni/V5-His version A topoisomerase-charged ds nucleic acid vector of the present invention results in the directional cloning of the donor DNA. For example, the eighty-two ORFs from the GeneStorm™ clone collection (Invitrogen Corporation, Carlsbad, Calif.) were amplified using adapted primers containing a complementary nucleotide sequence. Amplification of the 82 GeneStorm™ ORFs with the described modified primer pairs resulted in PCR products that had the complementary nucleotide sequence at their 5' end. This ORF PCR product is combined with 10 ng of topoisomerase-charged ds nucleic acid cloning vector of the present invention in either sterile water or a salt solution. The reaction is mixed gently and incubated for 5 minutes at room temperature (22-23° C.). After five minutes, we placed the reaction on ice then proceeded to the One Shot® Chemical Transformation or Electroporation, (Invitrogen Corporation, Carlsbad, Calif., Catalogue # C4040-10 and C4040-50, respectively), (*Invitrogen TOPO Cloning Protocol*. Invitrogen Corp.). Topoisomerase had joined the adjacent strands of the vector and the product by catalyzing a rejoining reaction (FIG. 17). DNA fragments constructed with the complementary nucleotide sequence at their 5' ends were thus correctly inserted into topoisomerase-charged ds nucleic acid cloning vectors of the present invention with a high efficiency.

Directional insertion of DNA fragments containing 5' sequences complementary into ds nucleic acid cloning vectors according to certain embodiments of the present invention occurs with greater than 90% efficiency as shown by sequencing multiple colonies of transformed host cells. In the current example, the topoisomerase-charged ds nucleic acid cloning vectors of the present invention containing the GeneStorm™ ORFs were incubated with transformation competent *E. coli* host cells. In seventy-four of the transformation reactions, the directional cloning of the ORFs into the topoisomerase-charged ds nucleic acid cloning vector of the present invention occurred in at least seven of the eight colonies picked, and fifty-nine of these cloning reactions were directional in all eight colonies picked. The overall directional cloning score was 609 of 656, thus, directional insertion was present in over 93% of the clones picked (see Table 1 below).

EXAMPLE 4

Figure 4:
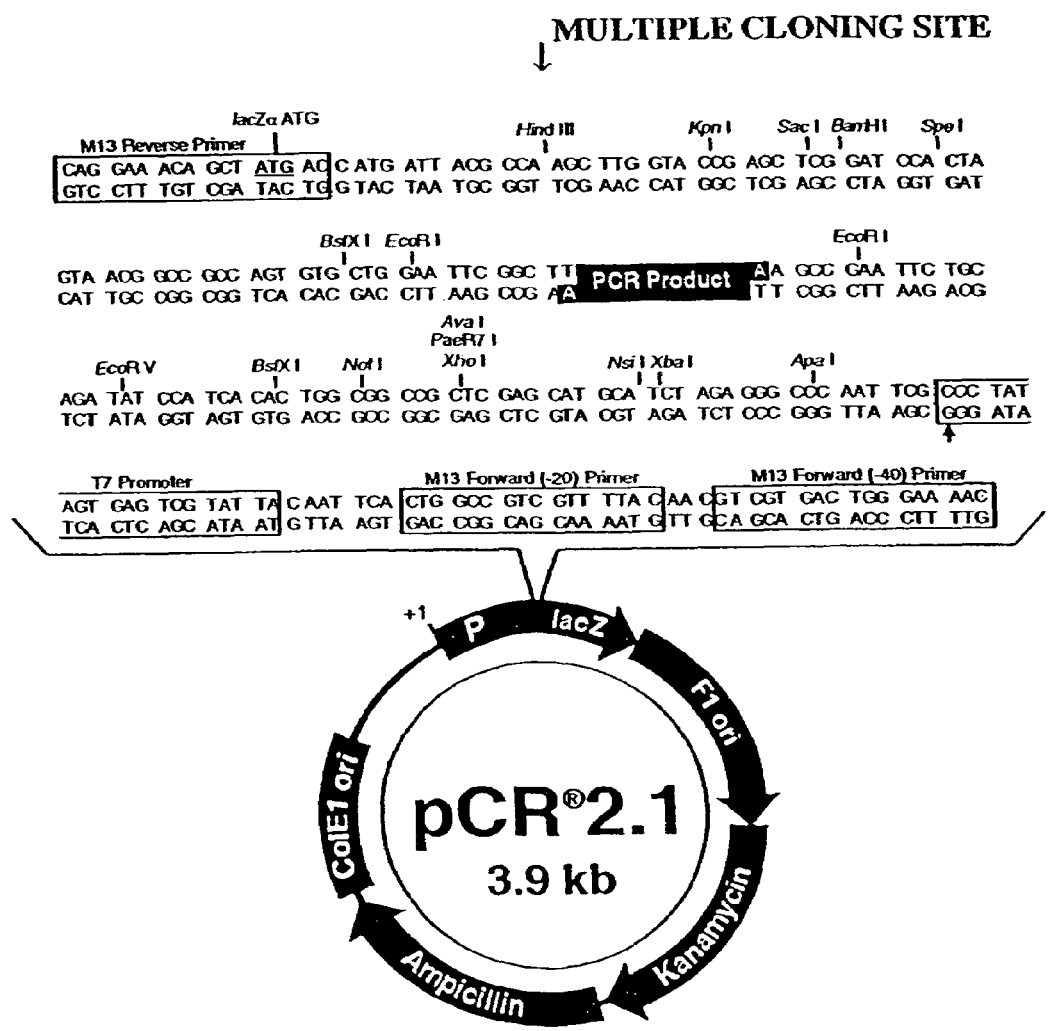
FIG. 4 provides the nucleotide sequence and the location of restriction endonuclease recognition sequences of the Multiple Cloning Site of pCR 2.1 (SEQ ID NO:17), and a plasmid map of this vector. HindIII cloning site is located at nucleotide 234, SpeI is at nucleotide 258 and EcoRI is at nucleotide 283 and nucleotide 299 (nucleotide positions as in SEQ ID NO:17). The vector is 3906 nucleotides. LacZ alpha fragment: bases 1-587; M13 reverse priming site: bases 205-221; Multiple cloning site: bases 234-355; T7 promoter/priming site: bases 362-381; M13 forward (−20) priming site: bases 389-404; M13 Forward (−40) priming site: bases 408-424; f1 origin: bases 546-960; kanamycin resistance ORF: bases 1294-2088; ampicillin resistance ORF: bases 2106-2966; ColE1 origin: bases 3111-3784. The illustrated vector represents the pCR®2.1 vector with a PCR product inserted by TA Cloning®. Note that the inserted PCR product is flanked on each side by EcoRI sites. The arrow indicates the start of transcription for the T7 RNA polymerase.

In a similar example, using the above described modified pCR® 2.1 topoisomerase-charged ds nucleic acid vector of the present invention, a PCR-generated ORF encoding Green Fluorescent Protein (GFP) was directionally cloned in frame with the lacZ α fragment present in the vector (see FIG. 4). The primers used to amplify the GFP gene contained the requisite complementary nucleotide sequence 5'-ATTC-3', and the known sequence for translation initiating methionine, 5'-ATG-3'. Using the necessary cloning steps noted above, the PCR amplified GFP was inserted into the vector and transformed cells were grown on solid Agar plates. Glowing colonies represented a correctly inserted PCR product (see Table 2 below).

These data represent a substantial improvement over the current state of the art in cloning, and furthermore present an invention in cloning that is highly compatible with high throughput techniques. Given directional cloning efficiencies greater that 90%, a user need only screen two colonies for each cloned DNA fragment. Thus, on a 96-well plate, forty-eight separate clones can be screened for directional insertion, 400% more than current cloning techniques. Use of this invention will streamline many high throughput gene expression operations, and allow them to run at fraction of their current costs.

TABLE 1

Directional Cloning of ORFs using a topoisomerase-charged ds nucleic acid cloning vector of the present invention

| Positive colonies. dPCR reactions | Clones tested |
|---|---|
| 8/8 | 59 |
| 7/8 | 15 |
| 6/8 | 2 |
| 5/8 | 1 |
| 4/8 | 3 |
| 3/8 | 2 |

TABLE 2

In frame and directional insertion of GFP into modified pCR2.1 topoisomerase-charged ds nucleic acid cloning vector of the present invention

| PCR product's 5' sequence | Percentage of correct inserts | Total white colonies (contain a recombinant plasmid) |
|---|---|---|
| 5'-ATTCATG-3' homologous | 86% | 457 |
| 5'-CAAGATG-3' non-homologous | 35% | 118 |
| 5'-ATTCGGATG-3' frame shift | 0% | 268 |
| VECTOR ONLY | 0% | 31 |

Although the invention has been described with reference to the above examples, it will be understood that modifications and variations are encompassed within the spirit and scope of the invention. Accordingly, the invention is limited only by the following claims.

What is claimed is:

1. A kit comprising
   a) a first double stranded (ds) nucleic acid molecule, which comprises a first topoisomerase covalently bound at a 3' terminus of a first end, and a second topoisomerase covalently bound at a 3' terminus of a second end,
   said first end further comprising a first 5' overhang and said second end further comprising a blunt end, a 3' thymidine overhang, or a second 5' overhang, wherein said first 5' overhang is different from said second 5' overhang; and
   b) a plurality of second ds nucleic acid molecules, wherein each ds nucleic acid molecule in the plurality comprises a first blunt end, and wherein the first blunt end comprises a 5' nucleotide sequence complementary to the first 5' overhang of the first ds nucleic acid molecule.

2. The kit of claim 1, wherein the second ds nucleic acid molecules in the plurality comprise transcriptional regulatory elements, translational regulatory elements, or a combination thereof.

3. The kit of claim 1, wherein the second ds nucleic acid molecules in the plurality comprise nucleotide sequences encoding a peptide.

4. An isolated double stranded (ds) nucleic acid molecule which is a pUni5-His version A vector (SEQ ID NO:16), comprising a recombinase site, an origin of replication, a selectable marker, a first topoisomerase covalently bound at a 3' terminus of a first end, and a second topoisomerase covalently bound at a 3' terminus of a second end, said first end further comprising a 5' overhang and said second end further comprising a blunt end.

5. The isolated double stranded nucleic acid molecule of claim 4, wherein the 5' overhang of the first end comprises 5'-GGTG-3'.

6. A collection of reagents comprising
   a) a first double stranded (ds) nucleic acid molecule, which comprises a first topoisomerase covalently bound at a 3' terminus of a first end, and a second topoisomerase covalently bound at a 3' terminus of a second end,
   said first end further comprising a first 5' overhang and said second end further comprising a blunt end, a 3' thymidine overhang, or a second 5' overhang, wherein said first 5' overhang is different from said second 5' overhang; and
b) a second ds nucleic acid molecule, wherein the second ds nucleic acid molecule comprises a first blunt end, and wherein the first blunt end comprises a 5' nucleotide sequence complementary to the first 5' overhang of the first ds nucleic acid molecule.

7. The collection of reagents of claim 6, wherein the second ds nucleic acid molecule comprises transcriptional regulatory elements, translational regulatory elements, or a combination thereof.

8. The collection of reagents of claim 6, wherein the second ds nucleic acid molecule comprises nucleotide sequences encoding a peptide.

9. The collection of reagents of claim 6, wherein the first ds nucleic acid molecules are in a first tube and the second ds nucleic acid molecules are in a second tube.

10. The collection of reagents of claim 9, wherein the first tube and the second tube are part of a kit.

* * * * *

SEQUENCE LISTING

```
<160> NUMBER OF SEQ ID NOS: 34

<210> SEQ ID NO 1
<211> LENGTH: 12
<212> TYPE: DNA
<213> ORGANISM: Artificial sequence
<220> FEATURE:
<223> OTHER INFORMATION: Vaccinia topoisomerase cleavable sequence

<400> SEQUENCE: 1
gcccttattc cc                                                      12

<210> SEQ ID NO 2
<211> LENGTH: 12
<212> TYPE: DNA
<213> ORGANISM: Artificial sequence
<220> FEATURE:
<223> OTHER INFORMATION: Vaccinia topoisomerase cleavable sequence

<400> SEQUENCE: 2
tcgcccttat tc                                                      12
```

<210> SEQ ID NO 3
<211> LENGTH: 12
<212> TYPE: DNA
<213> ORGANISM: Artificial sequence
<220> FEATURE:
<223> OTHER INFORMATION: Vaccinia topoisomerase cleavable sequence

<400> SEQUENCE: 3
tgtcgccctt at                                                        12

<210> SEQ ID NO 4
<211> LENGTH: 12
<212> TYPE: DNA
<213> ORGANISM: Artificial sequence
<220> FEATURE:
<223> OTHER INFORMATION: Vaccinia topoisomerase cleavable sequence

<400> SEQUENCE: 4
gtgtcgccct ta                                                        12

<210> SEQ ID NO 5
<211> LENGTH: 28
<212> TYPE: DNA
<213> ORGANISM: Artificial sequence
<220> FEATURE:
<223> OTHER INFORMATION: Adapter oligonucleotide

<400> SEQUENCE: 5
aattgatccc ttcaccgaca tagtacag                                       28

<210> SEQ ID NO 6
<211> LENGTH: 12
<212> TYPE: DNA
<213> ORGANISM: Artificial sequence
<220> FEATURE:
<223> OTHER INFORMATION: Adapter oligonucleotide

<400> SEQUENCE: 6
ggtgaaggga tc                                                        12

<210> SEQ ID NO 7
<211> LENGTH: 11
<212> TYPE: DNA
<213> ORGANISM: Artificial sequence
<220> FEATURE:
<223> OTHER INFORMATION: Adapter oligonucleotide

<400> SEQUENCE: 7
aagggcgagc t                                                         11

<210> SEQ ID NO 8
<211> LENGTH: 19
<212> TYPE: DNA
<213> ORGANISM: Artificial sequence
<220> FEATURE:
<223> OTHER INFORMATION: Adapter oligonucleotide

<400> SEQUENCE: 8
cgcccttgac atagtacag                                                 19

<210> SEQ ID NO 9
<211> LENGTH: 12
<212> TYPE: DNA
<213> ORGANISM: Artificial sequence
<220> FEATURE:
<223> OTHER INFORMATION: Intermediate vector overhang sequence

```
<400> SEQUENCE: 9
gacatagtac ag                                                    12

<210> SEQ ID NO 10
<211> LENGTH: 15
<212> TYPE: DNA
<213> ORGANISM: Artificial sequence
<220> FEATURE:
<223> OTHER INFORMATION: Annealing oligonucleotide

<400> SEQUENCE: 10
caactgtact atgtc                                                 15

<210> SEQ ID NO 11
<211> LENGTH: 23
<212> TYPE: DNA
<213> ORGANISM: Artificial sequence
<220> FEATURE:
<223> OTHER INFORMATION: Adopter oligonucleotide

<400> SEQUENCE: 11
agctcgccct tattccgata gtg                                        23

<210> SEQ ID NO 12
<211> LENGTH: 11
<212> TYPE: DNA
<213> ORGANISM: Artificial sequence
<220> FEATURE:
<223> OTHER INFORMATION: Adopter oligonucleotide

<400> SEQUENCE: 12
gaataagggc g                                                     11

<210> SEQ ID NO 13
<211> LENGTH: 23
<212> TYPE: DNA
<213> ORGANISM: Artificial sequence
<220> FEATURE:
<223> OTHER INFORMATION: Adopter oligonucleotide

<400> SEQUENCE: 13
aattcgccct tattccgata gtg                                        23

<210> SEQ ID NO 14
<211> LENGTH: 12
<212> TYPE: DNA
<213> ORGANISM: Artificial sequence
<220> FEATURE:
<223> OTHER INFORMATION: Intermediate vector overhang sequence

<400> SEQUENCE: 14
attccgatag tg                                                    12

<210> SEQ ID NO 15
<211> LENGTH: 15
<212> TYPE: DNA
<213> ORGANISM: Artificial sequence
<220> FEATURE:
<223> OTHER INFORMATION: Annealing oligonucleotide

<400> SEQUENCE: 15
caacactatc ggaat                                                 15

<210> SEQ ID NO 16
<211> LENGTH: 2290
```

<212> TYPE: DNA
<213> ORGANISM: Artificial sequence
<220> FEATURE:
<223> OTHER INFORMATION: pUni/V5-His version A vector

<400> SEQUENCE: 16

| | | | | | |
|---|---|---|---|---|---|
| aattcccatg | tcagccgtta | agtgttcctg | tgtcactcaa | aattgctttg agaggctcta | 60 |
| agggcttctc | agtgcgttac | atccctggct | tgttgtccac | aaccgttaaa ccttaaaagc | 120 |
| tttaaaagcc | ttatatattc | ttttttttct | tataaaactt | aaaaccttag aggctattta | 180 |
| agttgctgat | ttatattaat | tttattgttc | aaacatgaga | gcttagtacg tgaaacatga | 240 |
| gagcttagta | cgttagccat | gagagcttag | tacgttagcc | atgagggttt agttcgttaa | 300 |
| acatgagagc | ttagtacgtt | aaacatgaga | gcttagtacg | tgaaacatga gcttagta | 360 |
| cgtactatca | acaggttgaa | ctgctgatca | acagatcctc | tacgcggccg cggtaccata | 420 |
| acttcgtata | gcatacatta | tacgaagtta | tcggaggaat | tggctcgagg aattcaccgg | 480 |
| tgccgtgtgg | gcggatccgg | gcccgacgtc | aggcctcgat | cggagctcgg taagcctatc | 540 |
| cctaaccctc | tcctcggtct | cgattctagc | catcatcacc | atcaccattg aagctcgcta | 600 |
| tcagcctcga | ctgtgccttc | tagttgccag | ccatctgttg | tttgcccctc ccccgtgcct | 660 |
| tccttgaccc | tggaaggtgc | cactcccact | gtcctttcct | aataaaatga ggaaattgca | 720 |
| tcgcattgtc | tgagtaggtg | tcattctatt | ctggggggtg | gggtggggca ggacagcaag | 780 |
| ggggaggatt | gggaagacaa | tagcaggcat | gctggggatt | ctagaagatc cggctgctaa | 840 |
| caaagcccga | aaggaagctg | agttggctgc | tgccaccgct | gagcaataac tagcataacc | 900 |
| ccttggggcc | tctaaacggg | tcttgagggg | ttttttgctg | aaaggaggaa ctatatccgg | 960 |
| atatcccggg | gtgggcgaag | aactccagca | tgagatcccc | gcgctggagg atcatccagc | 1020 |
| cggcgtcccg | gaaaacgatt | ccgaagccca | acctttcata | gaaggcggcg gtggaatcga | 1080 |
| aatctcgtga | tggcaggttg | gcgtcgcttg | gtcggtcat | ttcgaacccc agagtcccgc | 1140 |
| tcagaagaac | tcgtcaagaa | ggcgatagaa | ggcgatgcgc | tgcgaatcgg gagcggcgat | 1200 |
| accgtaaagc | acgaggaagc | ggtcagccca | ttcgccgcca | agctcttcag caatatcacg | 1260 |
| ggtagccaac | gctatgtcct | gatagcggtc | cgccacaccc | agccggccac agtcgatgaa | 1320 |
| tccagaaaag | cggccatttt | ccaccatgat | attcggcaag | caggcatcgc catgtgtcac | 1380 |
| gacgagatcc | tcgccgtcgg | gcatgcgcgc | cttgagcctg | gcgaacagtt cggctggcgc | 1440 |
| gagcccctga | tgctcttcgt | ccagatcatc | ctgatcgaca | agaccggctt ccatccgagt | 1500 |
| acgtgctcgc | tcgatgcgat | gtttcgcttg | gtggtcgaat | gggcaggtag ccggatcaag | 1560 |
| cgtatgcagc | cgccgcattg | catcagccat | gatggatact | ttctcggcag gagcaaggtg | 1620 |
| agatgacagg | agatcctgcc | ccggcacttc | gcccaatagc | agccagtccc ttcccgcttc | 1680 |
| agtgacaacg | tcgagcacag | ctgcgcaagg | aacgcccgtc | gtggccagcc acgatagccg | 1740 |
| cgctgcctcg | tcctgcagtt | cattcagggc | accggacagg | tcggtcttga caaaaagaac | 1800 |
| cgggcgcccc | tgcgctgaca | gccggaacac | ggcggcatca | gagcagccga ttgtctgttg | 1860 |
| tgcccagtca | tagccgaata | gcctctccac | ccaagcggcc | ggagaacctg cgtgcaatcc | 1920 |
| atcttgttca | atcatgcgaa | acgatcctca | tcctgtctct | tgatcagatc ttgatcccct | 1980 |
| gcgccatcag | atccttggcg | gcaagaaagc | catccagttt | actttgcagg gcttcccaac | 2040 |
| cttaccagag | ggcgccccag | ctggcaattc | cggttcgctt | gctgtccata aaaccgccca | 2100 |
| gtctagctat | cgccatgtaa | gcccactgca | agctacctgc | tttctctttg cgcttgcgtt | 2160 |

-continued

| ttcccttgtc cagatagccc agtagctgac attcatccgg ggtcagcacc gtttctgcgg | 2220 |
| actggctttc tacgtgttcc gcttccttta gcagcccttg cgccctgagt gcttgcggca | 2280 |
| gcgtgaagct | 2290 |

<210> SEQ ID NO 17
<211> LENGTH: 3906
<212> TYPE: DNA
<213> ORGANISM: Artificial sequence
<220> FEATURE:
<223> OTHER INFORMATION: pCR2.1 vector

<400> SEQUENCE: 17

| agcgcccaat acgcaaaccg cctctccccg cgcgttggcc gattcattaa tgcagctggc | 60 |
| acgacaggtt tcccgactgg aaagcgggca gtgagcgcaa cgcaattaat gtgagttagc | 120 |
| tcactcatta ggcaccccag gctttacact ttatgcttcc ggctcgtatg ttgtgtggaa | 180 |
| ttgtgagcgg ataacaattt cacacaggaa acagctatga ccatgattac gccaagcttg | 240 |
| gtaccgagct cggatccact agtaacggcc gccagtgtgc tggaattcgg cttaagccga | 300 |
| attctgcaga tatccatcac actggcggcc gctcgagcat gcatctagag ggcccaattc | 360 |
| gccctatagt gagtcgtatt acaattcact ggccgtcgtt ttacaacgtc gtgactggga | 420 |
| aaaccctggc gttacccaac ttaatcgcct tgcagcacat ccccctttcg ccagctggcg | 480 |
| taatagcgaa gaggcccgca ccgatcgccc ttcccaacag ttgcgcagcc tgaatggcga | 540 |
| atgggacgcg ccctgtagcg gcgcattaag cgcggcgggt gtggtggtta cgcgcagcgt | 600 |
| gaccgctaca cttgccagcg ccctagcgcc cgctcctttc gctttcttcc cttcctttct | 660 |
| cgccacgttc gccggctttc cccgtcaagc tctaaatcgg gggctccctt tagggttccg | 720 |
| atttagagct ttacggcacc tcgaccgcaa aaaacttgat ttgggtgatg gttcacgtag | 780 |
| tgggccatcg ccctgataga cggtttttcg ccctttgacg ttggagtcca cgttctttaa | 840 |
| tagtggactc ttgttccaaa ctggaacaac actcaaccct atcgcggtct attcttttga | 900 |
| tttataaggg attttgccga tttcggccta ttggttaaaa atgagctga tttaacaaat | 960 |
| tcagggcgca agggctgcta aggaaccgg aacacgtaga aagccagtcc gcagaaacgg | 1020 |
| tgctgacccc ggatgaatgt cagctactgg gctatctgga caagggaaaa cgcaagcgca | 1080 |
| aagagaaagc aggtagcttg cagtgggctt acatggcgat agctagactg gcggttttta | 1140 |
| tggacagcaa gcgaaccgga attgccagct ggggcgccct ctggtaaggt tgggaagccc | 1200 |
| tgcaaagtaa actggatggc tttcttgccg ccaaggatct gatggcgcag gggatcaaga | 1260 |
| tctgatcaag agacaggatg aggatcgttt cgcatgattg aacaagatgg attgcacgca | 1320 |
| ggttctccgg ccgcttgggt ggagaggcta ttcggctatg actgggcaca acagacaatc | 1380 |
| ggctgctctg atgccgccgt gttccggctg tcagcgcagg ggcgcccggt tctttttgtc | 1440 |
| aagaccgacc tgtccggtgc cctgaatgaa ctgcaggacg aggcagcgcg gctatcgtgg | 1500 |
| ctggccacga cgggcgttcc ttgcgcagct gtgctcgacg ttgtcactga agcgggaagg | 1560 |
| gactggctgc tattgggcga agtgccgggg caggatctcc tgtcatctcg ccttgctcct | 1620 |
| gccgagaaag tatccatcat ggctgatgca atgcggcggc tgcatacgct tgatccggct | 1680 |
| acctgcccat tcgaccacca agcgaaacat cgcatcgagc gagcacgtac tcggatggaa | 1740 |
| gccggtcttg tcgatcagga tgatctggac gaagagcatc aggggctcgc gccagccgaa | 1800 |
| ctgttcgcca ggctcaaggc gcgcatgccc gacggcgagg atctcgtcgt gatccatggc | 1860 |
| gatgcctgct tgccgaatat catggtggaa aatggccgct tttctggatt caacgactgt | 1920 |

```
ggccggctgg gtgtggcgga ccgctatcag gacatagcgt tggataccg tgatattgct      1980 gaagagcttg gcggcgaatg ggctgaccgc ttcctcgtgc tttacggtat cgccgctccc      2040
gattcgcagc gcatcgcctt ctatcgcctt cttgacgagt tcttctgaat tgaaaaagga      2100
agagtatgag tattcaacat ttccgtgtcg cccttattcc cttttttgcg gcattttgcc      2160
ttcctgtttt tgctcaccca gaaacgctgg tgaaagtaaa agatgctgaa gatcagttgg      2220
gtgcacgagt gggttacatc gaactggatc tcaacagcgg taagatcctt gagagttttc      2280
gccccgaaga acgttttcca atgatgagca cttttaaagt tctgctatgt catacactat      2340
tatcccgtat tgacgccggg caagagcaac tcggtcgccg ggcgcggtat tctcagaatg      2400
acttggttga gtactcacca gtcacagaaa agcatcttac ggatggcatg acagtaagag      2460
aattatgcag tgctgccata accatgagtg ataacactgc ggccaactta cttctgacaa      2520
cgatcggagg accgaaggag ctaaccgctt ttttgcacaa catgggggat catgtaactc      2580
gccttgatcg ttgggaaccg gagctgaatg aagccatacc aaacgacgag agtgacacca      2640
cgatgcctgt agcaatggca acaacgttgc gcaaactatt aactggcgaa ctacttactc      2700
tagcttcccg gcaacaatta atagactgga tggaggcgga taaagttgca ggaccacttc      2760
tgcgctcggc ccttccggct ggctggttta ttgctgataa atctggagcc ggtgagcgtg      2820
ggtctcgcgg tatcattgca gcactggggc cagatggtaa gccctcccgt atcgtagtta      2880
tctacacgac ggggagtcag gcaactatgg atgaacgaaa tagacagatc gctgagatag      2940
gtgcctcact gattaagcat tggtaactgt cagaccaagt ttactcatat atactttaga      3000
ttgatttaaa acttcatttt taatttaaaa ggatctaggt gaagatcctt tttgataatc      3060
tcatgaccaa aatcccttaa cgtgagtttt cgttccactg agcgtcagac cccgtagaaa      3120
agatcaaagg atcttcttga gatccttttt ttctgcgcgt aatctgctgc ttgcaaacaa      3180
aaaaaccacc gctaccagcg gtggtttgtt tgccggatca agagctacca actctttttc      3240
cgaaggtaac tggcttcagc agagcgcaga taccaaatac tgtccttcta gtgtagccgt      3300
agttaggcca ccacttcaag aactctgtag caccgcctac atacctcgct ctgctaatcc      3360
tgttaccagt ggctgctgcc agtggcgata gtcgtgtct taccgggttg gactcaagac      3420
gatagttacc ggataaggcg cagcggtcgg gctgaacggg gggttcgtgc acacagccca      3480
gcttggagcg aacgacctac accgaactga gatacctaca gcgtgagcat tgagaaagcg      3540
ccacgcttcc cgaagggaga aaggcggaca ggtatccggt aagcggcagg gtcggaacag      3600
gagagcgcac gagggagctt ccaggggaa acgcctggta tctttatagt cctgtcgggt      3660
ttcgccacct ctgacttgag cgtcgatttt tgtgatgctc gtcaggggg cggagcctat      3720 ggaaaaacgc cagcaacgcg gcctttttac ggttcctggc cttttgctgg ccttttgctc      3780
acatgttctt tcctgcgtta tcccctgatt ctgtggataa ccgtattacc gcctttgagt      3840
gagctgatac cgctcgccgc agccgaacga ccgagcgcag cgagtcagtg agcgaggaag      3900
cggaag                                                              3906
```

<210> SEQ ID NO 18
<211> LENGTH: 310
<212> TYPE: DNA
<213> ORGANISM: Artificial sequence
<220> FEATURE:
<223> OTHER INFORMATION: pUNI vector multiple cloning site

<400> SEQUENCE: 18

```
gagcttagta cgtactatca acaggttgaa ctgctgatca acagatcctc tacgcggccg      60
cggtaccata acttcgtata gcatacatta tacgaagtta tcggaggaat tggctcgagg     120
aattcaccgg tgccgtgtgg gcggatccgg gcccgacgtc aggcctcgat cggagctcgg     180
taagcctatc cctaaccctc tcctcggtct cgattctagc catcatcacc atcaccattg     240
aagctcgcta tcagcctcga ctgtgccttc tagttgccag ccatctgttg tttgcccctc     300
ccccgtgcct                                                             310
```

<210> SEQ ID NO 19
<211> LENGTH: 20
<212> TYPE: PRT
<213> ORGANISM: Artificial sequence
<220> FEATURE:
<223> OTHER INFORMATION: Segment of pUni/V5-His version A vector

<400> SEQUENCE: 19

Gly Lys Pro Ile Pro Asn Pro Leu Leu Gly Leu Asp Ser Ser His His
1               5                   10                  15

His His His His
            20

<210> SEQ ID NO 20
<211> LENGTH: 29
<212> TYPE: DNA
<213> ORGANISM: Artificial sequence
<220> FEATURE:
<223> OTHER INFORMATION: Adapter and portion of vector sequence

<400> SEQUENCE: 20

```
gaattgatcc cttcaccgac atagtacag                                        29
```

<210> SEQ ID NO 21
<211> LENGTH: 17
<212> TYPE: DNA
<213> ORGANISM: Artificial sequence
<220> FEATURE:
<223> OTHER INFORMATION: Adapter and portion of vector sequence

<400> SEQUENCE: 21

```
ggtgaaggga tcaattc                                                     17
```

<210> SEQ ID NO 22
<211> LENGTH: 24
<212> TYPE: DNA
<213> ORGANISM: Artificial sequence
<220> FEATURE:
<223> OTHER INFORMATION: Adapter and portion of vector sequence

<400> SEQUENCE: 22

```
gagctcgccc ttgacatagt acag                                             24
```

<210> SEQ ID NO 23
<211> LENGTH: 12
<212> TYPE: DNA
<213> ORGANISM: Artificial sequence
<220> FEATURE:
<223> OTHER INFORMATION: Adapter and portion of vector sequence

<400> SEQUENCE: 23

```
aagggcgagc tc                                                          12
```

<210> SEQ ID NO 24
<211> LENGTH: 32

```
<210> SEQ ID NO 24
<211> LENGTH: 32
<212> TYPE: DNA
<213> ORGANISM: Artificial sequence
<220> FEATURE:
<223> OTHER INFORMATION: Adapter and portion of vector sequence

<400> SEQUENCE: 24
caactgtact atgtcggtga agggatcaat tc                                    32

<210> SEQ ID NO 25
<211> LENGTH: 24
<212> TYPE: DNA
<213> ORGANISM: Artificial sequence
<220> FEATURE:
<223> OTHER INFORMATION: Adapter and portion of vector sequence

<400> SEQUENCE: 25
aagctcgccc ttattccgat agtg                                             24

<210> SEQ ID NO 26
<211> LENGTH: 16
<212> TYPE: DNA
<213> ORGANISM: Artificial sequence
<220> FEATURE:
<223> OTHER INFORMATION: Adapter and portion of vector sequence

<400> SEQUENCE: 26
gaataagggc gagctt                                                      16

<210> SEQ ID NO 27
<211> LENGTH: 12
<212> TYPE: DNA
<213> ORGANISM: Artificial sequence
<220> FEATURE:
<223> OTHER INFORMATION: Adapter and portion of vector sequence

<400> SEQUENCE: 27
aagggcgaat tc                                                          12

<210> SEQ ID NO 28
<211> LENGTH: 24
<212> TYPE: DNA
<213> ORGANISM: Artificial sequence
<220> FEATURE:
<223> OTHER INFORMATION: Adapter and portion of vector sequence

<400> SEQUENCE: 28
gaattcgccc ttattccgat agtg                                             24

<210> SEQ ID NO 29
<211> LENGTH: 27
<212> TYPE: DNA
<213> ORGANISM: Artificial sequence
<220> FEATURE:
<223> OTHER INFORMATION: Adapter and portion of vector sequence

<400> SEQUENCE: 29
caacactatc ggaataaggg cgaattc                                          27

<210> SEQ ID NO 30
<211> LENGTH: 12
<212> TYPE: DNA
<213> ORGANISM: Artificial sequence
<220> FEATURE:
<223> OTHER INFORMATION: Adapter and portion of vector sequence

<400> SEQUENCE: 30
```

```
<210> SEQ ID NO 31
<211> LENGTH: 15
<212> TYPE: DNA
<213> ORGANISM: Artificial sequence
<220> FEATURE:
<223> OTHER INFORMATION: Adapter and portion of vector sequence

<400> SEQUENCE: 31
caacactatc ggaat                                                         15

<210> SEQ ID NO 32
<211> LENGTH: 12
<212> TYPE: DNA
<213> ORGANISM: Artificial sequence
<220> FEATURE:
<223> OTHER INFORMATION: Adapter and portion of vector sequence

<400> SEQUENCE: 32
attccgatag tg                                                            12

<210> SEQ ID NO 33
<211> LENGTH: 12
<212> TYPE: DNA
<213> ORGANISM: Artificial sequence
<220> FEATURE:
<223> OTHER INFORMATION: Adapter and portion of vector sequence

<400> SEQUENCE: 33
aagctcgccc tt                                                            12

<210> SEQ ID NO 34
<211> LENGTH: 12
<212> TYPE: DNA
<213> ORGANISM: Artificial sequence
<220> FEATURE:
<223> OTHER INFORMATION: Adapter and portion of vector sequence

<400> SEQUENCE: 34
gaattcgccc tt                                                            12
```